US 8,137,676 B2

United States Patent
Palese et al.

(10) Patent No.: US 8,137,676 B2
(45) Date of Patent: Mar. 20, 2012

(54) GENETICALLY ENGINEERED EQUINE INFLUENZA VIRUS AND USES THEREOF

(75) Inventors: Peter Palese, Leonia, NJ (US); Adolfo Garcia-Sastre, New York, NY (US); Thomas Chambers, Lexington, KY (US)

(73) Assignees: Mount Sinai School of Medicine, New York, NY (US); University of Kentucky, Lexington, KY (US)

( * ) Notice: Subject to any disclaimer, the term of this patent is extended or adjusted under 35 U.S.C. 154(b) by 257 days.

(21) Appl. No.: 11/884,401

(22) PCT Filed: Jun. 1, 2005

(86) PCT No.: PCT/US2005/019383
§ 371 (c)(1),
(2), (4) Date: May 20, 2008

(87) PCT Pub. No.: WO2006/088481
PCT Pub. Date: Aug. 24, 2006

(65) Prior Publication Data
US 2008/0254060 A1    Oct. 16, 2008

Related U.S. Application Data

(60) Provisional application No. 60/653,588, filed on Feb. 15, 2005.

(51) Int. Cl.
*A61K 39/145* (2006.01)
(52) U.S. Cl. .................. 424/206.1; 424/209.1
(58) Field of Classification Search .......... None
See application file for complete search history.

(56) References Cited

U.S. PATENT DOCUMENTS

| | | | |
|---|---|---|---|
| 4,071,618 A | 1/1978 | Konobe et al. | |
| 4,567,147 A | 1/1986 | Ooi et al. | |
| 4,659,569 A | 4/1987 | Mitsuhashi et al. | |
| 4,693,981 A | 9/1987 | Wiesehahn et al. | |
| 5,106,619 A | 4/1992 | Wiesehahn et al. | |
| 5,166,057 A | 11/1992 | Palese et al. | |
| 5,674,502 A | 10/1997 | Ennis et al. | |
| 5,766,601 A | 6/1998 | Ennis | |
| 5,786,199 A | 7/1998 | Palese et al. | |
| 5,820,871 A | 10/1998 | Palese et al. | |
| 5,854,037 A | 12/1998 | Palese et al. | |
| 5,866,694 A | 2/1999 | Katinger et al. | |
| 5,882,650 A | 3/1999 | Ennis | |
| 5,891,705 A | 4/1999 | Budowsky et al. | |
| 6,146,642 A | 11/2000 | Garcia-Sastre | |
| 6,146,873 A | 11/2000 | Kistner et al. | |
| 6,162,432 A | 12/2000 | Wallner et al. | |
| 6,300,090 B1 | 10/2001 | Steinman et al. | |
| 6,326,151 B1 | 12/2001 | Katze et al. | |
| 6,468,544 B1 | 10/2002 | Egorov et al. | |
| 6,544,785 B1 | 4/2003 | Palese et al. | |
| 6,573,079 B1 | 6/2003 | Palese et al. | |
| 6,635,246 B1 | 10/2003 | Barrett et al. | |
| 6,635,416 B2 | 10/2003 | Palese et al. | |
| 6,649,372 B1 | 11/2003 | Palese et al. | |
| 6,669,943 B1 | 12/2003 | Palese et al. | |
| 6,800,288 B2 | 10/2004 | Ferko et al. | |
| 6,852,522 B1 | 2/2005 | Palese et al. | |
| 6,866,853 B2 | 3/2005 | Egorov et al. | |
| 6,884,414 B1 | 4/2005 | Palese et al. | |
| 7,060,430 B2 | 6/2006 | Palese et al. | |
| 7,344,722 B1 | 3/2008 | Maassab et al. | |
| 7,442,527 B2 | 10/2008 | Palese et al. | |
| 7,494,659 B2 | 2/2009 | Katinger et al. | |
| 7,494,808 B2 | 2/2009 | Palese et al. | |
| 7,588,768 B2 | 9/2009 | Palese et al. | |
| 7,833,774 B2 | 11/2010 | Palese et al. | |
| 2004/0109877 A1 | 6/2004 | Palese et al. | |
| 2004/0253273 A1 | 12/2004 | Palese et al. | |
| 2005/0054074 A1 | 3/2005 | Palese et al. | |
| 2006/0216701 A1 | 9/2006 | Palese et al. | |
| 2007/0122430 A1 | 5/2007 | Shneider et al. | |
| 2007/0172929 A1 | 7/2007 | Maassab et al. | |
| 2008/0050402 A1 | 2/2008 | Zhou et al. | |
| 2008/0234175 A1 | 9/2008 | Montelione et al. | |
| 2009/0010962 A1 | 1/2009 | Palese et al. | |
| 2009/0028901 A1 | 1/2009 | Palese et al. | |
| 2009/0053264 A1 | 2/2009 | Palese et al. | |
| 2009/0123495 A1 | 5/2009 | Sachet et al. | |
| 2009/0203114 A1 | 8/2009 | Palese et al. | |
| 2010/0158942 A1 | 6/2010 | Palese et al. | |
| 2010/0233785 A1 | 9/2010 | Brandt et al. | |

FOREIGN PATENT DOCUMENTS

| | | |
|---|---|---|
| DE | 100 20 505 | 10/2001 |
| EP | 702085 A1 | 3/1996 |
| EP | 780475 A1 | 6/1997 |
| EP | 780475 B1 | 6/1997 |
| EP | 1085904 | 12/1999 |
| EP | 1098961 | 1/2008 |

(Continued)

OTHER PUBLICATIONS

Talon et al., Influenza A and B viruses expressing altered NS1 proteins: A vaccine approach, 2000, PNAS, vol. 97, No. 8, pp. 4309-4314.*

(Continued)

*Primary Examiner* — Benjamin P Blumel
(74) *Attorney, Agent, or Firm* — Jones Days

(57) ABSTRACT

The present invention relates, in general, to attenuated equine influenza viruses having an impaired ability to antagonize the cellular interferon (IFN) response, and the use of such attenuated viruses in vaccine and pharmaceutical formulations. In particular, the invention relates to attenuated equine influenza viruses having modifications to an equine NS1 gene that diminish or eliminate the ability of the NS1 gene product to antagonize the cellular IFN response. These viruses replicate in vivo, but demonstrate decreased replication, virulence and increased attenuation, and therefore are well suited for use in live virus vaccines, and pharmaceutical formulations.

6 Claims, 7 Drawing Sheets

FOREIGN PATENT DOCUMENTS

Figure 1A:
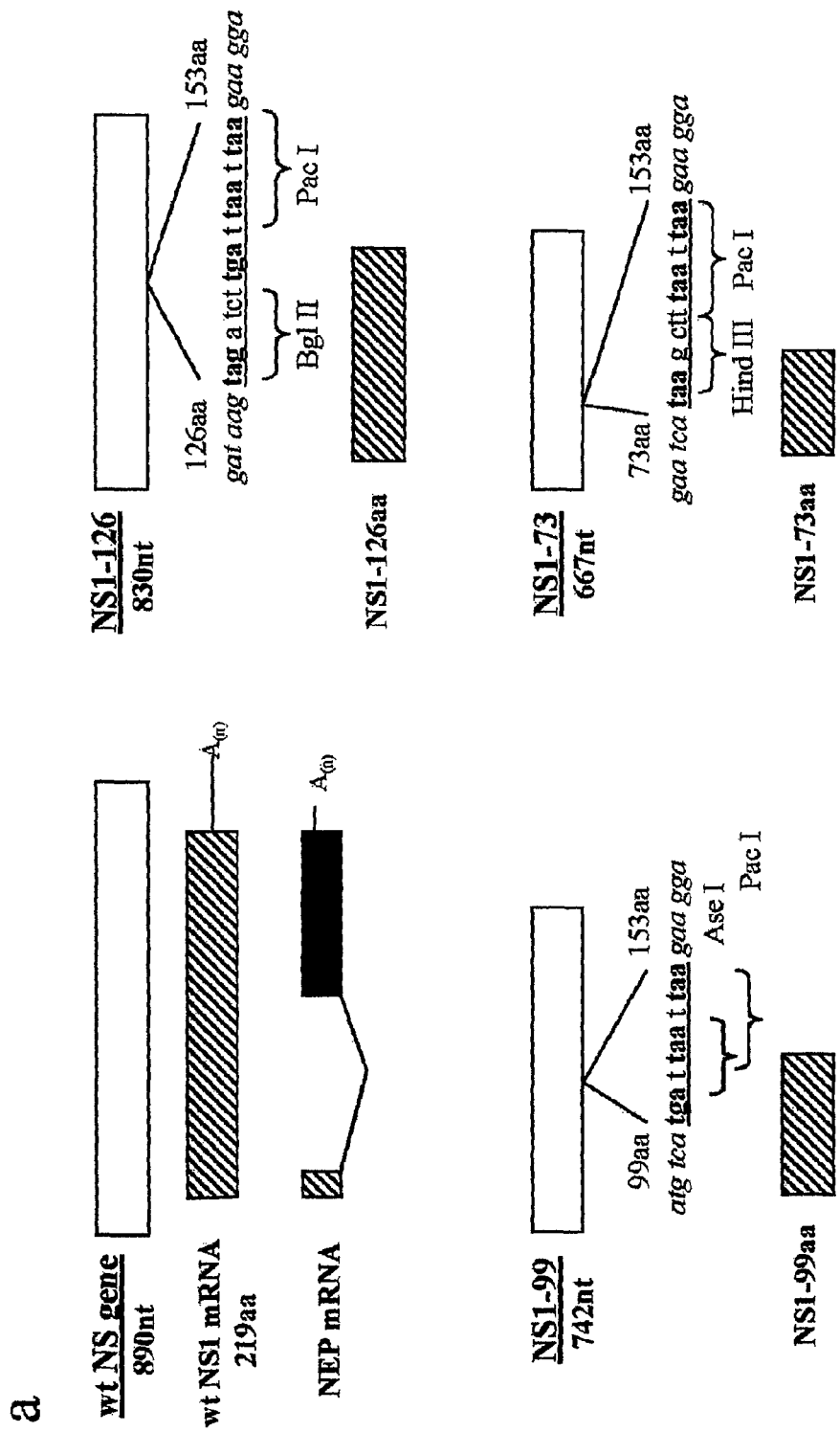

| JP | 59-39831 | 3/1984 |
|---|---|---|
| WO | WO 93/006866 | 4/1993 |
| WO | WO 96/10632 | 4/1996 |
| WO | WO 96/34625 A1 | 11/1996 |
| WO | WO 97/06270 A1 | 2/1997 |
| WO | WO 97/08292 | 3/1997 |
| WO | WO 97/12032 A1 | 4/1997 |
| WO | WO 98/02530 A1 | 1/1998 |
| WO | WO 98/13501 A2 | 4/1998 |
| WO | WO 98/53078 A1 | 11/1998 |
| WO | WO 99/02657 A1 | 1/1999 |
| WO | WO 99/15672 A1 | 4/1999 |
| WO | WO 99/64068 | 12/1999 |
| WO | WO 99/64570 | 12/1999 |
| WO | WO 99/64571 | 12/1999 |
| WO | WO 01/04333 | 1/2001 |
| WO | WO 01/64860 | 9/2001 |
| WO | WO 01/077394 | 10/2001 |
| WO | WO 02/24876 | 3/2002 |
| WO | WO 06/083286 | 8/2006 |
| WO | WO 2006/088481 | 8/2006 |

OTHER PUBLICATIONS

Genbank Accession # AF001673, Influenza A virus (A/eq/LaPlata/93 H3N8)) nonstructural, Published Aug. 12, 1998.*
Aebi, 1989, "cDNA structures and regulation of two interferon-induced human Mx proteins." Mol. Cell. Biol. 11:5062.
Aoki K et al., 1996, "Differential sensitivity of two related viruses, Newcastle disease virus and Sendai virus, to interferon in mouse Had-2 cells selective inhibition of translation of NDV mRNA.", Arch Virol.;141(10):1847-62.
Aragon et al., 2000, "Eukaryotic translation initiation factor 4GI is a cellular target for NS1 protein, a translational activator of influenza virus." Mol. Cell. Biol. 20:6259-6268.
Arvin et al., 2006, "New viral vaccines." Virology, vol. 344:240-249.
Baez M et al., 1980, "Complete nucleotide sequence of the influenza A/PR/8/34 virus NS gene and comparison with the NS genes of the A/Udorn/72 and A/FPV/Rostock/34 strains", Nucleic Acids Res. Dec. 11;8(23):5845-58.
Baskin et al., 2007, Functional genomic and serological analysis of the protective immune response resulting from vaccination of macaques with an NSI-truncated influenza virus. J Virol. 81(21):11817-27.
Basler et al., 2000, "The Ebola virus VP35 protein functions as a type I IFN antagonist." Proc Natl Acad Sci U S A. Oct. 24;97(22):12289-94.
Beatrice et al., 1980, "Immunogenicity in mice of temperature-sensitive mutants of vesicular stomatitis virus: early appearance in bronchial secretions of an interferon-like inhibitor", J Gen Virol.; 47:529-533.
Beattie et al., 1995, "Reversal of the Interferon-Sensitive Phenotype of a Vaccinia Virus Lacking E3L by Expression of the Reovirus S4 Gene," J. Virology 69(1):499-505.
Belardelli & Gresser, 1996, "The neglected role of type I interferon in the T-cell response: implications for its clinical use." Immunol. Today 17:369-372.
Bergmann et al., 2000, "Influenza virus NS1 protein counteracts PKR-mediated inhibition of replication." Virol. Jul.;74(13):6203-6.
Bossert et al., 2002, "Respiratory Syncytial Virus (RSV) Nonstructural (NS) Proteins as Host Range Determinants: a Chimeric Bovine RSV with NS Genes from Human RSV Is Attenuated in Interferon-Competent Bovine Cells", J. of Virology 76:4287-93.
Bouloy et al., 2001, "Genetic evidence for an interferon-antagonistic function of rift valley fever virus nonstructural protein NSs." J Virol. Feb.;75(3):1371-7.
Briscoe et al., 1996, Kinase-negative mutants of JAK I can sustain interferon-gamma-inducible gene expression but not an antiviral state, EMBO J. 15:799-809.
Buonagurio Da et al., 1986, "Evolution of human influenza A viruses over 50 years: rapid, uniform rate of change in NS gene", Science. May 23;232(4753):980-2.
Butterfield et al., 1978, "Vaccination for fowl plague", Am J Vet Res. Apr.; 39(4):671-674.

Chang et al., 1992,"The E3L gene of vaccinia virus encodes an inhibitor of the interferon-induced, double-stranded RNA-dependent protein kinase.", Proc Natl Acad Sci U S A. Jun. 1;89(11):4825-9.
Chen Z et al., 1999, "Influenza A virus NSI protein targets poly(A)-binding protein II of the cellular 3'-end processing machinery", EMBO J. Apr. 15;18(8):2273-83.
Clemens and Elia, 1997, "The Double Stranded RNA-Dependent Protein Kinase PKR: Structure and Function", Journal of Interferon and Cytokine Research, 17:503-524.
Constantinescu et al., 1995, "Expression and signaling specificity of the IFNAR chain of the type I interferon receptor complex." Proc. Natl. Acad. Sci. USA 92:10487-91.
Cossins et al., 1993, "Precise prediction of a Kk-restricted cytotoxic T cell epitope in the NS1 protein of influenza virus using an MHC allele-specific motif.", Virology. Mar.;193(1):289-95.
Crowe Je, 1998, "Immune responses of infants to infection with respiratory viruses and live attenuated respiratory virus candidate vaccines", Vaccine. Aug.; 16(14/15):1423-1432.
Cruse et al, 2003, *Illustrated Dictionary of Immunology*, 2nd Edition, Cruse et al. Editors, CRC Press, pp. 367, under "Knockout Gene".
Da Silva et al., 2006, Vaccines under development: group B streptococcus, herpes-zoster, HIV, malaria and dengue, Jornal de Pediatria, vol. 82, Suppl. 3, pp. S115-124.
De La Luna S et al., 1995, "Influenza virus NS1 protein enhances the rate of translation initiation of viral mRNAs", J Virol. Apr.;69(4):2427-33.
Desmyter J et al., 1968, "Defectiveness of interferon production and of rubella virus interference in a line of African green monkey kidney cells (Vero)", J Virol. Oct.;2(10):955-61.
Diaz Mo et al., 1988, "Homozygous deletion of the alpha- and beta 1-interferon genes in human leukemia and derived cell lines", Proc Natl Acad Sci U S A. Jul.;85(14):5259-63.
Didcock et al., 1999, "The V Protein of Simian Virus 5 Inhibits Interferon Signalling by Targeting STATI for Proteasome-Mediated Degradation", J. of Virology, 73(12): 9928-9933.
Donelan et al., 2004, "The N- and C-terminal domains of the NS1 protein of influenza B virus can independently inhibit IRF-3 and beta interferon promoter activation." J Virol. Nov.;78(21):11574-82.
Donelan et al., 2003, A recombinant influenza A virus expressing an RNA-binding-defective NS1 protein induces high levels of beta interferon and is attenuated in mice. J Virol. Dec.;77(24):13257-66.
Dulbecco R, 1988, "Multiplication and Genetics of Animal Viruses", Ch. 48, in Dulbecco et al., Editors, *Virology*, pp. 77-79.
Durbin Je et al., 1996, "Targeted disruption of the mouse Statl gene results in compromised innate immunity to viral disease", Cell. Feb. 9;84(3):443-50.
Easterday , 1980, "Animals in the Influenza World." Philos Trans R Soc Lond B Biol Sci 288:433-7.
Efferson et al., 2005, "Stimulation of human T cells by an influenza A vector expressing a CTL epitope from the HER-2/neu protooncogene results in higher numbers of antigen-specific TCRhi cells than stimulation with peptide." Divergent roles of IL-2 and IL-15. Anticancer Res. Mar.-Apr.;25(2A):715-24.
Efferson et al., 2006, "Prostate tumor cells infected with a recombinant influenza virus expressing a truncated NS1 protein activate cytolytic CD8+ cells to recognize noninfected tumor cells." J Virol. 80(1):383-394.
Egorov A et al., 1994, "The NS gene—a possible determinant of apathogenicity of a cold-adapted donor of attenuation A /Leningrad/ 134/47/57 and its reassortants." Vopr Virusol. Sep.-Oct.;39(5):201-5. Russian.
Egorov A et al., 1998, "Transfectant influenza A viruses with long deletions in the NS1 protein grow efficiently in Vero cells", J Virol. Aug.;72(8):6437-41.
Egorov et al., 1997, "Generation of Influenza A Transfectant Viruses Containing Deletions in the NS1 Protein", Institute of Applied Microbiology, in Emergence and Re-emergence of Negative Strand Viruses, Tenth International Conference on Negative Strand Viruses. Sep. 21-26, Dublin, Ireland. Poster.
Egorov Ay et al., 1997, "Generation of influenza A transfectant viruses containing deletions of the carboxyl-terminal part of the NS1 protein", in *Emergence and Re-emergence of Negative Strand*

*Viruses, Tenth International Conference on Negative Strand Viruses.* Dublin, Ireland. Abstract No. 108, p. 104.

Enami K et al., 1994, "Influenza virus NS1 protein stimulates translation of the M1 protein", J Virol. Mar.;68(3):1432-7.

Enami M and Palese P.,1991, "High-efficiency formation of influenza virus transfectants", J Virol.;65(5):2711-3.

Enami M et al., 1991, "An influenza virus containing nine different RNA segments", Virology 185(1):291-8.

Falcon et al., 2005, "Attenuation and immunogenicity in mice of temperature-sensitive influenza viruses expressing truncated NS1 proteins." J Gen Virol. Oct.;86(Pt 10):2817-21.

Ferko et al., 2004, "Immunogenicity and protection efficacy of replication-deficient influenza A viruses with altered NS1 genes." J Virol. 78(23):13037-13045.

Fernandez-Sesma et al., 2006, "Influenza virus evades innate and adaptive immunity via the NS1 protein." J Virol. 80(13):6295-304.

Fenner et al. 1974. *The Biology of Animal Viruses* $2^{nd}$ Ed. New York: Academic Press. 42-43.

Finn, Ol 2003, "Cancer vaccines: between the idea and the reality." Nature 3:630-641.

Fodor E et al., 1998, "Attenuation of influenza A virus mRNA levels by promoter mutations", J Virol. 72(8):6283-90.

Fodor et al., 1999, "Rescue of influenza A virus from recombinant DNA." J. Virol 73:9679-9682.

Fortes P et al., 1994, "Influenza virus NS1 protein inhibits pre-mRNA splicing and blocks mRNA nucleocytoplasmic transport", EMBO J. Feb. 1;13(3):704-12.

Garcia-Sastre A et al., 1998, "Influenza A virus lacking the NS1 gene replicates in interferon-deficient systems", Virology. Dec. 20;252(2):324-30.

Garcia-Sastre A et al., 1998, "The role of interferon in influenza virus tissue tropism", J Virol. Nov.;72(11):8550-8.

Garcia-Sastre A. 2001, "Inhibition of interferon-mediated antiviral responses by influenza A viruses and other negative-strand RNA viruses." Virology. 279(2):375-384.

Garcia-Sastre et al., 2002, "Mechanisms of inhibition of the host interferon alpha/beta-mediated antiviral responses by viruses." Microbes Infect 4:647-55.

Garcin et al., 1999, "Sendai Virus C Proteins Counteract the Interferon-Mediated Induction of an Antiviral State", J. Virology 73(8): 6559-6565.

Geiss et al., 2002, "Cellular transcriptional profiling in influenza A virus-infected lung epithelial cells: the role of the nonstructural NS1 protein in the evasion of the host innate defense and its potential contribution to pandemic influenza." Proc Natl Acad Sci U S A. Aug. 6;99(16):10736-41.

Genbank Accession No. AJ293939 (A/swine/Italy/13962/95 (H3N2)), Nov. 14, 2006.

Genbank Accession No. AJ344041(A/swine/Cotes d'Armor/1121/00(H1N1))/13962/95 (H3N2)), Nov. 14, 2006.

Genbank Accession No. AJ430785 (Influenza A virus (A/equi-2/Ludhiana/87(H3N8)) genomic RNA for nonstructural protein (NS1 gene), isolate A/equi-2/Ludhiana/87(H3N8), Apr. 15, 2005.

Genbank Accession No. AY328471 (Influenza A virus (A/equine/Grobois/I/98(H3N8)) nonstructural protein NSI mRNA, complete cds), Jul. 23, 2003.

Genbank Accession No. X80060 (Influenza A virus (A/equine 2/Suffolk/89(H3N8)) NS1 gene), Apr. 18, 2005.

Genbank Accession No. AF001673 (Influenza A virus (A/eq/LaPlata/93(H3N8)) nonstructural proteins NS1 and NS2 (NS) gene, complete cds), Aug. 12, 1998.

Genbank Accession No. AF001672 (Influenza A virus A/eq/Lambourn/22778/92(H3N8)) nonstructural proteins NS1 and NS2 (NS) gene, complete cds.), Aug. 12, 1998.

Genbank Accession No. AF001671 (Influenza A virus (A/eq/Kentucky/92(H3N8)) nonstructural proteins NS1 and NS2 (NS) gene, complete cds), Aug. 12, 1998.

Genbank Accession No. AF001670 (Influenza A virus (A/eq/Hong Kong/1/92(H3N8)) nonstructural proteins NS1 and NS2 (NS) gene, complete cds), Aug. 12, 1998.

Genbank Accession No. AF001669 (Influenza A virus (A/eq/Roma/5/91(H3N8)) nonstructural proteins NSI and NS2 (NS) gene, complete cds), Aug. 12, 1998.

Genbank Accession No. AF001668 (Influenza A virus (A/eq/Arunde1/12369/91(H3N8)) nonstructural proteins NS1 and NS2 (NS) gene, complete cds), Aug. 12, 1998.

Genbank Accession No. A F001667 (Influenza A virus (A/eq/Alaska/1/91(H3N8)) nonstructural proteins NS1 and NS2 (NS) gene, complete cds), Aug. 12, 1998.

Genbank Accession No. A F001666 (Influenza A virus (A/eq/Yvelines/2136/89(H3N8)) nonstructural proteins NS1 and NS2 (NS) gene, complete cds) Aug. 12, 1998.

Genbank Accession No. AF001665 (Influenza A virus (A/eq/LaPlata/1/88(H3N8)) nonstructural proteins NS1 and NS2 (NS) gene, complete cds) Aug. 12, 1998.

Genbank Accession No. A F001664 (Influenza A virus (A/eq/Kentucky/1/88(H3N8)) nonstructural proteins NS1 and NS2 (NS) gene, complete cds) Aug. 12, 1998.

Genbank Accession No. A F001663 (Influenza A virus (A/eq/Newmarket/1/77(H7N7)) nonstructural proteins NS1 and NS2 (NS) gene, complete cds) Aug. 12, 1998.

Genbank Accession No. A F001662 (Influenza A virus (A/eq/Newmarket/D63/79(H3N8)) nonstructural proteins NS1 and NS2 (NS) gene, complete cds) Aug. 12, 1998.

Genbank Accession No. U49489 (Influenza A virus (A/equine/Prague/1/1956(H7N7)) nonstructural protein NS2 (NS) gene. partial cds, alternatively spliced; and nonstructural protein NS1 (NS) gene, partial cds) Apr. 16, 2006.

Genbank Accession No. U49487 (Influenza A virus (A/equine/Tennessee/5/1986(H3N8)) nonstructural protein NS2 (NS) gene, partial cds, alternatively spliced; and nonstructural protein NS1 (NS) gene, partial cds) Apr. 16, 2006.

Genbank Accession No. U49486 (Influenza A virus (A/equine/London/1416/1973(H7N7)) nonstructural protein NS2 (NS) gene. partial cds, alternatively spliced; and nonstructural protein NS1 (NS) gene, partial cds) Apr. 16, 2006.

Genbank Accession No. M65020 (Influenza A virus (A/equine/Jilin/1/1989(H3N8)) NS2 protein (NS2) and NS1 protein (NS1) genes, complete cds) May 23, 2006.

Genbank Accession No. AB116564 (Sus scrofa stat1 mRNA for signal transducer and activator of transcription I. complete cds) Dec. 27, 2003.

Genbank Accession No. NM_213769 (Sus scrofa signal transducer and activator of transcription I (STAT1). mRNA) Dec. 9, 2003.

Gonzalo et al., 1999, "Enhanced CD8+ T cell response to HIV-1 env by combined immunization with influenza and vaccinia virus recombinants." Vaccine. Feb. 26;17(7-8):887-92.

Goodpasture et al., 1934, "The cultivation of vaccine and other viruses in the chorioallantoic membrane of chick embryos", Science.; 74(1919):371-372.

Gorse & Belshe, 1990, "Enhancement of anti-influenza A virus cytotoxicity following influenza A virus vaccination in older, chronically ill adults."J. Clin. Microbiol. 28:2539-2550.

Gorse et al., 1995, "Increased anti-influenza A virus cytotoxic T cell activity following vaccination of the chronically ill elderly with live attenuated or inactivated influenza virus vaccine." J. Infect Dis 172:1-10.

Gotoh et al., 1999, "Knockout of the Sendai Virus C Gene Eliminates the Viral Ability to Prevent the Interferon-$\alpha/\beta$-Mediated Responses." FEBS Letters 459:205-210.

Hackett CJ et al., 1992, "Influenza virus infection elicits class II major histocompatibility complex-restricted T Cells specific for an epitope identified in the NS1 non-structural protein.", J Gen Virol. Jun.;73( Pt 6):1339-43.

Haller et al., 1986, "Genetic resistance to influenza virus in wild mice", Curr Top Microbiol Immunol. 127:331-7.

Haller O et al., 1980, "Host gene influences sensitivity to interferon action selectively for influenza virus", Nature. Feb 14;283(5748):660-2.

Haller et al., 1981, "Inborn resistance of mice to orthomyxoviruses." Curr. Top. Microbiol. Immunol 92:25-52.

Haller et al., 1998, "Mx Proteins: Mediators of Innate Resistance to RNA Viruses", Rev. Sci. Tech. Off. Int. Epiz., 17(1):220-230.

Hamzawi et al., 1981, "Antigenicity in hamsters of inactivated vaccines prepared from recombinant influenza viruses." J Hyg (Lond). 87(3):453-64. (Abstract only cited).

Hatada E et al., 1992, "Binding of influenza A virus NS1 protein to dsRNA in vitro", J Gen Virol. Dec.;73 ( Pt 12):3325-9.

He et al., 1997, "The 34.5 Protein of Herpes Simplex Virus I Complexes With Protein Phosphatase 1α to Dephosphorylate the α subunit of the eukaryotic translation initiation factor 2 and preclude the shutoff of protein synthesis by double stranded RNA-activated protein kinase", Proc. Natl. Acad. Sci. USA, 94:843-848.

Hoffmann et al., 2000, "A DNA transfection system for generation of influenza A virus from eight plasmids," Proc. Natl. Acad. Sci. U. S. A. 97(11):6108-13.

Karasin et al., 2000, "Genetic characterization of an H1N2 influenza virus isolated from a pig in Indiana." J. Clin. Microbiol. 38:2453-2456.

Karasin et al., 2000, "Genetic characterization of H3N2 influenza viruses isolated from pigs in North America, 1977-1999: evidence for wholly human and reassortant virus genotypes." Virus Res. 68:71-85.

Karasin et al., 2000, "Isolation and characterization of H4N6 avian influenza viruses from pigs with pneumonia in Canada." J biol 74:9322-9327.

Karasin et al., 2002, "Genetic characterization of H1N2 influenza A viruses isolated from pigs throughout the United States. "J. Clin. Microbiol. 40:1073-9.

Katinger et al., 1997, "Attenuated influenza virus as a vector for mucosal immunization against HIV-1.", Vaccine 97: 315-319.

Kida et al., 1994, "Potential for transmission of avian influenza viruses to pigs." J. Gen Virol. 75:2183-8.

Kochs et al., 2007, Multiple anti-interferon actions of the influenza A virus NS1 protein. J Virol. Jul.;81(13):7011-21.

Komatsu et al., 2000, "Sendai Virus Blocks Alpha Interferon Signaling to Signal Transducers and Activators of Transcription", J. Virology, 74(5): 2477-2480.

Krug and Soeiro, 1975, "Studies on the intranuclear localization of influenza virus-specific proteins", Virology 64:378-87.

Krug, 1995, "Chapter 8. Unique Functions of the NS1 Protein" in *Textbook of Influenza*, Nicholson et al. (eds.), pp. 82-92.

Krystal M, et al., 1983, "Sequential mutations in the NS genes of influenza virus field strains." J Virol 45(2):547-54.

Kuwano et al., 1988, "HA2 subunit of influenza A H1 and H2 subtype viruses induces a protective cross-reactive cytotoxic T lymphocyte response.", J Immunol. Feb. 15;140(4):1264-8.

Kuwano, K et al., 1990, "Cross-reactive protection against influenza A virus infections by an NS1-specific CTL clone." Virology. Sep. ;178(1):174-9.

Lamb & Choppin, 1983, "The gene structure and replication of influenza virus." Annual Rev Biochem 52:467-506.

Landolt et al., 2003, "Comparison of the Pathogenesis of Two Genetically Different H3N2 Influenza A Viruses in Pigs.": J Clin Microb. 41(5):1936-1941.

Lapidus, 1969, "Purification and Concentration of Influenza Types A and B by Chromatography on Calcium Phosphate." Appl. Microb 17(4):504-506.

Lewis, 1985, Induction of anti-viral activity and specific enzymes in cell-lines derived from interferon-resistant, thymidine kinase deficient mouse L-929 cells, Prog Clin Biol Res 202:325-332; p. 325.

Li X and Palese P, 1994, "Characterization of the polyadenylation signal of influenza virus RNA", J Virol. Feb;8(2):1245-9.

Li X and Palese P, 1992, "Mutational analysis of the promoter required for influenza virus virion RNA synthesis", J Virol. Jul. ;66(7):4331-8.

Lo, 1983, "Transformation by iontophoretic microinjection of DNA: multiple integrations without tandem insertions." Mol. Cell. Biol. 3:1803.

Loh et al., 1994, Mutant cell lines unresponsive to alpha/beta and gamma interferon are defective in tyrosine phosphorylation of ISGF-3 alpha components, Mol. Cell. Biol. 14:2170-2179.

Lu Y et al., 1995, "Binding of the influenza virus NS1 protein to double-stranded RNA inhibits the activation of the protein kinase that phosphorylates the eIF-2 translation initiation factor", Virology. Dec. 1;214(1):222-8.

Lu Y et al., 1994, "The influenza virus NS1 protein: a novel inhibitor of pre-mRNA splicing", Genes Dev. Aug. 1;8(15):1817-28.

Lucas WT, et al., 1988, "Characterization of a unique protein produced by influenza A virus recovered from a long-term persistent infection." Virology. 166(2):620-3. (Abstract only cited).

Lunn et al., 2001, "Safety, efficacy, and immunogenicity of a modified-live equine influenza virus vaccine in ponies after induction of exercise-induced immunosuppression." J. Am Vet. Med Assoc. 218:900-906.

Luo GX et al., 1991, "The polyadenylation signal of influenza virus RNA involves a stretch of uridines followed by the RNA duplex of the panhandle structure", J Virol. Jun.;65(6):2861-7.

Luytjes W et al., "Amplification, expression, and packaging of foreign gene by influenza virus", Cell. Dec. 22, 1989;59(6):1107-13.

Maassab and Deborde, "Characterization of an influenza A host range mutant.", Virology. Oct. 30, 1983;130(2):342-50.

Maramorosh, K and Koprowski, H. 1967. *Methods in Virology* vol. 1. Ch 6. New York: Academic Press. 178-216.

Marcus et al., 1994, Interferon induction: regulation by both virus and cell. Hokkaido Igaku Zasshi. Nov.;69(6): 1320-1331.

Marion RM et al., 1997, "The N-terminal half of influeza virus NS1 protein is fully active both in mRNA nuclear retention and enhancement of translation", in *Emergence and Re-emergence of Negative Strand Viruses, Tenth International Conference on Negative Strand Viruses*. Dublin, Ireland. Abstract No. 240, p. 170.

Marion RM et al., 1997, "The N-terminal half of the influenza virus NS1 protein is sufficient for nuclear retention of mRNA and enhancement of viral mRNA translation", Nucleic Acids Res. Nov. 1;25(21):4271-7.

Mebatsion et al, 2001, "A recombinant Newcastle disease virus with low-level V protein expression is immunogenic and lacks pathogenicity for chicken embryos." J Virol. Jan.;75(1):420-8.

Meraz MA et al., 1996, "Targeted disruption of the Stat1 gene in mice reveals unexpected physiologic specificity in the JAK-STAT signaling pathway", Cell. Feb. 9;84(3):431-42.

Mibayashi et al., 2007, "Inhibition of retinoic acid-inducible gene I-mediated induction of beta interferon by the NS1 protein of influenza A virus." J Virol. Jan.;81(2):514-24.

MMWR Weekly, Progress Toward Poliomyelitis Eradication—Nigeria, 2005-2006, Mar. 30, 2007, vol. 56(12):278-281.

Morahan et al., 1970, "Age-related cellular resistance of the chicken embryo to viral infections. I. Interferon and natural resistance to myxoviruses and vesicular stomatitis virus." J Infect Dis. Jun.;121(6):615-23.

Morley et al., 1999, "Efficacy of a commercial vaccine for preventing disease caused by influenza virus infection in horses." J. Am J. vet. Med Assoc. 215:61-66.

Mosca JD et al., 1986, "Transcriptional and posttranscriptional regulation of exogenous human beta interferon gene in simian cells defective in interferon synthesis", Mol Cell Biol. Jun.;6(6):2279-83.

Mumford et al., 1998, "Monitoring and detection of acute viral respiratory tract disease in horses." J. Am Vet. Med Assoc. 21:385-390.

Kingsbury, 1991, "Orthomyxoviridae and their replication" in *Fields Virology*, Lippincott-Raven P.A., pp. 527-541.

Muster T et al., 1991, "An influenza A virus containing influenza B virus 5' and 3' noncoding regions on the neuraminidase gene is attenuated in mice", Proc Natl Acad Sci U S A. Jun. 15;88(12):5177-81.

Mwau et al. 2003, A review of vaccines for HIV prevention. J. Gene. Med. 5:3-10.

Naniche et al., 2000, "Evasion of Host Defenses by Measles Virus: Wild Type Measles Virus Infection Interferes with Induction of Alpha/Beta Interferon Production", J. Virology, 74(16): 7478-7484.

Nelson et al., 1998, "Local and systemic isotype-specific antibody responses to equine influenza virus infection versus conventional vaccination." Vaccine 16:1306-1313.

Nemeroff ME et al., 1998, "Influenza virus NS1 protein interacts with the cellular 30 kDa subunit of CPSF and inhibits 3' end formation of cellular pre-mRNAs", Mol Cell. Jun.;1(7):991-1000.

Nemeroff ME et al., 1997, "Unique interactions of the influenza virus NS 1 protein with host cell nuclear functions", in *Emergence and Re-emergence of Negative Strand Viruses, Tenth International Conference on Negative Strand Viruses.*, Dublin Ireland. Abstract No. 229, p. 164.

Neumann et al., 1999, "Generation of influenza A viruses entirely from cloned cDNAs." Proc. Natl. Acad Sci USA 96:9345-9350.
Norton GP et al., 1987, "Infectious influenza A and B virus variants with long carboxyl terminal deletions in the NS1 polypeptides", Virology. Feb.;156(2):204-13.
Olsen et al., 2000, "Virologic and serologic surveillance for human, swine and avian influenza virus infections among pigs in the north-central United States." Arch Virol 145:1399-419.
Olsen, 2002, "The emergence of novel swine influenza viruses in North America," Virus Res. 85(2):199-210.
Orkin et al. 1995, "Report and recommendations of the panel to assess the N1H investment in research on gene therapy."
Palese et al., 1999, "Learning from our foes: a novel vaccine concept for influenza virus." Arch Virol Suppl.;15:131-8.
Park et al. Newcastle disease virus (NDV)-based assay demonstrates interferon-antagonist activity for the NDV V protein and the Nipah virus V, W, and C proteins. J Virol. Jan. 2003;77(2):1501-11.
Park et al., 2003, "Newcastle disease virus V protein is a determinant of host range restriction." J Virol. 70:9522-9532.
Park YW and Katze MG, "Translational control by influenza virus. Identification of cis-acting sequences and trans-acting factors which may regulate selective viral mRNA translation", J Biol Chem. Nov. 24, 1995;270(47):28433-9.
Parvin JD et al., "Nonsense mutations affecting the lengths of the NS1 nonstructural proteins of influenza A virus isolates", Virology. Jul. 30, 1983;128(2):512-7.
Piccone Me et al., "Mutational analysis of the influenza virus vRNA promoter", Virus Res. May 1993;28(2):99-112.
Pleschka S et al., "A plasmid-based reverse genetics system for influenza A virus", J Virol. Jun. 1996;70(6):4188-92.
Qian et al., 1995, "An amino-terminal polypeptide fragment of the influenza virus NS1 protein possesses specific RNA-binding activity and largely helical backbone structure." RNA 1:948-956.
Qin XQ et al., "Interferon-beta gene therapy inhibits tumor formation and causes regression of established tumors in immune-deficient mice", Proc Natl Acad Sci U S A. Nov. 24, 1998;95(24):14411-6.
Qiu Y and Krug RM, "The influenza virus NS1 protein is a poly(A)-binding protein that inhibits nuclear export of mRNAs containing poly(A)", J Virol. Apr. 1994;68(4):2425-32.
Qiu Y et al., "The influenza virus NS1 protein binds to a specific region in human U6 snRNA and inhibits U6-U2 and U6-U4 snRNA interactions during splicing", RNA. May 1995;1(3):304-16.
Quinlivan et al., Attenuation of equine influenza viruses through truncations of the NS1 protein. J Virol. Jul. 2005;79(13):8431-9.
Qureshi et al., 1996, Function of Stat2 protein in transcriptional activation by alpha interferon, Mol. Cell. Biol. 16:288-293.
Reed et al., 1938, "A simple Method of estimating fifty percent endpoints." Am J. Hyg 27(3):493-497.
Restifo et al., 1998, "The promise of nucleic acid vaccines." Virology 249:89-97.
Richt et al., 2003, "Attenuation of an H3N2 swine Influenza virus utilizing a reverse genetics approach," 4th Intl. Symposium on Emerging and Re-emerging Pig Diseases, pp. 264-265.
Richt et al., Vaccination of pigs against swine influenza viruses by using an NS1-truncated modified live-virus vaccine. J Virol. Nov. 2006;80(22):11009-18.
Robert-Guroff et al. 1998, Vaccine protection against a heterologous, non-syncytium-inducing, primary human immunodeficiency virus. J. Virol. 72:10275-10280.
Schlender et al., 2000, "Bovine Respiratory Syncytial Virus Nonstructural Proteins NS1 and NS2 Cooperatively Antagonize Alpha/Beta Interferon-Induced Antiviral Response", J. of Virology 74(18):8234-8242.
Scholtissek, 1990, "Pigs as 'mixing vessels' for the creation of new pandemic influenza A viruses." Med Principles Pract 2:65-71.
Scholtissek, 1994, "Source for influenza pandemics." Eur J. Epidemiol 10:455-8.
Schuepbach et al., Early antiviral antibody response after immunization with viral oncolysate: a powerful prognostic marker for acute myelogenous leukemia remission patients. Blood. Sep. 1983;62(3):616-21.
Sekellick MJ et al., "Development of the interferon system. I. In chicken cells development in ovo continues on time in vitro", In Vitro Cell Dev Biol. Oct. 1990;26(10):997-1003.
Sekellick MJ et al., "Interferon induction by viruses. XIV. Development of interferon inducibility and its inhibition in chick embryo cells "aged" in vitro", J Interferon Res. 1985 Fall;5(4):651-67.
Seno et al., 1990, "Enhancing Effect of Centrifugation on Isolation of Influenza Virus from Clinical Specimens." J Clin. Microb. 28(7):1669-1670.
Shaw et al., "Immunologic studies on the influenza A virus nonstructural protein NS1.", J Exp Med. Jul. 1, 1982;156(1):243-54.
Shaw et al., 1996, "Nucleocapsid protein alone is sufficient for the generation of influenza transfectants" in *Options for the Control of Influenza III*, Brown (eds.), Hampson Webster (Elsevier Science) pp. 433-436.
Shope, 1931, "Swine Influenza: III. Filtration Experiments and Etiology." J. Exp. Med. 54:373-385.
Shu et al., 1994, "Evidence for interspecies transmission and reassortment of influenza A viruses in pigs in southern China." Virol. 202:825-33.
Snyder et al., "A 36 nucleotide deletion mutation in the coding region of the NS1 gene of an influenza A virus RNA segment 8 specifies a temperature-dependent host range phenotype.", Virus Res. Jan. 1990;15(1):69-83.
Soboll et al., 2003, "Mucosal co-administration of cholera toxin and influenza virus hemagglutinin-DNA in ponies generates a local IgA response." Vaccine 21:3081-3092.
Solorzano et al., 2005, "Mutations in the NS1 protein of swine influenza virus impair anti-interferon activity and confer attenuation in pigs." J Virol. 79(12):7535-43.
Sovinova et al., 1958, "Isolation of a virus causing respiratory disease in horses." Acta Virol 2:52-61.
Stark et al., 1998, "How Cells Respond to Interferons", Annu.Rev. Biochem. 67:227-264.
Stojdl et al., 2003, "VSV strains with defects in their ability to shutdown innate immunity are potent systemic anti-cancer agents" Cancer Cell 4:263-275.
Talon et al., 2000, "Activation of Interferon Regulatory Factor 3 Is Inhibited by the Influenza A Virus NS1 Protein", J. of Virology, 74(17): 7989-7996.
Tobita K et al., "Nucleotide sequence and some biological properties of the NS gene of a newly isolated influenza B virus mutant which has a long carboxyl terminal deletion in the NS1 protein", Virology. Jan. 1990;174(1):314-9.
Townsend, 2001, "Efficacy of a cold-adapted, intranasal, equine influenza vaccine: challenge trials." Equine Vet J. 33:637-643.
Vandemark and Batzing, 1986, "The microbes: an introduction to their nature and importance", The Microbes. pp. 670-680.
Van Der Putten et al., 1985, "Efficient insertion of genes into the mouse germ line via retroviral vectors." Proc. Natl Acad Sci 82:6148-6152.
Verma et al., 1997, "Gene therapy—promises, problems and prospects." Nature. Sep 18;389(6648): 239-42.
Veselov et al., 1984, "Isolation of preparative amounts of influenza virus hemagglutinin by an affinity chromatographic method." Vopr Virusol 29(1):93-7 Abstract in English.
Waddell et al., "A new influenza virus associated with Equine Respiratory Disease." 1963, J Am Vet Med. Assoc. 143:587-590.
Wang et al., 2002, "Functional replacement of the carboxy-terminal two-thirds of the influenza A virus NS1 protein with short heterologous dimerization domains." J Virol. Dec.;76(24):12951-62.
Wang et al., 2000, "Influenza A Virus NS1 Protein Prevents Activation of NF-KB and Induction of Alpha/Beta Interferon", J. of Virology 74(24): 11566-11573.
Weaver BK et al., 1998, "Interferon regulatory factor 3 and CREB-binding protein/p300 are subunits of double-stranded RNA-activated transcription factor DRAF1", Mol Cell Biol. Mar.;18(3):1359-68.
Webby et al., 2000, "Evolution of swine H3N2 influenza viruses in the United States." J. Virol 74:8243-51.
Webby et al., 2001, "Emergence of Influenza A Viruses," Philos Trans R Soc Lond B Biol Sci 356:1817-28.
Webster, 1993, "Are equine 1 influenza viruses still present in horses?" Equine vet. 25:537-538.

Wong et al., 1997, Interferon-resistant human melanoma cells are deficient in ISGF3 components, STAT1, STAT2, and p48-1SGF3gamma, J.Biol. Chem. 272:28779-28785.

Wuethrich, 2003, "Chasing the fickle swine flu," Science 299(5612):1502-5.

Yang et al., 1998, STAT3 complements defects in an interferon-resistant cell line : Evidence for an essential role for STAT3 in interferon signaling and biological activities, Proc. Natl. Acad. Sci. USA 95:5568-5572.

Yannarell DA, Hjorth RN. , 1997, Factors affecting the yield of cold-adapted influenza virus vaccine. J Virol Methods. 64(2):161-9.

Yoshida T et al., "Characterization of the RNA associated with influenza A cytoplasmic inclusions and the interaction of NS1 protein with RNA.", Virology. Apr. 15, 1981;110(1):87-97.

Young et al., 2000, "Paramyxoviridae Use Distinct Virus Specific Mechanisms to Circumvent the Interferon Response", Virology, 269:383-390.

Young JF et al., "Efficient expression of influenza virus NS1 nonstructural proteins in *Escherichia coli*.", Proc Natl Acad Sci U S A. Oct. 1983;80(19):6105-9.

Zhou, 1999, "Genetic reassortment of avian, swine, and human influenza A viruses in American pigs", J. Virol 73:8851-6.

Zhou, 2000, "Emergence of H3N2 reassortant influenza A viruses in North American pigs." Vet Microbiol 74:47-58.

International Search Report PCT/US99/13144, dated Oct. 21, 1999.
International Search Report PCT/US99/13142, dated Oct. 21, 1999.
International Search Report PCT/US99/13139, dated Oct. 28, 1999.
International Search Report PCT/US05/19382, dated Oct. 25, 2006.
International Search Report PCT/US05/19383, dated Nov. 8, 2006.
International Preliminary Examination Report PCT/US99/13142, dated Aug. 9, 2000.
International Preliminary Examination Report PCT/US99/13144, dated Nov. 28, 2000.
Supplementary Partial European Search Report EP 99 92 7440, dated Jul. 17, 2001.
International Preliminary Report on Patentability PCT/US01/11543, dated Mar. 5, 2002.
International Preliminary Report on Patentability PCT/US05/019382, dated Dec. 28, 2006.
International Preliminary Report on Patentability PCT/US05/019383, dated Aug. 21, 2007.
Supplementary European Search Report EP 99 92 7443, dated Oct. 30, 2002.
Supplementary Partial European Search Report EP 99 92 7445, dated Nov. 3, 2004.
Office Action dated Oct. 4, 1999 of U.S. Appl. No. 09/332,286.
Office Action dated May 23, 2000 of U.S. Appl. No. 09/332,286.
Office Action dated Dec. 6, 2000 of U.S. Appl. No. 09/332,286.
Office Action dated May 8, 2001 of U.S. Appl. No. 09/332,286.
Office Action dated Feb. 13, 2002 of U.S. Appl. No. 09/332,286.
Office Action dated Nov. 22, 2000 of U.S. Appl. No. 09/332,287.
Office Action dated Mar. 14, 2001 of U.S. Appl. No. 09/332,287.
Office Action dated Oct. 25, 2001 of U.S. Appl. No. 09/332,287.
Office Action dated Feb. 22, 2001 for U.S. Appl. No. 09/332,288.
Office Action dated Nov. 7, 2001 for U.S. Appl. No. 09/332,288.
Office Action dated Jun. 4, 2002 for U.S. Appl. No. 09/332,288.
Office Action dated Feb. 21, 2003 of U.S. Appl. No. 09/332,288.
Written Opinion PCT/US99/13142, dated May 3, 2000.
Written Opinion PCT/US99/13139, dated Jun. 14, 2000.
Written Opinion PCT/US05/19383, dated Oct. 11, 2006.
Written Opinion PCT/US05/19382, dated Sep. 28, 2006.

Briedis et al., 1981, "Influenza B virus genome: sequences and structural organization of RNA segment 8 and the mRNAs coding for the $NS_1$ and $NS_2$ proteins." J Virol. 42(1):186-93.

Buonagurio et al. 1984, "Analysis of an influenza A virus mutant with a deletion in the NS segment," J. Virol. 49:418-425.

Chambers et al., 2009, "Influenza A viruses with truncated NS1 as modified live virus vaccines: Pilot studies of safety and efficacy in horses," Equine Veterinary Journal 41:87-92.

Clemens et al., 1997, "The Double Stranded RNA-Dependent Protein Kinase PKR: Structure and Function", in Journal of Interferon and Cytokine Research; 17:503-24.

Floyd-Smith et al., 1981, "Interferon Action: RNA Cleavage Pattern of a (2'-5') Oligoadenylate-Dependent Endonuclease," Science; 212:1030-2.

Holmquist et al., 1979, "Affinity chromatography of influenza virus on immobilized alpha and beta-ketosides of neraminic acid derivatives" in Acta Pathol Microb. Scand [B]; 87B(2):129-35 (Abstract Only).

Krishnan et al., 1997, "Kinase-deficient forms of Jak1 and Tyk2 inhibit interferon alpha signaling in a dominant manner." in Eur. J. Biochem.; 247:298-305.

Li & Rhode, 1990, "Mutation of lysine 405 to serine in the parvovirus H-1 NS1 abolishes its functions for viral DNA replication, late promoter trans activation, and cytotoxicity," J. Virol 10:4654-4660.

Lucas WT, et al., 1988, "Characterization of a unique protein produced by influenza A virus recovered from a long-term persistent infection." Virology. 166(2):620-3 (abstract previously submitted as reference C117 in Information Disclosure Statement filed Aug. 22, 2008).

Murphy et al., 1996, "Orthomyxoviruses" in Fields Virology, Lippincott-Raven P.A., pp. 97-144.

Perry et al., 1993, "Transgenesis in chickens" Transgenic Res. 2(3):125-33.

Restifo et al., 1998, "Transfectant influenza A viruses are effective recombinant immunogens in the treatment of experimental cancer.". Virology 249:89-97.

Richt & Garcia-Sastre, 2009, "Attenuated influenza virus vaccines with modified NS1 proteins," Current Topics in Microbiology and Immunology v333:177-195.

Rui et al, 2004; "Progress of swine influenza virus," Progress in Veterinary Medicine 25:25-28 (in Chinese with English Abstract).

Sang, 1994, "Transgenic chickens—methods and potential applications", Trends Biotechnol. 12(10):415-20.

Shuman, 1991, "Production of transgenic birds", Expertentia. 47(9):897-905.

Stern, 1996, "Chick stem cells", Curr Top Microbiol Immunol. 212:195-206.

Taniguchi et al., 1996, "Nondefective rotavirus mutants with an NSPI gene which has a deletion of 500 nucleotides, including a cysteine-rich zinc finger motif-encoding region (nucleotides 156 to 248), or which has a nonsense codon at nucleotides 153 to 155," Journal of Virology 70:4125-4130.

Webster & Thomas, 1993, "Efficacy of equine influenza vaccines or protection against A/Equine/Jilin/89 (H3N8)—a new equine influenza virus," Vaccine 11:987-993.

Wressnigg et al., 2009, "Influenza B mutant viruses with truncated NS1 proteins grow effciently in Vero cells and are immunogenic in mice," Journal of General Virology. 90:366-374.

Zhu et al., 2008, "A naturally occurring deletion in its NS1 gene contributes to the attenuation of an H5N1 swine influenza virus in chickens," Journal of Virology 82:220-228.

International Preliminary Examination Report PCT/US99/13139, dated Sep. 12, 2000.
European patent application No. 99927445: Response to Nov. 14, 2007 Communication pursuant to Article 96(2) EPC, dated May 26, 2008.
European patent application No. 99927445: Communication pursuant to Article 96(2) EPC, dated Nov. 14, 2007.
European patent application No. 99927445: Response to May 26, 2006 Communication pursuant to Article 96(2) EPC, dated Dec. 5, 2006.
European patent application No. 99927445: Communication pursuant to Article 96(2) EPC, dated May 26, 2006.
European patent application No. 99927445: Response to Mar. 21, 2005 Communication pursuant to Article 96(2) EPC, dated Sep. 30, 2005.
European patent application No. 99927445: Communication pursuant to Article 96(2) EPC, dated Mar. 21, 2005.
European patent application No. 99927445: European Search Report, dated Nov. 11, 2004.
Written Opinion PCT/US99/13144, dated Jul. 25, 2000.
U.S. Appl. No. 09/724,419: Notice of Allowance, dated May 27, 2004.

U.S. Appl. No. 09/724,419: Amendment Under 37 C.F.R. § 1.116, dated Feb. 26, 2004.
U.S. Appl. No. 09/724,419: Office Action, dated Aug. 26, 2003.
U.S. Appl. No. 09/724,419: Amendment Under 37 C.F.R. § 1.111, dated Jun. 11, 2003.
U.S. Appl. No. 09/724,419: Office Action, dated Feb. 11, 2003.
U.S. Appl. No. 09/724,419: Amendment Under 37 C.F.R. § 1.111, dated Dec. 31, 2002.
U.S. Appl. No. 09/724,419: Office Action, dated Jul. 2, 2002.
U.S. Appl. No. 09/724,419: Amendment Under 37 C.F.R. § 1.111, dated Apr. 19, 2002.
U.S. Appl. No. 09/724,419: Office Action, dated Dec. 19, 2001.
U.S. Appl. No. 09/332,286: Notice of Allowance dated Jan. 17, 2003.
U.S. Appl. No. 09/332,286: Amendment Under 37 C.F.R. § 1.116, dated Aug. 12, 2002.
U.S. Appl. No. 09/332,286: Amendment Under 37 C.F.R. § 1.111, dated Nov. 8, 2001.
U.S. Appl. No. 09/332,286: Amendment Under 37 C.F.R. § 1.116, dated Nov. 24, 2000.
U.S. Appl. No. 09/332,286: Amendment Under 37 C.F.R. § 1.111, dated Mar. 6, 2000.
U.S. Appl. No. 09/332,287: Notice of Allowance, dated May 28, 2002.
U.S. Appl. No. 09/332,287: Office Action, dated Apr. 15, 2002.
U.S. Appl. No. 09/332,287: Supplemental Amendment Under 37 C.F.R. § 1.116, dated Apr. 12, 2002.
U.S. Appl. No. 09/332,287: Supplemental Amendment Under 37 C.F.R. § 1.116, dated Apr. 10, 2002.
U.S. Appl. No. 09/332,287: Amendment Under 37 C.F.R. § 1.116, dated Mar. 25, 2002.
U.S. Appl. No. 09/332,287: Amendment Under 37 C.F.R. § 1.111, dated Sep. 14, 2001.
U.S. Appl. No. 10/314,569: Notice of Allowance, dated Oct. 20, 2004.
U.S. Appl. No. 10/314,569: Amendment Under 37 C.F.R. § 1.116, dated Sep. 17, 2004.
U.S. Appl. No. 10/314,569: Office Action dated Apr. 20, 2004.
U.S. Appl. No. 10/314,569: Amendment Under 37 C.F.R. § 1.111, dated Jan. 26, 2004.
U.S. Appl. No. 10/314,569: Office Action dated Aug. 26, 2003.
U.S. Appl. No. 10/945,718: Notice of Allowance, dated Oct. 16, 2008.
U.S. Appl. No. 10/945,718: Amendment Under 37 C.F.R. § 1.111, dated Apr. 7, 2008.
U.S. Appl. No. 10/945,718: Office Action, dated Oct. 5, 2007.
U.S. Appl. No. 10/945,718: Amendment Under 37 C.F.R. § 1.111, dated Nov. 28, 2006.
U.S. Appl. No. 10/945,718: Office Action, dated Aug. 29, 2006.
U.S. Appl. No. 10/945,718: Reply Under 37 C.F.R. § 1.111, dated May 10, 2006.
U.S. Appl. No. 10/945,718: Office Action, dated Jan. 10, 2006.
U.S. Appl. No. 10/945,718: Reply Under 37 C.F.R. § 1.111, dated Oct. 24, 2005.
U.S. Appl. No. 10/945,718: Office Action, dated Jun. 22, 2005.
U.S. Appl. No. 09/332,288: Notice of Allowance, dated Aug. 6, 2003.
U.S. Appl. No. 09/332,288: Amendment Under 37 C.F.R. § 1.116, dated Jul. 21, 2003.
U.S. Appl. No. 09/332,288: Amendment Under 37 C.F.R. § 1.111, dated Dec. 4, 2002.
U.S. Appl. No. 09/332,288: Examiner's Amendment, dated May 31, 2002.
U.S. Appl. No. 09/332,288: Amendment Under 37 C.F.R. § 1.111, dated Mar. 7, 2002.
U.S. Appl. No. 09/332,288: Amendment Under 37 C.F.R. § 1.111, dated Aug. 22, 2001.
U.S. Appl. No. 10/713,732, Notice of Allowance, dated Mar. 13, 2009.
U.S. Appl. No. 10/713,732, Amendment Under 37 C.F.R. § 1.111, dated Dec. 2, 2008.
U.S. Appl. No. 10/713,732, Office Action dated Jul. 2, 2008.
U.S. Appl. No. 10/713,732, Amendment Under 37 C.F.R. § 1.111, dated Apr. 11, 2008.
U.S. Appl. No. 10/713,732, Office Action dated Oct. 19, 2007.
U.S. Appl. No. 10/713,732, Office Action dated May 15, 2007.
U.S. Appl. No. 10/713,732, Amendment Under 37 C.F.R. § 1.111, dated Mar. 23, 2007.
U.S. Appl. No. 10/713,732, Office Action dated Oct. 24, 2006.
U.S. Appl. No. 11/628,292: Preliminary Amendment Under 37 C.F.R. § 1.115, dated Nov. 30, 2006.
U.S. Appl. No. 11/628,292: Second Preliminary Amendment Under 37 C.F.R. § 1.115, dated Feb. 6, 2008.
U.S. Appl. No. 11/628,292: Restriction Requirement, dated Dec. 17, 2008.
U.S. Appl. No. 11/628,292: Response to Restriction Requirement Under 37 C.F.R. § 1.143, dated Feb. 17, 2009.
U.S. Appl. No. 11/628,292: Non-Final rejection, dated May 21, 2009.
U.S. Appl. No. 11/628,292: Response to Non-Final rejection Under 37 C.F.R. § 1.111, Nov. 23, 2009.
GenBank sequence No. AY855345.1, Mar. 12, 2005.
Supplementary European Search Report, European Patent Application No. EP 05856779.
Ito, T., J. N. S. S. Couceiro, S. Kelm, L. G. Baum, S. Krauss, M. R. Castrucci, I. Donatelli, H. Kida, J. C. Paulson, R. G. Webster, and Y. Kawaoka. 1998. Molecular basis for the generation in pigs of influenza A viruses with pandemic potential. J. Virol. 72:7367-7373.
Khiabanian et al., 2009, "Reassortment patterns in swine influenza viruses," PLoS One, 4:e7366.
Li H et al., 2004, "Interspecies transmission and molecular evolution of swine influenza virus," *Chinese Journal of Veterinary Science*, 24:304-306 (with English-language summary).
Pensaert M, Ottis K, Vandeputte J, Kaplan M M, Bachmann P A. Evidence of natural transmission of influenza A virus from wild ducks to swine and its potential importance for man. Bull W H O. 1996;59:75-78.
Perez et al., 2003, "Land-based birds as potential disseminators of avian/mammalian reassortant influenza A viruses," *Avian Diseases* 47:1114-1117.
Rogers G N, Paulson J C. Receptor determinants of human and animal influenza virus isolates: differences in receptor specificity of the H3 hemagglutinin based on species of origin. Virology. 1983;127:361-373.
Scholtissek et al., 1998, "Influenza in pigs and their role as the intermediate host," Ch. 13 in K. G. Nicholson, R. G. Webster, A. J. Hay (ed.), *Textbook of influenza*, Blackwell Science, Oxford, United Kingdom, pp. 137-145.
Schultz U, Fitch W M, Ludwig S, Mandler J, Scholtissek C. Evolution of pig influenza viruses. Virology. 1991;183:61-73.
Shope Re, 1951, "The provocation of masked swine influenza virus by infection with human influenza virus," Tijdschrift Voor Diergeneeskunde 76:414-420.
Vincent Al et al., 2007, "Efficacy of intranasal administration of a truncated NS1 modified live influenza virus vaccine in swine," Vaccine 25:7999-8009.
U.S. Appl. No. 11/628,292, Amendment dated Nov. 23, 2009.
U.S. Appl. No. 11/628,292, Non-Final rejection dated Feb. 19, 2010.
U.S. Appl. No. 11/628,292, Amendment dated Aug. 12, 2010.
U.S. Appl. No. 11/628,292, Non-Final rejection dated Nov. 15, 2010.
U.S. Appl. No. 11/628,292, Amendment dated Apr. 15, 2011.
U.S. Appl. No. 11/628,292, Notice of Allowance and Examiner Interview Summary Record, dated Jul. 1, 2011.
U.S. Appl. No. 12/148,798; Office Action dated Nov. 29, 2010.
U.S. Appl. No. 12/148,798; Amendment Under 37 C.F.R. § 1.111 dated May 27, 2011.
U.S. Appl. No. 12/364,243, Office Action dated Mar. 17, 2010.
U.S. Appl. No. 12/364,243; Amendment Under 37 C.F.R. § 1.111, dated Aug. 17, 2010.
U.S. Appl. No. 12/364,243; Correction of Amendment Under 37 C.F.R. § 1.111 filed on Aug. 17, 2010, dated Nov. 29, 2010.
U.S. Appl. No. 12/364,243; Office Action dated Feb. 16, 2011.
U.S. Appl. No. 12/364,243; Reply Under 37 C.F.R. § 1.114, dated Jul. 18, 2011.
European Patent Application No. 05 856 779.3; Communication pursuant to Article 94(3) EPC, dated Oct. 6, 2010.

European Patent Application No. 05 856 779.3; Reply to Communication pursuant to Article 94(3) EPC, dated Apr. 15, 2011.

European Patent Application No. 05 856 779.3; Communication pursuant to Article 94(3) EPC, dated Apr. 29, 2011.

European Patent Application No. 05 856 779.3; Reply Communication pursuant to Article 94(3) EPC, dated May 11, 2011.

European Patent Application No. 05 856 778.5, Communication pursuant to Article 94(3) EPC, dated Apr. 7, 2010.

European Patent Application No. 05 856 778.5; Response to Apr. 17, 2010 Communication pursuant to Article 94(3) EPC, dated Oct. 15, 2010.

European Patent Application No. 05 856 778.5; Communication pursuant to Article 94(3) EPC, dated Jun. 28, 2011.

Chinese Patent Application No. 200580026048.9, Translation of Second Office Action dated Apr. 2, 2010.

* cited by examiner

SEQUENCE LISTING

```
<160> NUMBER OF SEQ ID NOS: 23

<210> SEQ ID NO 1
<211> LENGTH: 29
<212> TYPE: DNA
<213> ORGANISM: Artificial Sequence
<220> FEATURE:
<223> OTHER INFORMATION: primer

<400> SEQUENCE: 1
tttttttttt tttttttttt tttttttagc                              29

<210> SEQ ID NO 2
<211> LENGTH: 15
<212> TYPE: DNA
<213> ORGANISM: Artificial Sequence
<220> FEATURE:
<223> OTHER INFORMATION: primer

<400> SEQUENCE: 2
cattcctatt ccacc                                              15

<210> SEQ ID NO 3
<211> LENGTH: 15
<212> TYPE: DNA
<213> ORGANISM: Artificial Sequence
<220> FEATURE:
<223> OTHER INFORMATION: primer

<400> SEQUENCE: 3
```

```
aaagccattg cttcc                                                        15

<210> SEQ ID NO 4
<211> LENGTH: 14
<212> TYPE: DNA
<213> ORGANISM: Artificial Sequence
<220> FEATURE:
<223> OTHER INFORMATION: primer

<400> SEQUENCE: 4
ctactgtcca tgcc                                                         14

<210> SEQ ID NO 5
<211> LENGTH: 17
<212> TYPE: DNA
<213> ORGANISM: Artificial Sequence
<220> FEATURE:
<223> OTHER INFORMATION: primer

<400> SEQUENCE: 5
catatgggta gcaattg                                                      17

<210> SEQ ID NO 6
<211> LENGTH: 16
<212> TYPE: DNA
<213> ORGANISM: Artificial Sequence
<220> FEATURE:
<223> OTHER INFORMATION: primer

<400> SEQUENCE: 6
gattcctccc accatc                                                       16

<210> SEQ ID NO 7
<211> LENGTH: 16
<212> TYPE: DNA
<213> ORGANISM: Artificial Sequence
<220> FEATURE:
<223> OTHER INFORMATION: primer

<400> SEQUENCE: 7
ggaccagtac tgttac                                                       16

<210> SEQ ID NO 8
<211> LENGTH: 13
<212> TYPE: DNA
<213> ORGANISM: Artificial Sequence
<220> FEATURE:
<223> OTHER INFORMATION: primer

<400> SEQUENCE: 8
tacgctgcag tcc                                                          13

<210> SEQ ID NO 9
<211> LENGTH: 15
<212> TYPE: DNA
<213> ORGANISM: Artificial Sequence
<220> FEATURE:
<223> OTHER INFORMATION: primer

<400> SEQUENCE: 9
cttctggtct cggcg                                                        15

<210> SEQ ID NO 10
<211> LENGTH: 28
<212> TYPE: DNA
<213> ORGANISM: Artificial Sequence
<220> FEATURE:
```

```
<223> OTHER INFORMATION: primer

<400> SEQUENCE: 10
catcgctctt ctattagtag aaacaagg                                          28

<210> SEQ ID NO 11
<211> LENGTH: 17
<212> TYPE: DNA
<213> ORGANISM: Artificial Sequence
<220> FEATURE:
<223> OTHER INFORMATION: primer

<400> SEQUENCE: 11
agcatactta ctgacag                                                      17

<210> SEQ ID NO 12
<211> LENGTH: 13
<212> TYPE: DNA
<213> ORGANISM: Artificial Sequence
<220> FEATURE:
<223> OTHER INFORMATION: primer

<400> SEQUENCE: 12
aggccatggt gtc                                                          13

<210> SEQ ID NO 13
<211> LENGTH: 15
<212> TYPE: DNA
<213> ORGANISM: Artificial Sequence
<220> FEATURE:
<223> OTHER INFORMATION: primer

<400> SEQUENCE: 13
caacctggaa cctgg                                                        15

<210> SEQ ID NO 14
<211> LENGTH: 17
<212> TYPE: DNA
<213> ORGANISM: Artificial Sequence
<220> FEATURE:
<223> OTHER INFORMATION: primer

<400> SEQUENCE: 14
caggctacaa agattgg                                                      17

<210> SEQ ID NO 15
<211> LENGTH: 12
<212> TYPE: DNA
<213> ORGANISM: Artificial Sequence
<220> FEATURE:
<223> OTHER INFORMATION: primer

<400> SEQUENCE: 15
ggcaataagg ac                                                           12

<210> SEQ ID NO 16
<211> LENGTH: 15
<212> TYPE: DNA
<213> ORGANISM: Artificial Sequence
<220> FEATURE:
<223> OTHER INFORMATION: primer

<400> SEQUENCE: 16
tcacattgcc ggttg                                                        15

<210> SEQ ID NO 17
```

```
<211> LENGTH: 13
<212> TYPE: DNA
<213> ORGANISM: Artificial Sequence
<220> FEATURE:
<223> OTHER INFORMATION: primer

<400> SEQUENCE: 17
cggatgggag tgc                                                          13

<210> SEQ ID NO 18
<211> LENGTH: 15
<212> TYPE: DNA
<213> ORGANISM: Artificial Sequence
<220> FEATURE:
<223> OTHER INFORMATION: primer

<400> SEQUENCE: 18
gtgcgacata gattg                                                        15

<210> SEQ ID NO 19
<211> LENGTH: 6
<212> TYPE: DNA
<213> ORGANISM: Artificial Sequence
<220> FEATURE:
<223> OTHER INFORMATION: primer

<400> SEQUENCE: 19 ctggaa                                                                   6

<210> SEQ ID NO 20
<211> LENGTH: 6
<212> TYPE: DNA
<213> ORGANISM: Artificial Sequence
<220> FEATURE:
<223> OTHER INFORMATION: primer

<400> SEQUENCE: 20 ctcgag                                                                   6

<210> SEQ ID NO 21
<211> LENGTH: 30
<212> TYPE: DNA
<213> ORGANISM: Artificial Sequence
<220> FEATURE:
<223> OTHER INFORMATION: primer

<400> SEQUENCE: 21
gataagtaga tcttgattaa ttaagaagga                                        30

<210> SEQ ID NO 22
<211> LENGTH: 23
<212> TYPE: DNA
<213> ORGANISM: Artificial Sequence
<220> FEATURE:
<223> OTHER INFORMATION: primer

<400> SEQUENCE: 22
atgtcatgat taattaagaa gga                                               23

<210> SEQ ID NO 23
<211> LENGTH: 26
<212> TYPE: DNA
```

```
<213> ORGANISM: Artificial Sequence
<220> FEATURE:
<223> OTHER INFORMATION: primer

<400> SEQUENCE: 23
gaatcataag ctttaattaa gaagga                                              26
```

GENETICALLY ENGINEERED EQUINE INFLUENZA VIRUS AND USES THEREOF

This application is a national stage application under 35 U.S.C. §371 of International Patent Application No. PCT/US2005/019383, filed Jun. 5, 2005, which claims the benefit of U.S. Provisional Application No. 60/653,588, filed Feb. 15, 2005, entitled "Genetically Engineered Equine Influenza Virus and Uses Thereof," each of which is incorporated by reference herein in its entirety.

This invention was made, in part, with United States Government support. The United States Government may have certain rights in this invention.

1. FIELD OF THE INVENTION

The present invention relates, in general, to attenuated equine influenza viruses having an impaired ability to antagonize the cellular interferon (IFN) response, and the use of such attenuated viruses in vaccine and pharmaceutical formulations. In particular, the invention relates to attenuated equine influenza viruses having modifications to an equine NS1 gene that diminish or eliminate the ability of the NS1 gene product to antagonize the cellular IFN response. These viruses replicate in vivo, but demonstrate decreased virulence and increased attenuation, and therefore are well suited for use in live virus vaccines and pharmaceutical formulations.

2. BACKGROUND

2.1 Influenza Virus

Virus families containing enveloped single-stranded RNA of the negative-sense genome are classified into groups having non-segmented genomes (Paramyxoviridae, Rhabdoviridae, Filoviridae and Borna Disease Virus) or those having segmented genomes (Orthomyxoviridae, Bunyaviridae and Arenaviridae). The Orthomyxoviridae family, described in detail below, and used in the examples herein, includes the viruses of influenza, types A, B and C viruses, as well as Thogoto and Dhori viruses and infectious salmon anemia virus.

The influenza virions consist of an internal ribonucleoprotein core (a helical nucleocapsid) containing the single-stranded RNA genome, and an outer lipoprotein envelope lined inside by a matrix protein (M1). The segmented genome of influenza A virus consists of eight molecules (seven for influenza C) of linear, negative polarity, single-stranded RNAs which encode eleven polypeptides, including: the RNA-dependent RNA polymerase proteins (PB2, PB1 and PA) and nucleoprotein (NP) which form the nucleocapsid; the matrix membrane proteins (M1, M2); two surface glycoproteins which project from the lipid containing envelope: hemagglutinin (HA) and neuraminidase (NA); the nonstructural protein (NS1) and nuclear export protein (NEP); and proapoptotic factor PB1-F2. Transcription and replication of the genome takes place in the nucleus and assembly occurs via budding on the plasma membrane. The viruses can reassort genes during mixed infections.

Influenza virus adsorbs via HA to sialyloligosaccharides in cell membrane glycoproteins and glycolipids. Following endocytosis of the virion, a conformational change in the HA molecule occurs within the cellular endosome which facilitates membrane fusion, thus triggering uncoating. The nucleocapsid migrates to the nucleus where viral mRNA is transcribed. Viral mRNA is transcribed by a unique mechanism in which viral endonuclease cleaves the capped 5'-terminus from cellular heterologous mRNAs which then serve as primers for transcription of viral RNA templates by the viral transcriptase. Transcripts terminate at sites 15 to 22 bases from the ends of their templates, where oligo(U) sequences act as signals for the addition of poly(A) tracts. Of the eight viral RNA molecules so produced, six are monocistronic messages that are translated directly into the proteins representing HA, NA, NP and the viral polymerase proteins, PB2, PB1 and PA. The other two transcripts undergo splicing, each yielding two mRNAs which are translated in different reading frames to produce M1, M2, NS1 and NEP. The PB1 segment encodes a second protein, the nonstructural PB1-F2 protein, by using an alternative ATG. In other words, the eight viral RNA segments code for eleven proteins: nine structural and two nonstructural. A summary of the genes of the influenza virus and their protein products is shown in Table I below.

TABLE I

INFLUENZA VIRUS GENOME RNA SEGMENTS AND CODING ASSIGNMENTS[a]

| Segment | Length[b] (Nucleotides) | Encoded Polypeptide[c] | Length[d] (Amino Acids) | Molecules Per Virion | Comments |
|---|---|---|---|---|---|
| 1 | 2341 | PB2 | 759 | 30-60 | RNA transcriptase component; host cell RNA cap binding |
| 2 | 2341 | PB1 | 757 | 30-60 | RNA transcriptase component; initiation of transcription |
|  |  | PB1-F2 | 87 |  | Proapoptotic factor |
| 3 | 2233 | PA | 716 | 30-60 | RNA transcriptase component |
| 4 | 1778 | HA | 566 | 500 | Hemagglutinin; trimer; envelope glycoprotein; mediates attachment to cells |
| 5 | 1565 | NP | 498 | 1000 | Nucleoprotein; associated with RNA; structural component of RNA transcriptase |
| 6 | 1413 | NA | 454 | 100 | Neuraminidase; tetramer; envelope glycoprotein |
| 7 | 1027 | $M_1$ | 252 | 3000 | Matrix protein; lines inside of envelope |

TABLE I-continued

INFLUENZA VIRUS GENOME RNA SEGMENTS AND CODING ASSIGNMENTS[a]

| Segment | Length[b] (Nucleotides) | Encoded Polypeptide[c] | Length[d] (Amino Acids) | Molecules Per Virion | Comments |
|---|---|---|---|---|---|
| | | $M_2$ | 96 | ? | Structural protein in plasma membrane; spliced mRNA |
| 8 | 890 | $NS_1$ | 230 | | Nonstructural protein; |
| | | NEP | 121 | ? | Nuclear export protein; spliced mRNA |

[a]Adapted from R. A. Lamb and P. W. Choppin (1983), Annual Review of Biochemistry, Volume 52, 467-506.
[b]For A/PR/8/34 strain
[c]Determined by biochemical and genetic approaches
[d]Determined by nucleotide sequence analysis and protein sequencing The pathogenicity of influenza viruses is modulated by multiple virus and host factors. Among the host factors that fight virus infections, the type I interferon (IFNα/β) system represents a powerful antiviral innate defense mechanism which was established relatively early in the evolution of eukaryotic organisms (García-Sastre, 2002, Microbes Infect 4:647-55). The antiviral IFNα/β, system involves three major steps: (i) detection of viral infection and IFNα/β secretion, (ii) binding of IFNα/β to its receptors and transcriptional induction of IFNα/β-stimulated genes, and (iii) synthesis of antiviral enzymes and proteins. Most viruses, however, have acquired specific genetic information encoding IFNα/β antagonist molecules, which effectively block one or more steps of the antiviral IFNα/β system. Influenza A viruses express a non-structural protein in infected cells, the NS1 protein (described in detail, infra), which counteracts the cellular IFNα/β response (Garcia-Sastre et al., 1998, Virology 252:324-30).

The influenza A virus genome contains eight segments of single-stranded RNA of negative polarity, coding for two nonstructural and nine structural proteins. The nonstructural protein NS1 is abundant in influenza virus infected cells, but has not been detected in virions. NS1 is a phosphoprotein found in the nucleus early during infection and also in the cytoplasm at later times of the viral cycle (King et al., 1975, Virology 64:378). Studies with temperature-sensitive (ts) influenza mutants carrying lesions in the NS gene suggested that the NS1 protein is a transcriptional and post-transcriptional regulator of mechanisms by which the virus is able to inhibit host cell gene expression and to stimulate viral protein synthesis. Like many other proteins that regulate post-transcriptional processes, the NS1 protein interacts with specific RNA sequences and structures. The NS1 protein has been reported to bind to different RNA species including: vRNA, poly-A, U6 snRNA, 5' untranslated region as of viral mRNAs and ds RNA (Qiu et al, 1995, RNA 1: 304; Qiu et al., 1994, J. Virol. 68: 2425; Hatada Fukuda 1992, J Gen Virol. 73:3325-9. Expression of the NS1 protein from cDNA in transfected cells has been associated with several effects: inhibition of nucleo-cytoplasmic transport of mRNA, inhibition of pre-mRNA splicing, inhibition of host mRNA polyadenylation and stimulation of translation of viral mRNA (Fortes, et al., 1994, EMBO J. 13: 704; Enami et al., 1994, J. Virol. 68: 1432; de la Luna et al., 1995, J. Virol. 69:2427; Lu et al., 1994, Genes Dev. 8:1817; Park et al., 1995, J. Biol Chem. 270, 28433; Nemeroff et al., 1998, Mol. Cell. 1:1991; Chen et al., 1994, EMBO J. 18:2273-83). In particular, the NS1 protein has three domains that have been reported to have a number of regulatory functions during influenza virus infection. The amino-terminal 73 amino acids are responsible for binding to RNAs (Qian et al., 1995, RNA 1:948-956), particularly double stranded RNAs, conferring to the virus the ability to escape the interferon α/β response (Donelan et al., 2003, J. Virol. 77:13257-66). The central portion of the protein interacts with the eukaryotic translation initiation factor 4GI facilitating preferential translation of viral mRNAs over host mRNAs (Aragón et al, 2000, Mol. Cell Biol. 20:6259-6268). The carboxy-terminus or the effector domain has been shown to inhibit host mRNA processing, specifically, inhibition of host mRNA polyadenylation (Nemeroff et al., 1998, Mol. Cell 1:991-1000), binding to poly(A) tails of mRNA inhibiting nuclear export (Qiu and Krug, 1994, J. Virol. 68:2425-2432) and inhibition of pre-mRNA splicing (Lu et al., 1994, Genes Dev. 8:1817-1828).

Studies of human recombinant influenza virus lacking the NS1 gene (delNS1) showed that this virus could only replicate in IFN-incompetent systems such as STAT1−/− mice or Vero cells; thus the NS1 protein is responsible for IFN antagonist activity (Garcia-Sastre et al., 1998, Virology 252:324-330). Also, it has been shown that human influenza viruses with truncated NS1 proteins are attenuated in mice (Egorov et al., 1998, J. Virol. 72:6437-6441) and provide protection against wild-type challenge (Talon et al., 2000, Proc. Natl. Acad. Sci. USA 97:4309-4314).

2.2 Equine Influenza Virus

Equine influenza virus belongs to the Orthomyxoviridae family of Influenza type A viruses. It is an enveloped, negative sense RNA virus, with a segmented, single-stranded genome. There are two distinct subtypes of equine influenza virus: Subtype 1, H7N7, first isolated in Prague in 1956 (Sovinova et al., 1958, Acta Virol. 2:52-61), and subtype 2. H3N8, first isolated in Miami in 1963 (Wadell et al., 1963, J. Am. Vet. Med. Assoc. 143:587-590). It is believed that subtype 1 is no longer in circulation as the last confirmed outbreak caused by this virus was in 1978 (Webster, R. G., 1993, Equine Vet. 25:537-538).

Equine influenza has been recognized as a common malady of the horse for centuries and is considered the most economically important respiratory disease of the equine in countries with substantial breeding and racing industries. In a 1998 study of infectious upper respiratory tract disease in 151 horses in Colorado, it was found that the pathogen was responsible for two-thirds of equine viral respiratory infections (Mumford et al., 1998, J. Am. Vet. Med. Assoc. 213: 385-390).

Vaccination is the most effective method of prophylaxis against influenza, designed to elicit a protective antibody response and resistance to re-infection. Influenza viruses undergo continual antigenic variation of the surface glycoproteins, HA and NA. Thus, in order to be effective, influenza vaccines require frequent updating to include relevant circulating strains of equine influenza virus. The most widely used vaccines are inactivated (killed) whole equine influenza virus preparations. However, the ability of some of these vaccines to provide protection against disease has been proven to be quite poor in efficacy studies. In one study, Morley et al. demonstrated that horses vaccinated with an inactivated aluminum phosphate adjuvanted vaccine did not differ significantly from those given a placebo, in the severity of the clinical disease they suffered during an influenza epidemic (Morley et al., 1999, J. Am. Vet. Med. Assoc. 215:61-66). However, a cold-adapted (ts), modified-live attenuated influenza virus vaccine (Flu-Avert™ I.N., Heska Corp.) has shown more promising results. Efficacy trials of this vaccine showed animals were clinically protected three months after vaccination (Lunn et al., 2001, J. Am. Vet. Med. Assoc. 218: 900-906) and had reduced severity of disease with significant clinical protection six months after vaccination (Townsend, 2001, Equine Vet. J. 33:637-643).

2.3 Attenuated Viruses

Inactivated virus vaccines are prepared by "killing" the viral pathogen, e.g., by heat or formalin treatment, so that it is not capable of replication. Inactivated vaccines have limited utility because they do not provide long lasting immunity and, therefore, afford limited protection. An alternative approach for producing virus vaccines involves the use of attenuated live virus vaccines. Attenuated viruses are capable of replication but are not pathogenic, and, therefore, provide for longer lasting immunity and afford greater protection. However, the conventional methods for producing attenuated viruses involve the chance isolation of host range mutants, many of which are temperature sensitive; e.g., the virus is passaged through unnatural hosts, and progeny viruses which are immunogenic, yet not pathogenic, are selected.

A conventional substrate for isolating and growing influenza viruses for vaccine purposes are embryonated chicken eggs. Influenza viruses are typically grown during 2-4 days at 37° C. in 10-12 day old eggs. Although most of the human primary isolates of influenza A and B viruses grow better in the amniotic sac of the embryos, after 2 to 3 passages the viruses become adapted to grow in the cells of the allantoic cavity, which is accessible from the outside of the egg (Murphy, B. R., and R. G. Webster, 1996. Orthomyxoviruses pp. 1397-1445. In Fields Virology. Lippincott-Raven P. A.).

Recombinant DNA technology and genetic engineering techniques, in theory, would afford a superior approach to producing an attenuated virus since specific mutations could be deliberately engineered into the viral genome. However, the genetic alterations required for attenuation of viruses are not known or predictable. In general, the attempts to use recombinant DNA technology to engineer viral vaccines have mostly been directed to the production of subunit vaccines which contain only the protein subunits of the pathogen involved in the immune response, expressed in recombinant viral vectors such as vaccinia virus or baculovirus. More recently, recombinant DNA techniques have been utilized in an attempt to produce herpes virus deletion mutants or polioviruses which mimic attenuated viruses found in nature or known host range mutants. Until 1990, the negative strand RNA viruses were not amenable to site-specific manipulation at all, and thus could not be genetically engineered.

Although attenuated influenza viruses are beneficial because they are immunogenic and not pathogenic, they are difficult to propagate in conventional substrates for the purposes of making vaccines. Furthermore, attenuated viruses may possess virulence characteristics that are so mild as to not allow the host to mount an immune response sufficient to meet subsequent challenges.

An alternative approach for producing virus vaccines to the inactivated virus vaccines in which the viral pathogen is "killed", involves the use of attenuated live virus vaccines which are capable of replication but are not pathogenic. Live vaccines which are administered intranasally may have advantages over their inactivated counterparts. Firstly, live vaccines are thought to induce improved cross-reactive cell-mediated cytotoxicity as well as a humoral antibody response, providing better protection than inactivated vaccines (Gorse and Belshe, 1990, J. Clin. Microbiol. 28:2539-2550; and Gorse et al., 1995, J. Infect. Dis. 172:1-10). Secondly, protective immunity to equine influenza virus is likely to involve mucosal IgA response which is not seen with traditional intramuscularly administered vaccines (Nelson et al., 1998, Vaccine 16:1306-1313). Finally, live vaccines also have the advantage of intranasal administration which avoids the swelling and muscle soreness occasionally associated with the intramuscular administration of inactivated adjuvanted vaccines. These live vaccines have been reported to induce not only humoral responses against homotypic influenza virus but also crossreactive cell-mediated cytotoxicity. Further advantages of live vaccines include the ease of intranasal administration, induction of mucosal immunity, longer lasting immunity, and its cost effectiveness. Equine influenza virus replicates in the nasal mucosa, thus an intranasally administered vaccine may be a preferable route of inoculation to elicit this response (Soboll et al., 2003, Vaccine 21:3081-3092). These are all important considerations regarding potential equine influenza vaccines.

Thus, new and more effective vaccines and immunogenic formulations for preventing equine influenza virus infections generated by such technology are needed.

3. SUMMARY OF THE INVENTION

The present invention provides attenuated equine influenza viruses having an impaired ability to antagonize the cellular interferon (IFN) response, methods for producing such attenuated equine influenza viruses, and the use of such viruses in vaccine and pharmaceutical formulations. Such viruses are capable of generating an immune response and creating immunity but not causing illness or causing fewer and/or less severe symptoms, i.e., the viruses have decreased virulence. Therefore, they are ideal candidates for live virus vaccines. Moreover, the attenuated viruses can induce a robust IFN response which has other biological consequences in vivo, affording protection against subsequent infectious diseases and/or inducing antitumor responses. Therefore, the attenuated viruses can be used pharmaceutically, for the prevention or treatment of other infectious diseases and/or IFN-treatable diseases.

The invention is based, in part, on the Applicants' discovery that equine influenza viruses engineered to contain or containing a deletion(s) in the NS1 gene have impaired replication relative to wild-type equine influenza viruses. Surprisingly, and contrary to results seen with human influenza virus in mouse models, the length of the NS1 protein does not correlate with the level of attenuation of the equine influenza virus. Applicants have discovered that with equine influenza, a mutant virus with the shortest NS1 protein is the least attenuated. In other words, equine influenza viruses containing shorter deletions in the NS1 gene exhibit a greater attenuation in vivo than equine influenza viruses containing longer deletions in their NS1 gene, or wild-type equine influenza viruses. Applicants have further discovered that the recombinant equine influenza viruses are impaired in their ability to inhibit IFN production in vitro, and they do not replicate as efficiently as the parental recombinant strain in embryonated hen eggs, in MDCK cells or in an in vivo mouse model. While not intending to be bound to any theory or explanation for the mechanism of action of the equine influenza virus NS1 deletion mutants in vivo, the attenuated features of such viruses are presumably due to their levels of NS1 protein expression, their ability to induce a robust cellular IFN response, and their impaired ability to antagonize such a response. However, the beneficial features of such viruses may not be solely attributable to their effect on the cellular interferon response. Indeed, alterations in other activities associated with NS1, such as, alteration of pre-mRNA splicing, inhibition of cellular mRNA polyadenylation, poly(A)-containing mRNA nucleocytoplasmic transport, and stimulation of viral protein synthesis, may contribute to the desired attenuated phenotype achieved by the introduction of mutations in the NS1 gene of equine influenza virus.

An attenuated equine influenza virus of the present invention comprises a mutation in an equine influenza NS1 gene that diminishes the ability of the NS1 gene product to antagonize the cellular interferon response. In one embodiment, an attenuated equine influenza virus of the invention comprises a genome comprising a mutation in an equine influenza virus NS1 gene that diminishes the ability of the NS1 gene product to antagonize a cellular interferon response, and permits the attenuated virus, at a multiplicity of infection (MOI) of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, approximately 3 to approximately 15 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type equine influenza virus in cells (e.g., cells of human, mouse, chicken, rat, birds, horse (e.g., equine fetal kidney cells or equine dermal cells), etc.), as determined approximately 2 to 10 days, 3 to 7 days, 3 to 5 days, or 2, 3, 4, 5, 6, 7, 8, 9, 10 days post-infection when propagated under the same conditions. The titers of attenuated and wild-type equine influenza viruses can be determined utilizing any technique well-known in the art or described herein (e.g., hemagglutination assays, plaque assays, tissue culture infectious dose 50 (TCID50), egg infectious dose 50 (EID50), etc.), and the viruses can be propagated under conditions described herein or well-known in the art (e.g., in horse cells, MDCK cells (e.g., in MEM, 10% v/v fetal calf serum (FCS), 1% penicillin/streptomycin at 37° C. in a 5% $CO_2$ humidified incubator) or embryonated chicken eggs (e.g., in a stationary incubator at 37° C. with 55% relative humidity). Alternatively, the viruses can be propagated in cells (e.g., in horse cells, MDCK cells, etc.) that are grown in serum-free or serum reduced (e.g., TPCK trypsin) medium.

In a specific embodiment, an attenuated equine influenza virus of the invention comprises a genome comprising a mutation in an equine influenza virus NS1 gene that diminishes the ability of the NS1 gene product to antagonize a cellular interferon response, and permits the attenuated virus, at a multiplicity of infection (MOI) of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, approximately 3 to approximately 15 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type equine influenza virus in horse cells (e.g., equine fetal kidney cells (e.g., FEK or EFK-2 cells)), as determined approximately 2 to 10 days, 3 to 7 days, 3 to 5 days, or 2, 3, 4, 5, 6, 7, 8, 9, 10 days post-infection when propagated under the same conditions. The titers of attenuated and wild-type equine influenza viruses can be determined utilizing any technique well-known in the art or described herein, (e.g., hemagglutination assays, plaque assays, etc.) and the viruses can be propagated under conditions described herein or well-known in the art (e.g., in horse cells, MDCK cells (e.g., in MEM, 10% v/v fetal calf serum (FCS), 1% penicillin/streptomycin at 37° C. in a 5% $CO_2$ humidified incubator) or embryonated chicken eggs (e.g., in a stationary incubator at 37° C. with 55% relative humidity).

The equine influenza viruses used in accordance with the invention may be selected from naturally occurring strains, variants or mutants; mutagenized viruses (e.g., viruses generated by exposure to mutagens, repeated passages and/or passage in non permissive hosts); reassortants; and/or genetically engineered viruses (e.g., using the "reverse genetics" and helper-free plasmid based techniques) having the desired phenotype—i.e., an impaired ability to antagonize the cellular IFN response. The naturally occurring strains, variants or mutants, reassortments and/or genetically engineered viruses with the desired interferon antagonist phenotype can be selected based on differential growth in cells (e.g., cells of human, mouse, chicken, rat, birds, horse, etc.) in other assays described below. In certain embodiments, the equine influenza viruses of the invention are genetically engineered viruses. In other embodiments, the equine influenza viruses of the invention are not naturally occurring strains, variants or mutants and/or reassortments.

In a specific embodiment, an attenuated equine influenza virus of the invention comprises a genome comprising a mutation in an equine influenza virus NS1 gene that diminishes the ability of the NS1 gene product to antagonize a cellular interferon response, and permits the attenuated virus, at a multiplicity of infection (MOI) of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, approximately 3 to approximately 15 fold or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type equine influenza virus in horse cells (e.g., equine fetal kidney cells (e.g., FEK or EFK-2 cells)) as determined by a hemagglutination assay of BALF from horses or supernatants of horse cells approximately 2 to 10 days, 3 to 7 days, 3 to 5 days, or 2, 3, 5, 6, 7, 8, 9, 10 days post-infection or when the viruses are plaqued on Madin-Darby canine kidney (MDCK) cells. In one embodiment, the growth of an attenuated equine influenza virus of the invention is compared to a particular standard or reference, e.g., wild-type equine influenza virus A/Eq/KY/5/02. In accordance with these embodiments, the attenuated virus may be genetically engineered to contain or express non-equine influenza virus nucleic acid sequences such, e.g., an epitope of a foreign pathogen or a tumor antigen. Preferably, the non-equine influenza virus sequences do not include a nucleic acid sequence that alters the attenuated phenotype of the virus. Accordingly, nucleic acid sequences encoding proteins, polypeptides or peptides with interferon antagonizing activity are preferably not engineered into an equine influenza virus.

The invention provides attenuated equine influenza viruses comprising a genome comprising at least two, at least three, at least four or more mutations in two, three, four or more equine influenza virus genes, wherein at least one of the mutations is in the NS1 gene and contributes to or is responsible (directly or indirectly) for the attenuation of the virus and/or the diminished ability of the virus to antagonize a cellular interferon response. In one embodiment, an attenuated equine influenza virus of the invention comprises a genome comprising at least two, at least three, at least four or more mutations in two, three, four or more equine influenza virus genes, wherein at least one of the mutations is in the NS1 gene and is responsible for the diminished ability of the NS1 gene product to antagonize a cellular interferon response, and permits the attenuated virus, at a MOI of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, approximately 3 to approximately 15 fold or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type equine influenza virus in cells (e.g., cells of human, mouse, chicken, rat, birds, horse, etc.), as determined by, e.g., hemagglutination assays, approximately 2 to 10 days, 3 to 7 days, 3 to 5 days, or 2, 3, 5, 6, 7, 8, 9, 10 days post-infection when the viruses are propagated under the same conditions. In a specific embodiment, an attenuated equine influenza virus of the invention comprises a genome comprising at least two, at least three, at least four or more mutations in two, three, four or more equine influenza virus genes, wherein at least one of the mutations is in the NS1 gene and is responsible for the diminished ability of the NS1 gene product to antagonize a cellular interferon response, and permits the attenuated virus, at a MOI of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, approximately 3 to approximately 15 fold or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type equine influenza virus in horse cells, as determined by, e.g., hemagglutination assays, approximately 2 to 10 days, 3 to 7 days, 3 to 5 days, or 2, 3, 5, 6, 7, 8, 9, 10 days post-infection when the viruses are propagated under the same conditions (e.g., in MDCK cells). In another embodiment, an attenuated equine influenza virus of the invention comprises a genome comprising at least two, three, four or more mutations in two, three, four or more equine influenza virus genes, wherein at least one of the mutations is in the NS1 gene and is responsible for the attenuation of the virus, and permits the attenuated virus, at a MOI of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, approximately 3 to approximately 15 fold or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type equine influenza virus in horse cells, as determined by, e.g., hemagglutination assays, approximately 2 to 10 days, 3 to 7 days, 3 to 5 days, or 2, 3, 5, 6, 7, 8, 9, 10 days post-infection when the viruses are propagated under the same conditions (e.g., in MDCK cells). In accordance with these embodiments, the attenuated virus has an impaired interferon antagonist phenotype and may be genetically engineered to contain or express non-equine influenza virus nucleic acid sequences, such as, e.g., an epitope of a foreign pathogen (e.g., epitopes of Equine Reovirus (Orbivirus), Arteritis Virus, Equine Herpes Virus (EHV1, EHV2, EHV3, EHV4 and EHV5), Equine Papova Virus, Retrovirus, Adenovirus, African Horse Sickness Virus, Shipping Fever Virus, West Nile Virus, Equine Encephalitis Virus, Vesicular Stomatitis Virus (VSV), Equine Rhinovirus, and Hendra Virus), and antigenic determinants of non viral equine pathogens such as bacteria, including, but not limited to, *Clostridia* sp., *Salmonella* sp., *E. coli*, *Streptococcus equi*, *Taylorella equigenitalis* (CEM), *Klebsiella pneumoniae* and *Pseudomonas aeruginosa*, *Dermatophilus congolensis*, or a tumor antigen such as equine sarcoid Mc1 ($P_{55}$ or $P_{124}$), horse prostate kallikrein (HPK), carcinoembryonic antigen (CEA), breast cancer antigen such as EGFR (epidermal growth factor receptor), HER2 antigen (p185$^{HER2}$), HER2 neu epitope, cancer antigen-50 (CA-50), cancer antigen 15-3 (CA15-3) associated with breast cancer, carcinoma associated antigen (CAA), melanoma antigen, and melanoma associated antigens 100, 25, and 150). Preferably, the non-equine influenza virus sequences (heterologous sequences) do not include a nucleic acid sequence that alters the attenuated phenotype of the virus. Accordingly, nucleic acid sequences encoding proteins, polypeptides or peptides with interferon antagonizing activity are preferably not engineered into the equine influenza virus.

Mutations in the equine influenza virus NS1 gene comprise (alternatively, consist of) any mutation that results in the desired phenotype (i.e., an impaired ability to antagonize a cellular interferon response). Examples of the type of mutations that can be included in or introduced into an equine influenza virus NS1 gene include, but are not limited to, deletions, substitutions, insertions and combinations thereof. One or more mutations can be located anywhere throughout the NS1 gene, i.e., in the regulatory, non-coding and/or coding regions (e.g., the amino-terminus and/or the carboxy-terminus or somewhere in between). In a specific embodiment, an attenuated equine influenza virus of the invention comprises a genome comprising an equine influenza virus NS1 gene with a mutation (e.g., a deletion or substitution) at the amino terminus. In a preferred embodiment, an attenuated equine influenza virus of the invention comprises a genome comprising an equine influenza virus NS1 gene with a mutation (e.g., a deletion or substitution, preferably a deletion) at the carboxy terminus. In another embodiment, an attenuated equine influenza virus of the invention comprises a genome comprising a mutation in an equine influenza virus NS1 gene resulting in a deletion consisting of 5, preferably 10, 15, 20, 25, 30, 35, 40, 45, 50, 55, 60, 65, 70, 75, 80, 85, 90, 91, 92, 93, 94, 95, 100, 105, 110, 115, 119, 120, 121, 125, 130, 135, 140, 145, 146, 147, 148, 150, 155, 160, 165, 170 or 175 amino acid residues from the carboxy terminus of NS1, or a deletion of between 5-170, 25-170, 50-170, 100-170, 90-160, 100-160 or 105-160, 90-150, 5-75, 5-50 or 5-25 amino acid residues from the carboxy terminus. In another embodiment, an attenuated equine influenza virus of the invention comprises a genome comprising a mutation in an equine influenza virus NS1 gene resulting in a deletion of all amino acid residues of the NS1 gene product except amino acid residues 1-126, amino acid residues 1-120, amino acid residues 1-115, amino acid residues 1-110, amino acid residues 1-100, amino acid residues 1-99, amino acid residues 1-95, amino acid residues 1-85, amino acid residues 1-80, amino acid residues 1-75, amino acid residues 1-73, amino acid residues 1-70, amino acid residues 1-65 or amino acid residues 1-60, wherein the amino terminal amino acid is number 1. In a preferred embodiment, an attenuated equine influenza virus of the invention comprises a genome comprising a mutation in an equine influenza virus NS1 gene resulting in a deletion of nucleotides 405 to 482, nucleotides 324 to 482, or nucleotides 246 to 482. In accordance with these embodiments, the attenuated equine influenza virus is preferably genetically engineered. In a preferred embodiment, an attenuated equine influenza virus of the invention is Eq-NS1-126, Eq-NS1-99 or Eq-NS1-73.

The attenuated equine influenza virus of the present invention may be a chimeric virus that expresses a heterologous sequence. Preferably, the heterologous sequence is not a nucleic acid sequence that alters the attenuated phenotype of the virus. Accordingly, preferably, nucleic acid sequences encoding proteins, polypeptides or peptides with interferon antagonizing activity are not engineered into the equine influenza virus. In certain embodiments, the chimeric virus expresses a tumor antigen. In other embodiments, the chimeric virus expresses an epitope of a foreign pathogen.

An attenuated equine influenza virus having the desired phenotype can itself be used as the active ingredient in vaccine, pharmaceutical or immunogenic formulations. Alternatively, the attenuated equine influenza virus can be used as the vector or "backbone" of recombinantly produced vaccines or immunogenic formulations. To this end, the "reverse genetics" technique or helper-free plasmid approach can be used to engineer mutations or introduce foreign epitopes into the attenuated equine influenza virus, which would serve as the "parental" strain. In this way, vaccines can be designed for immunization against strain variants, or in the alternative, against completely different infectious agents or disease antigens (e.g., tumor antigens). For example, the attenuated equine influenza virus can be engineered to express neutralizing epitopes of other preselected strains. Alternatively, epitopes of other viruses can be built into the attenuated equine influenza virus. Alternatively, epitopes of non viral infectious pathogens (e.g., parasites, bacteria, fungi) can be engineered into the equine influenza virus.

In a particular embodiment, reassortment techniques can be used to transfer the attenuated phenotype from a parental equine influenza virus strain (a natural mutant, a mutagenized virus, or a genetically engineered virus) to a different virus strain (a wild-type virus, a natural mutant, a mutagenized virus, or a genetically engineered virus). In accordance with this embodiment, the "reverse genetics technique" or helper-free plasmid approach can be used to engineer mutations or introduce foreign epitopes into the attenuated equine influenza virus, which would serve as the "parental strain".

The present invention provides methods for vaccinating subjects comprising administering a vaccine formulation comprising an attenuated equine influenza virus comprising a mutation in an equine influenza NS1 gene that diminishes the ability of the NS1 gene product to antagonize the cellular interferon response, and a physiologically effective excipient. In one embodiment, the present invention provides a method comprising administering an effective amount of a vaccine formulation of the invention. In certain embodiments, the dose of the vaccine formulation administered is between about $10^2$ to about $10^8$, about $10^3$ to about $10^7$, or about $10^4$ to about $5\times10^6$ pfu. In other embodiments, the dose of the vaccine formulation administered is $10^2$, $5\times10^2$, $10^3$, $5\times10^3$, $10^4$, $5\times10^4$, $10^5$, $5\times10^5$, $10^6$, $5\times10^6$, $10^7$, $5\times10^7$ or $10^8$ pfu. In specific embodiments, the subject is a donkey, zebra, camel, dog, avian (e.g., a duck). In a preferred embodiment, the subject is a horse.

The present invention provides immunogenic formulations comprising an attenuated equine influenza virus of the invention and methods for inducing an immune response for the treatment, management or prevention of an equine influenza virus infection or a condition or symptom associated therewith, an infection, other than an equine influenza virus infection, or a condition or symptom associated therewith, or a condition in which the attenuated equine influenza viruses can be used as a vector to induce an immune response to a particular antigen associated with the condition, comprising administering to a subject an immunogenic formulation of the invention. In one embodiment, the present invention provides a method for inducing an immune response for the treatment, management or prevention of an equine influenza virus infection or a condition or symptom associated therewith, an infection, other than an equine influenza virus infection, or a condition or symptom associated therewith, or a condition in which the attenuated equine influenza viruses can be used as a vector to induce an immune response to a particular antigen associated with the condition, comprising administering to a subject an effective amount of an immunogenic formulation of the invention. In certain embodiments, the dose of an immunogenic formulation of the invention administered to a subject is between about $10^2$ to about $10^8$, about $10^3$ to about $10^7$, or about $10^4$ to about $5\times10^6$ pfu or about $10^4$ to about $10^7$ pfu. In specific embodiments, the immunogenic formulation administered to a subject has an attenuated equine influenza virus concentration of about $10^4$ to about $10^7$ pfu/ml. In other embodiments, the dose of an immunogenic formulation of the invention administered to a subject is $10^2$, $5\times10^2$, $10^3$, $5\times10^3$, $10^4$, $5\times10^4$, $10^5$, $5\times10^5$, $10^6$, $5\times10^6$, $10^7$, $5\times10^7$ or $10^8$ pfu. In specific embodiments, the subject is a donkey, zebra, camel, dog, avian (e.g., a duck). In a preferred embodiment, the subject is a horse.

The attenuated equine influenza viruses, which induce robust IFN responses in subjects, may also be used in pharmaceutical formulations for the prophylaxis or treatment of infections and IFN-treatable diseases such as cancer. In this regard, the tropism of the attenuated equine influenza virus can be altered to target the virus to a desired target organ, tissue or cells in vivo or ex vivo. Using this approach, the IFN response can be induced locally, at the target site, thus avoiding or minimizing the side effects of systemic IFN therapy. To this end, the attenuated equine influenza virus can be engineered to express a ligand specific for a receptor of the target organ, tissue or cells.

The present invention provides methods for preventing, managing or treating an infection, or IFN-treatable disease in a subject (e.g., a horse), other than an equine influenza viral infection or IFN-treatable disease caused by equine influenza virus, comprising administering a pharmaceutical formulation of the invention. In one embodiment, the present invention provides a method for preventing, managing or treating an infection or IFN-treatable disease in a subject, other than an equine influenza viral infection or IFN-treatable disease caused by equine influenza virus, comprising administering to a subject an effective amount of a pharmaceutical formulation of the invention. In certain embodiments, the dose of the pharmaceutical formulation administered to the subject is between about $10^2$ to about $10^{12}$, about $10^2$ to about $10^{10}$, about $10^2$ to about $10^8$, about $10^3$ to about $10^9$, about $10^3$ to about $10^7$, about $10^4$ to about $10^8$, about $10^4$ to about $5\times10^6$, about $10^4$ to about $10^7$, or about $10^4$ to about $10^{12}$ pfu. In specific embodiments, the pharmaceutical formulation administered to the subject has an attenuated influenza virus concentration from about $10^4$ to about $10^{12}$ pfu/ml. In other embodiments, the dose of the pharmaceutical formulation administered is $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu. In specific embodiments, the subject is a donkey, zebra, camel, dog, avian (e.g., a duck). In a preferred embodiment, the subject is a horse.

The present invention provides methods for preventing, managing or treating cancer in a subject comprising administering a pharmaceutical formulation of the invention. In one embodiment, the present invention provides a method for preventing, managing or treating cancer in a subject comprising administering to a subject an effective amount of a pharmaceutical formulation of the invention. In certain embodiments, the pharmaceutical formulation comprises an equine influenza virus comprising a tumor antigen. In certain embodiments, the dose of the pharmaceutical formulation administered to the subject is between about $10^2$ to about $10^{12}$, about $10^2$ to about $10^{10}$, about $10^2$ to about $10^8$, about $10^3$ to about $10^9$, about $10^3$ to about $10^7$, about $10^4$ to about $10^8$, about $10^4$ to about $5\times10^6$ pfu or about $10^4$ to about $10^{12}$ pfu. In other embodiments, the dose of the pharmaceutical formulation administered is $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu. In specific embodiments, the subject is a donkey, zebra, camel, dog, avian (e.g., a duck). In a preferred embodiment, the subject is a horse.

Applicants have demonstrated that attenuated equine influenza viruses with impaired interferon antagonist activity replicate in vivo generating titers that are lower than than detected with wild-type equine influenza viruses, but that are sufficient to induce immunological and cytokine responses. Thus, mutations which diminish but do not abolish the IFN antagonist activity of the equine influenza virus are preferred for vaccine, immunologic, and pharmaceutical formulations. Such viruses can be selected for growth in both conventional and non conventional substrates, and for intermediate virulence.

The present invention provides cells containing (alternatively, comprising) equine influenza viruses of the present invention. In a specific embodiment, a cell contains/comprises an equine influenza virus that is genetically engineered. In certain embodiments, the attenuated equine influenza virus contained in the cell is engineered to encode an epitope derived from another pathogen (e.g., another virus) or a tumor antigen. In accordance with this embodiment, the genome of the attenuated equine influenza virus may comprise at least one segment derived from a different virus. Any cell can be infected with, contain or comprise an attenuated equine influenza virus of the invention including, but not limited to, MDCK cells, Vero cells, primary human umbilical vein endothelial cells (HLUVEC), H292 human epithelial cell line, HeLa cells, and equine embryonic kidney cells (e.g., FEK or EFK-2 cells). In a preferred embodiment, the cell is a horse cell or a horse cell line. In certain embodiments, the cell (e.g., a horse cell or horse cell line) is interferon-deficient.

In certain other embodiments, the equine influenza viruses of the invention are contained in 10 day-old, 6 to 9 day-old, 6 to 8 day-old, or 6 to 7 day-old embryonated chicken eggs. In a specific embodiment, the viruses are contained in allantoic cavity of such eggs. In another specific embodiment, the viruses are contained in the amniotic cavity of such eggs.

The invention encompasses the use of substrates such as cells, cell lines and embryonated eggs, to propagate the attenuated equine influenza viruses of the invention. In one embodiment, the invention provides methods for vaccine production and pharmaceutical production comprising propagating in a substrate an attenuated equine influenza virus of the present invention and collecting progeny virus, wherein the substrate is a cell, cell line or embryonated egg. In certain embodiments, the substrate is an IFN deficient system. Exemplary IFN-deficient systems include, but are not limited to, young embryonated eggs (e.g., 6 to 10 days old, 6 to 9 days old, 6 to 8 days old or 6 to 7 days old embryonated eggs), and IFN deficient cell lines (such as VERO cells or genetically engineered cell lines such as STAT1 knockouts). Embryonated eggs or cell lines pretreated with compounds that inhibit the IFN system (including drugs, antibodies, antisense, ribozymes, etc.) can also be used as an IFN-deficient system. Further, eggs deficient in the IFN system, e.g., eggs produced by STAT1 negative birds, especially fowl, including but not limited to transgenic chickens, ducks or turkeys, may be used as an IFN-deficient system.

3.1 Terminology

As used herein, the term "about" or "approximately" when used in conjunction with a number refers to any number within 1, 5 or 10% of the referenced number.

As used herein, the phrase "amino-terminus" of NS1 refer to the amino acids from the amino terminal amino acid residue (amino acid residue 1) through amino acid residue 115, amino acid residues 1 through 100, amino acid residues 1 through 75, amino acid residues 1 through 50, amino acid residues 1 through 25, or amino acid residues 1 through 10 of the equine influenza viral NS1 protein.

As used herein, the phrase "carboxy-terminus" of NS1 refer to amino acid residues 116 through the carboxy terminal amino acid residue, amino acid residues 101 through the carboxy terminal amino acid residue, amino acid residues 76 through the carboxy terminal amino acid residue, amino acid residues 51 through the carboxy terminal amino acid residue, or amino acid residues 26 through the carboxy terminal amino acid residue of the equine influenza viral NS1 protein, when the amino-terminus of NS1 is amino acid residues 1 through amino acid residue 115, amino acid residues 1 through 100, amino acid residues 1 through 75, amino acid residues 1 through 50, or amino acid residues 1 through 25, respectively, of the equine influenza viral NS1 protein. Deletions from the carboxy terminus can include deletions consisting of 5, preferably 10, 15, 20, 25, 30, 35, 40, 45, 50, 55, 60, 65, 70, 73, 75, 80, 85, 90, 95, 99, 100, $10^5$, 110, 115, 120, 125, 126, 130, 135, 140, 145, 150, 155, 160, 165, 170 or 175 amino acid residues from the carboxy terminus of NS1.

As used herein, the term "cytokine receptor modulator" refers to an agent which modulates the phosphorylation of a cytokine receptor, the activation of a signal transduction pathway associated with a cytokine receptor, and/or the expression of a particular protein such as a cytokine. Such an agent may directly or indirectly modulate the phosphorylation of a cytokine receptor, the activation of a signal transduction pathway associated with a cytokine receptor, and/or the expression of a particular protein such as a cytokine. Thus, examples of cytokine receptor modulators include, but are not limited to, cytokines, fragments of cytokines, fusion proteins, and antibodies that immunospecifically binds to a cytokine receptor or a fragment thereof. Further, examples of cytokine receptor modulators include, but are not limited to, peptides, polypeptides (e.g., soluble cytokine receptors), fusion proteins and antibodies that immunospecifically binds to a cytokine or a fragment thereof.

As used herein, the term "effective amount" refers to the amount of a therapy (e.g., a prophylactic or therapeutic agent) which is sufficient to reduce and/or ameliorate the severity and/or duration of a condition (e.g., an equine influenza virus infection or a condition or symptom associated therewith, another infection (e.g., another viral infection), an IFN treatable disease or a condition in which the attenuated equine influenza viruses can be used as a vector to induce an immune response to a particular antigen associated with the condition), prevent the advancement of a condition (e.g., an equine influenza virus infection or a condition or symptom associated therewith, another infection (e.g., another viral infection), an IFN treatable disease or a condition in which the attenuated equine influenza viruses can be used as a vector to induce an immune response to a particular antigen associated with the condition), cause regression of a condition (e.g., an equine influenza virus infection or a condition or symptom associated therewith, another infection (e.g., another viral infection) or an IFN treatable disease), prevent the recurrence, development, or onset of one or more symptoms associated with a condition (e.g., an equine influenza virus infection or a condition or symptom associated therewith, another infection (e.g., another viral infection) or an IFN treatable disease), reduce the titer of equine influenza virus or enhance or improve the prophylactic or therapeutic effect(s) of another therapy (e.g., prophylactic or therapeutic agent).

As used herein, the term "epitopes" refers to sites or fragments of a polypeptide or protein having antigenic or immunogenic activity in an animal, preferably in a mammal, and most preferably in a horse. An epitope having immunogenic activity is a site or fragment of a polypeptide or protein that elicits an antibody response in an animal. An epitope having antigenic activity is a site or fragment of a polypeptide or protein to which an antibody immunospecifically binds as determined by any method well-known to one of skill in the art, for example by immunoassays.

As used herein, "equine influenza virus" refers to a type A influenza virus from the family orthomyxovirus that causes equine influenza. While orthomyxovirus has three groups: type A, type B and type C, only type A influenza viruses is currently known to infect horses. Subtypes of equine influenza virus include H7N7 and H3N8. In a preferred embodiment, an equine influenza virus contains an equine NS1 gene. Representative equine NS1 genes can be found in public sequence databases such as Genbank and include, but are not limited to, Genbank Accession Nos. AJ430785, AY328471, X80060, AF001673, AF001672, AF001671, AF001670, AF001669, AF001668, AF001668, AF001667, AF001666, AF001665, AF001664, AF001663, AF001662, U49489, 49487, U49486, and M65020. Examples of equine influenza virus variants include, but are not limited to, A/eq/KY/5/02, A/eq/Miami/1/63, A/eq/Fontainebleau/1/79, A/eq/KY/1/81, A/eq/Sussex/1/89 or A/eq/Saskatoon/1/90, A/eq/KY/2004, A/eq/South Africa/2003, A/eq/Newmarket/2004, A/eq/KY/5/2002, A/eq/New York/73, A/eq/KY/92, A/eq/Hong Kong/92, A/eq/Miami/63, and A/eq/Prague/56. Such variants contain the wild-type NS1 and other equine influenza genes.

As used herein, the term "fragment" in the context of a proteinaceous agent refers to a peptide or polypeptide comprising an amino acid sequence of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a peptide, polypeptide or protein. In one embodiment, a fragment of a full-length protein retains activity of the full-length protein, e.g., IFN antagonist activity. In another embodiment, the fragment of the full-length protein does not retain the activity of the full-length protein, e.g., IFN antagonist activity.

As used herein, the term "fragment" in the context of a nucleic acid refers to a nucleic acid comprising an nucleic acid sequence of at least 2 contiguous nucleotides, at least 5 contiguous nucleotides, at least 10 contiguous nucleotides, at least 15 contiguous nucleotides, at least 20 contiguous nucleotides, at least 25 contiguous nucleotides, at least 30 contiguous nucleotides, at least 35 contiguous nucleotides, at least 40 contiguous nucleotides, at least 50 contiguous nucleotides, at least 60 contiguous nucleotides, at least 70 contiguous nucleotides, at least contiguous 80 nucleotides, at least 90 contiguous nucleotides, at least 100 contiguous nucleotides, at least 125 contiguous nucleotides, at least 150 contiguous nucleotides, at least 175 contiguous nucleotides, at least 200 contiguous nucleotides, at least 250 contiguous nucleotides, at least 300 contiguous nucleotides, at least 350 contiguous nucleotides, or at least 380 contiguous nucleotides of the nucleic acid sequence encoding a peptide, polypeptide or protein. In a preferred embodiment, a fragment of a nucleic acid encodes a peptide or polypeptide that retains activity of the full-length protein, e.g., IFN antagonist activity. In another embodiment, the fragment of the full-length protein does not retain the activity of the full-length protein, e.g., IFN antagonist activity.

As used herein, the phrase "heterologous sequence" refers to any sequence nucleic acid or protein, polypeptide or peptide sequence which is not normally found or associated in nature with a nucleic acid or protein, polypeptide or peptide sequence of interest. For example, a "heterologous sequence" may refer to a sequence derived from a different species.

As used herein, the term "in combination" refers to the use of more than one therapy (e.g., more than one prophylactic agent and/or therapeutic agent). The use of the term "in combination" does not restrict the order in which therapies (e.g., prophylactic and/or therapeutic agents) are administered to a subject with a condition (e.g., an equine influenza virus infection or a condition or symptom associated therewith, another infection (e.g., another viral infection) or an IFN treatable disease). A first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a second prophylactic or therapeutic agent) to a subject with a condition (e.g., an equine influenza virus infection or a condition or symptom associated therewith, another infection (e.g., another viral infection) or an IFN treatable disease).

As used herein, the phrase "interferon antagonist activity" refers to a protein or polypeptide, or fragment, derivative, or analog thereof that reduces or inhibits the cellular interferon immune response. In particular, a protein or polypeptide, or fragment, derivative, or analog thereof (e.g., equine influenza virus NS1) that has interferon antagonist activity reduces or inhibits interferon expression and/or activity. In a specific embodiment, the phrase "interferon antagonist activity" refers to an equine influenza virus protein or polypeptide, or fragment, derivative, or analog thereof that reduces or inhibits the cellular interferon immune response. An equine influenza viral protein or polypeptide with interferon antagonist activity may preferentially affect the expression and/or activity of one or two types of interferon (IFN). In one embodiment, the expression and/or activity of IFN-$\alpha$ is affected. In another embodiment, the expression and/or activity of IFN-$\beta$ is affected. In one embodiment, the expression and/or activity of IFN-$\gamma$ is affected. In certain embodiments, the expression and/or activity of IFN-$\beta$ and/or IFN-$\gamma$ is reduced 5-10%, 10-20%, 20-30%, 30-40%, 40-50%, 50-60%, 60-70%, 70-80%, 80-90% or more by protein, polypeptide, etc. with an interferon antagonist activity when compared to a control (e.g., PBS or a protein without interferon antagonist activity) in IFN-competent systems, e.g., a wild-type cell or animal under the same conditions. In certain embodiments, the expression and/or activity of IFN-$\beta$ and/or IFN-$\gamma$ is reduced approximately 1 to approximately 100 fold, approximately 5 to approximately 80 fold, approximately 20 to approximately 80 fold, approximately 1 to approximately 10 fold, or approximately 1 to approximately 5 fold, or approximately 40 to approximately 80 fold, or 1, 2, 3, 4, 5, 7, 10, 15, 20, 25, 30, 35, 40, 45, 50, 55, 60, 65, 70, 75, 80, 85, 90, 95 or 100 fold by protein, polypeptide, etc. with an interferon antagonist activity when compared to a control (e.g., PBS or a protein without interferon antagonist activity) in IFN-competent systems under the same conditions.

As used herein, the phrases "IFN deficient systems" or "IFN-deficient substrates" refer to systems, e.g., cells, cell lines and animals, such as horses, mice, chickens, turkeys, rabbits, rats, etc., which do not produce IFN or produce low levels of IFN (i.e., a reduction in IFN expression of 5-10%, 10-20%, 20-30%, 30-40%, 40-50%, 50-60%, 60-70%, 70-80%, 80-90% or more when compared to IFN-competent systems under the same conditions), do not respond or respond less efficiently to IFN, and/or are deficient in the activity of one or antiviral genes induced by IFN.

As used herein, the phrase "IFN-inducing phenotype" refers to a phenotype whereby a virus demonstrates an increased cellular interferon response compared to a wild-type virus, which typically inhibits or reduces cellular interferon mediated responses.

As used herein, the phrases "IFN treatable disorders", "IFN treatable diseases" and analogous phrases refer to conditions that are preventable, treatable, managed or ameliorated by the administration of IFN, either IFN-$\alpha$, $\beta$, $\gamma$ or any combination thereof. The IFN treatable disorders need not be limited to equine, if equine influenza virus infects other species. Examples of IFN treatable disorders in horses include, but are not limited to, equine arteritis, Equine Rhinovirus, Shipping Fever, Hendra Virus, African Horse Sickness Virus, Equine Encephalitis Virus (Eastern, Western, Venezuelan), West Nile Fever Virus and Vesicular Stomatitis Virus (VSV).

As used herein, the phrase "intermediate" phenotype with respect to IFN-antagonist activity refers to a phenotype which can stimulate a robust immune response, while being attenuated because viruses with an intermediate phenotype cannot overcome the host IFN response. In particular, an intermediate phenotype can stimulate an immune response and inhibit/reduce IFN only to the extent that it allows fewer rounds of virus replication or lower numbers of virus particles being produced compared to wild-type virus, as determined by techniques well-known in the art (e.g., as measured by lower plaque titer or hemagglutination assays).

As used herein, the term "isolated", in the context of viruses, refers to a virus that is derived from a single parental virus. A virus can be isolated using routine methods known to one of skill in the art including, but not limited to, those based on plaque purification and limiting dilution.

As used herein, the terms "manage," "managing," and "management" refer to the beneficial effects that a subject derives from a therapy (e.g., a prophylactic or therapeutic agent), which does not result in a cure of the disease. In certain embodiments, a subject is administered one or more therapies (e.g., one or more prophylactic or therapeutic agents) to "manage" a disease so as to prevent the progression or worsening of the disease.

As used herein, the phrase "multiplicity of infection" or "MOI" is the average number of virus per infected cell. The MOI is determined by dividing the number of virus added (ml added x Pfu) by the number of cells added (ml added x cells/ml).

As used herein, the phrase "non-equine influenza virus" in the context of equine influenza viruses containing or comprising non-equine influenza virus sequences refers to any influenza virus strain or isolate comprising a sequence (e.g., a nucleic acid or amino acid sequence) heterologous to equine influenza virus, i.e, the sequence is not found to naturally in association with equine influenza virus.

As used herein, the phrase "NS1 gene" refers to the gene which encodes the nonstructural protein (NS1) in influenza. NS1 is one of the eight molecules encoded by the segmented genome of influenza A and other viruses. An "equine influenza virus NS1 gene" is an NS1 gene isolated from an equine influenza virus. Representative equine NS1 genes can be found in public sequence databases such as Genbank and include, but are not limited to, Genbank Accession Nos. AJ430785, AY328471, X80060, AF001673, AF001672, AF001671, AF001670, AF001669, AF001668, AF001668, AF001667, AF001666, AF001665, AF001664, AF001663, AF001662, U49489, 49487, U49486, and M65020. An "NS1 gene product" refers to a gene product (e.g., a RNA or protein) encoded by an NS1 gene. In the case of a protein, the NS1 gene product is full-length and has wild-type NS1 activity (e.g., from strain A/WSN/33). An "equine influenza virus NS1 gene product refers to a gene product (e.g., a RNA or protein) encoded by an equine influenza virus NS1 gene. In the case of a protein, the equine influenza virus NS1 gene product is full-length and has wild-type equine influenza virus NS1 activity (e.g., from strain A/WSN/33 A/Eq/KY/5/02).

As used herein, the terms "prevent", "preventing" and "prevention" refer to the inhibition of the development or onset of a condition (e.g, an equine influenza virus infection or a condition associated therewith, an infection other than an equine influenza virus infection or a condition associated therewith, an IFN-treatable disease or a condition in which the attenuated equine influenza viruses can be used as a vector to induce an immune response to a particular antigen associated with the condition), or the prevention of the recurrence, onset, or development of one or more symptoms of a condition (e.g., an equine influenza virus infection or a condition associated therewith, an infection other than an equine influenza virus infection or a condition associated therewith, or an IFN-treatable disease), in a subject resulting from the administration of a therapy (e.g., a prophylactic or therapeutic agent), or the administration of a combination of therapies (e.g., a combination of prophylactic or therapeutic agents).

As used herein, the terms "prophylactic agent" and "prophylactic agents" refer to any agent(s) which can be used in the prevention of a condition or a symptom thereof (e.g., an equine influenza virus infection or a condition or symptom associated therewith, an infection other than an equine influenza virus infection or a condition or symptom associated therewith, an IFN treatable disease or a condition in which the attenuated equine influenza viruses can be used as a vector to induce an immune response to a particular antigen associated with the condition). Preferably, a prophylactic agent is an agent which is known to be useful to or has been or is currently being used to the prevent or impede the onset, development, progression and/or severity of an equine influenza virus infection or a condition or symptom associated therewith, an infection other than an equine influenza virus infection or a condition or symptom associated therewith, an IFN treatable disease or a condition in which the attenuated equine influenza viruses can be used as a vector to induce an immune response to a particular antigen associated with the condition.

As used herein, the term "prophylactically effective amount" refers to the amount of a therapy (e.g., prophylactic agent) which is sufficient to result in the prevention of the development, recurrence, or onset of a condition or a symptom thereof (e.g., an equine influenza virus infection or a condition or symptom associated therewith, an infection other than an equine influenza virus infection or a condition or symptom associated therewith, an IFN treatable disease or a condition in which the attenuated equine influenza viruses can be used as a vector to induce an immune response to a particular antigen associated with the condition) or to enhance or improve the prophylactic effect(s) of another therapy (e.g., a prophylactic agent).

As used herein, the phrase "purified" in the context of viruses refers to a virus which is substantially free of cellular material and culture media from the cell or tissue source from which the virus is derived. The language "substantially free of cellular material" includes preparations of virus in which the virus is separated from cellular components of the cells from which it is isolated or recombinantly produced. Thus, virus that is substantially free of cellular material includes preparations of protein having less than about 30%, 20%, 10%, or 5% (by dry weight) of cellular protein (also referred to herein as a "contaminating protein"). The virus is also substantially free of culture medium, i.e., culture medium represents less than about 20%, 10%, or 5% of the volume of the virus preparation. A virus can be purified using routine methods known to one of skill in the art including, but not limited to, chromatography and centrifugation.

As used herein, the terms "subject" or "patient" are used interchangeably. As used herein, the terms "subject" and "subjects" refers to an animal (e.g., birds, reptiles, and mammals), preferably a mammal including a non-primate (e.g., a camel, donkey, zebra, cow, horse, horse, cat, dog, rat, and mouse) and a primate (e.g., a monkey, chimpanzee, and a human). In certain embodiments, the subject or patient has an equine influenza virus infection. In certain embodiments, the mammal is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In a preferred embodiment, the subject or patient is a horse. In certain embodiments, the horse is 0 to 6 months old, 6 to 12 months old, 1 to 5 years old, 5 to 10 years old or 10 to 15 years old, 15 to 20 years old, 20 to 25 years old, 25 to 30 years old or 30 to 35 years old. The natural lifespan of a horse is 25 to 35 years.

As used herein, the term "synergistic" refers to a combination of therapies (e.g., prophylactic or therapeutic agents) which is more effective than the additive effects of any two or more single therapies (e.g., one or more prophylactic or therapeutic agents). A synergistic effect of a combination of therapies (e.g., a combination of prophylactic or therapeutic agents) permits the use of lower dosages of one or more of therapies (e.g., one or more prophylactic or therapeutic agents) and/or less frequent administration of said therapies to a subject with a condition (e.g., an equine influenza virus infection or a condition or symptom associated therewith, an infection other than an equine influenza virus infection or a condition or symptom associated therewith, an IFN treatable disease or a condition in which the attenuated equine influenza viruses can be used as a vector to induce an immune response to a particular antigen associated with the condition). The ability to utilize lower dosages of therapies (e.g., prophylactic or therapeutic agents) and/or to administer said therapies less frequently reduces the toxicity associated with the administration of said therapies to a subject without reducing the efficacy of said therapies in the prevention or treatment of a condition (e.g., an equine influenza virus infection or a condition or symptom associated therewith, an infection other than an equine influenza virus infection or a condition or symptom associated therewith, an IFN treatable disease or a condition in which the attenuated equine influenza viruses can be used as a vector to induce an immune response to a particular antigen associated with the condition). In addition, a synergistic effect can result in improved efficacy of therapies (e.g., prophylactic or therapeutic agents) in the prevention or treatment of a condition (e.g., an equine influenza virus infection or a condition or symptoms associated therewith, an infection other than an equine influenza virus infection or a condition or symptom associated therewith, an IFN treatable disease or a condition in which the attenuated equine influenza viruses can be used as a vector to induce an immune response to a particular antigen associated with the condition). Finally, synergistic effect of a combination of therapies (e.g., prophylactic or therapeutic agents) may avoid or reduce adverse or unwanted side effects associated with the use of any single therapy.

As used herein, the term "T cell receptor modulator" refers to an agent which modulates the phosphorylation of a T cell receptor, the activation of a signal transduction pathway associated with a T cell receptor and/or the expression of a particular protein such as a cytokine. Such an agent may directly or indirectly modulate the phosphorylation of a T cell receptor, the activation of a signal transduction pathway associated with a T cell receptor, and/or the expression of a particular protein such as a cytokine. Examples of T cell receptor modulators include, but are not limited to, peptides, polypeptides, proteins, fusion proteins and antibodies which immunospecifically bind to a T cell receptor or a fragment thereof. Further, examples of T cell receptor modulators include, but are not limited to, proteins, peptides, polypeptides (e.g., soluble T cell receptors), fusion proteins and antibodies that immunospecifically bind to a ligand for a T cell receptor or a fragment thereof.

As used herein, the term "therapeutically effective amount" refers to the amount of a therapy, which is sufficient to reduce the severity of a condition (e.g., an equine influenza virus infection or a condition associated therewith (e.g., influenza induced abortions, depression, inappetance, anorexia, dyspnea, myalgia, or enlarged submandibular lymph nodes), an infection other than an equine influenza virus infection or a condition or symptom associated therewith an IFN treatable disease or a condition in which the attenuated equine influenza viruses can be used as a vector to induce an immune response to a particular antigen associated with the condition), reduce the duration of a condition (e.g., equine influenza virus infection or a condition associated therewith, an infection other than an equine influenza virus infection or a condition or symptom associated therewith, an IFN treatable disease or a condition in which the attenuated equine influenza viruses can be used as a vector to induce an immune response to a particular antigen associated with the condition), reduce the titer of equine influenza virus or other virus, reduce the number of other pathogens, ameliorate one or more symptoms of a condition (e.g., an equine influenza virus infection or a condition associated therewith, an infection other than an equine influenza virus infection or a condition or symptom associated therewith, an IFN treatable disease or a condition in which the attenuated equine influenza viruses can be used as a vector to induce an immune response to a particular antigen associated with the condition), prevent the advancement of a condition (e.g., an equine influenza virus infection or a condition associated therewith, an infection other than an equine influenza virus infection or a condition or symptom associated therewith, an IFN treatable disease or a condition in which the attenuated equine influenza viruses can be used as a vector to induce an immune response to a particular antigen associated with the condition), cause regression of a condition (e.g., an equine influenza virus infection or a condition associated therewith, an infection other than an equine influenza virus infection or a condition or symptom associated therewith, an IFN treatable disease or a condition in which the attenuated equine influenza viruses can be used as a vector to induce an immune response to a particular antigen associated with the condition), or enhance or improve the therapeutic effect(s) of another therapy.

As used herein, the terms "therapies" and "therapy" can refer to any protocol(s), method(s), compositions, formulations and/or agent(s) that can be used in the prevention, treatment, management, or amelioration of a condition (e.g., an equine influenza virus infection or a condition or symptom associated therewith, an infection other than an equine influenza virus infection or a condition or symptom associated therewith, an IFN treatable disease or a condition in which the attenuated equine influenza viruses can be used as a vector to induce an immune response to a particular antigen associated with the condition). In certain embodiments, the terms "therapies" and "therapy" refer to biological therapy, supportive therapy, and/or other therapies useful in treatment, management, prevention, or amelioration of an equine influenza virus infection or a condition or symptom associated therewith, an infection other than an equine influenza virus infection or a condition or symptom associated therewith, an IFN treatable disease or a condition in which the attenuated equine influenza viruses can be used as a vector to induce an immune response to a particular antigen associated with the condition, known to one of skill in the art.

As used herein, the terms "therapeutic agent" and "therapeutic agents" refer to any agent(s) which can be used in the prevention, treatment, management, or amelioration of a condition or a symptom thereof (e.g., an equine influenza infection or a condition or symptoms associated therewith, an infection other than an equine influenza virus infection or a condition or symptom associated therewith, an IFN treatable disease or a condition in which the attenuated equine influenza viruses can be used as a vector to induce an immune response to a particular antigen associated with the condition). Preferably, a therapeutic agent is an agent which is known to be useful for, or has been or is currently being used for the prevention, treatment, management, or amelioration of an equine influenza virus infection or a condition or symptoms associated therewith, an infection other than an equine influenza virus infection or a condition or symptom associated therewith, an IFN treatable disease or a condition in which the attenuated equine influenza viruses can be used as a vector to induce an immune response to a particular antigen associated with the condition.

As used herein, the terms "treat," "treatment," and "treating" refer to the eradication or control of equine influenza virus replication or the replication of a pathogen (e.g., a virus) other than equine influenza virus, the reduction in the titer of equine influenza virus or virus other than equine influenza virus, the reduction in the numbers of a pathogen, the reduction or amelioration of the progression, severity, and/or duration of a condition (e.g., an equine influenza virus infection or a condition associated therewith, an infection other than an equine influenza virus infection or a condition or symptom associated therewith, an IFN treatable disease or a condition in which the attenuated equine influenza viruses can be used as a vector to induce an immune response to a particular antigen associated with the condition), or the amelioration of one or more symptoms resulting from the administration of one or more therapies (including, but not limited to, the administration of one or more prophylactic or therapeutic agents).

The term "tumor antigen" as used herein refers to a molecule on a tumor cell that can be specifically recognized by immune T cells or antibodies. A tumor antigen includes those present only on tumor cells (tumor specific antigens) as well as those present on normal cells but expressed preferentially or aberrantly on tumor cells (tumor associated antigens). Examples of tumor antigens include, but are not limited to, antigens of sarcoids, prostate cancer, fibrosarcoma, self-differentiation antigens such as oncofetal, or differentiation, antigens which are expressed by malignant cells, including but not limited to oncofetal antigens such as carcinoembryonio antigens (CEA) of the colon, alpha-fetoprotein, the human antigenic counterpart or functional equivalent of the 175 kDa murine antigen of transitional cell bladder carcinomas, the melanoma associated antigen p97 or GD3, and differentiation antigens of human lung carcinomas such as L6 and L20.

As used herein, the phrase "wild-type equine influenza virus" refers to the types of an equine virus that are prevalent, circulating naturally and producing typical outbreaks of disease in a host population before genetic manipulation or mutation. Examples of wild-type equine influenza viruses include, but are not limited to, A/Eq/KY/5/2002 (H3N8) and A/Eq/NY/73 (H7N7).

4. DESCRIPTION OF THE FIGURES

Figure 1B:
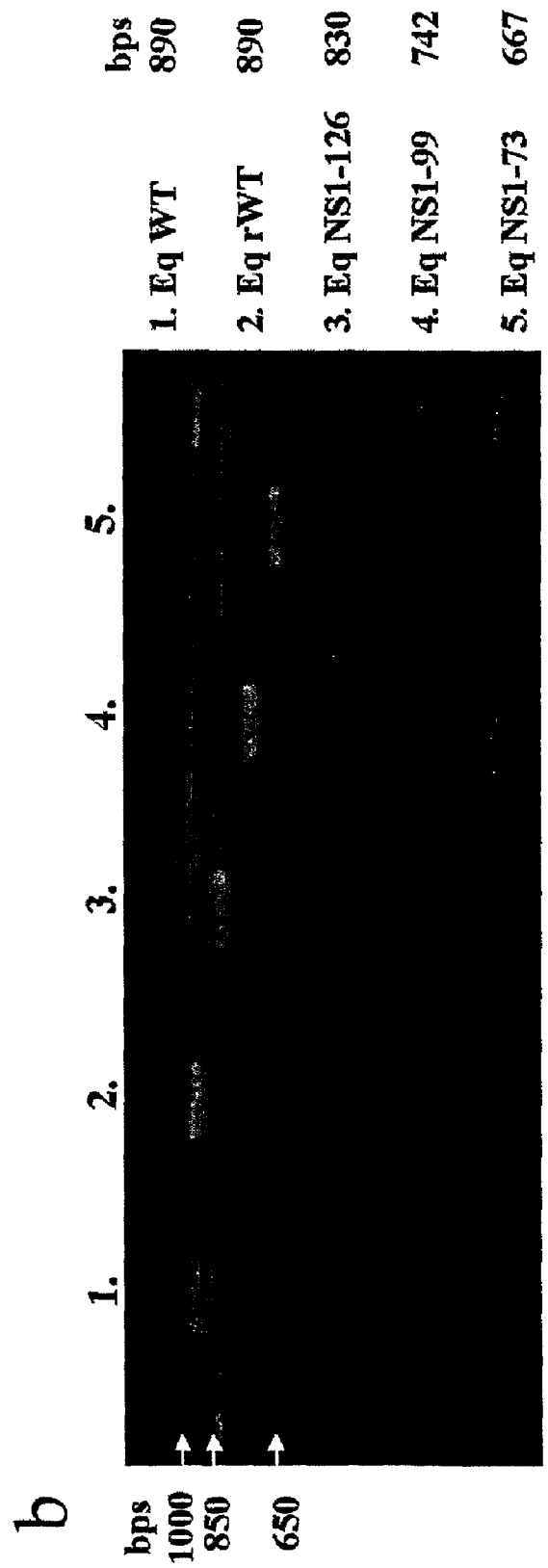

FIG. 1. Generation of equine influenza viruses with truncated NS1 proteins. (a) Schematic diagram of the wild-type and mutated NS1 influenza virus gene segments. The coding region of the A/eq/KY/5/02 NS segment is 219 amino acids long. C-terminal truncations were made to this segment resulting in three constructs encoding for the first 126, 99 or 73 amino acids of the NS1 protein. The nuclear export protein (NEP) open reading frame was not altered in these constructs. The underlined sequences (SEQ ID NOs: 21, 22 and 23, respectively) were introduced to generate stop codons and restriction sites in each construct. (b) RT-PCR of NS segments of wild-type and recombinant equine influenza viruses. RNA was extracted from allantoic fluid of HA-positive eggs. Sizes of the generated cDNAs confirmed the rescue of the specific viruses. The size of the DNA markers are indicated on the left side of the figure and the length of the RT-PCR products for each of the viruses are shown on the right.

Figure 2:
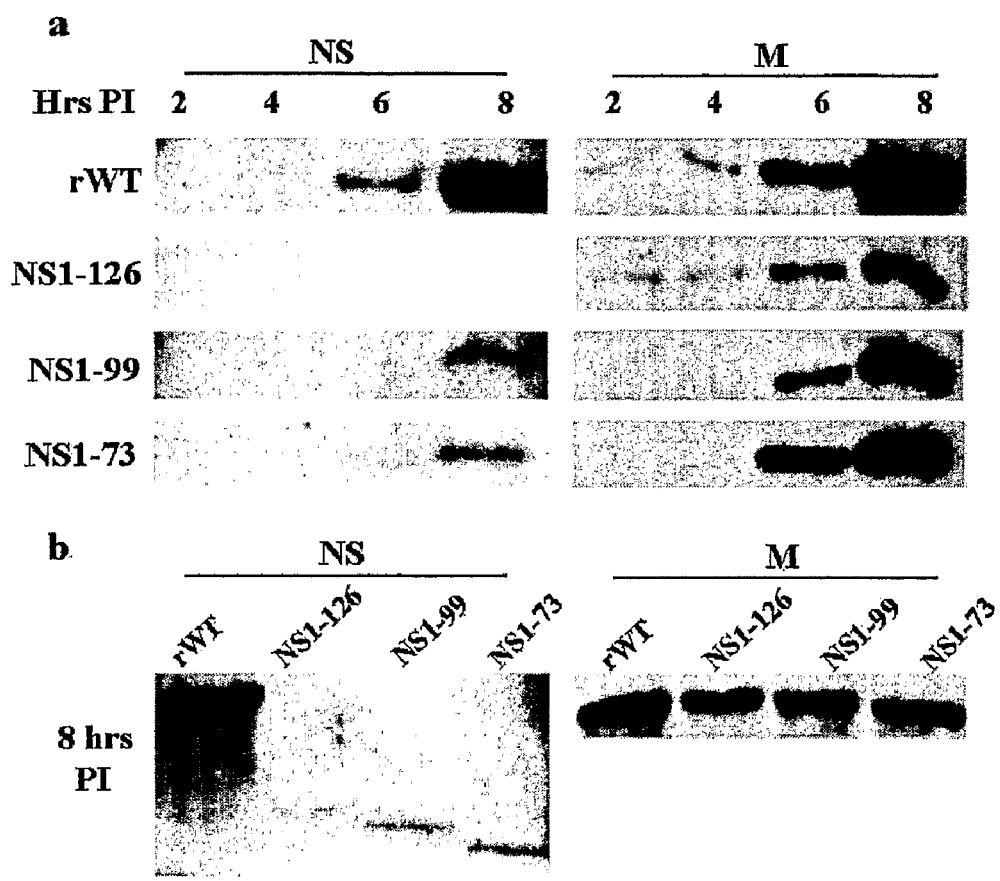

FIG. 2. Expression of NS1 proteins in MDCK cells. (a) Cells were infected with each of the recombinant viruses at a MOI of 1.5. Ten microliters of 1.4 mg/ml total protein was loaded onto a 12% SDS-polyacrylamide gel. Separated proteins were probed for analysis of the NS1 protein, with a rabbit polyclonal antibody generated against the first 73 amino acids of the protein. A mouse monoclonal antibody against the viral M1 protein was also included as a positive control to monitor viral infection. (b) Expression of NS1 proteins in MDCK cells. Cells were infected with each of the recombinant viruses at a MOI of 5. Twenty microliters of 2.0 mg/ml total protein was loaded onto a 12% SDS-polyacrylamide gel. Separated proteins were probed for analysis of the NS1 and M1 proteins.

Figure 3:
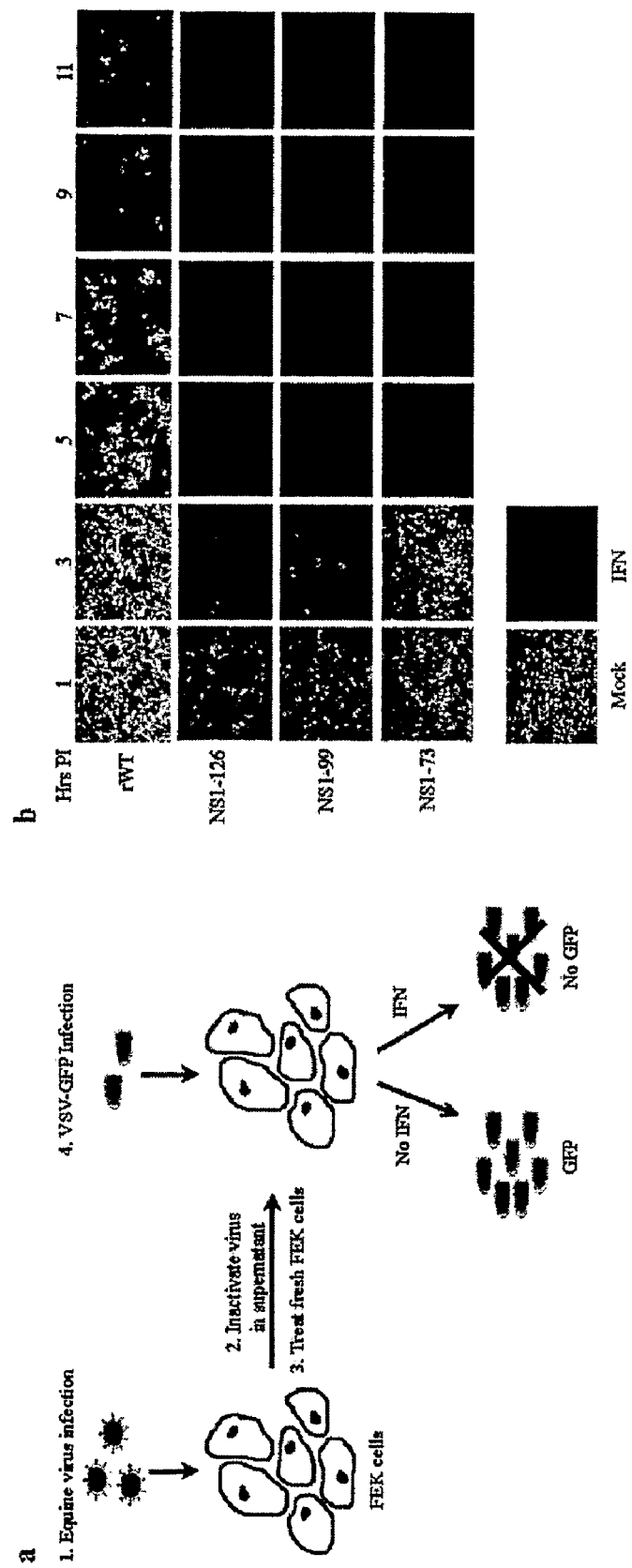

FIG. 3. Bioassay for production of IFN in FEK cells infected with recombinant wild-type and NS1 mutant viruses. (a) Schematic diagram of the bioassay for IFN production. FEK cells were infected with each of the four equine recombinant viruses. Supernatants were collected and any virus present was UV inactivated. Fresh FEK cells were treated with the inactivated supernatants and then infected with VSV-GFP at a MOI of 0.1. (b) Time course of IFN production. Over an 11 hour infection period, supernatants were taken at 2 hour intervals as indicated. VSV-GFP infected cells were examined by fluorescence microscopy and pictures of representative fields were taken.

Figure 4:
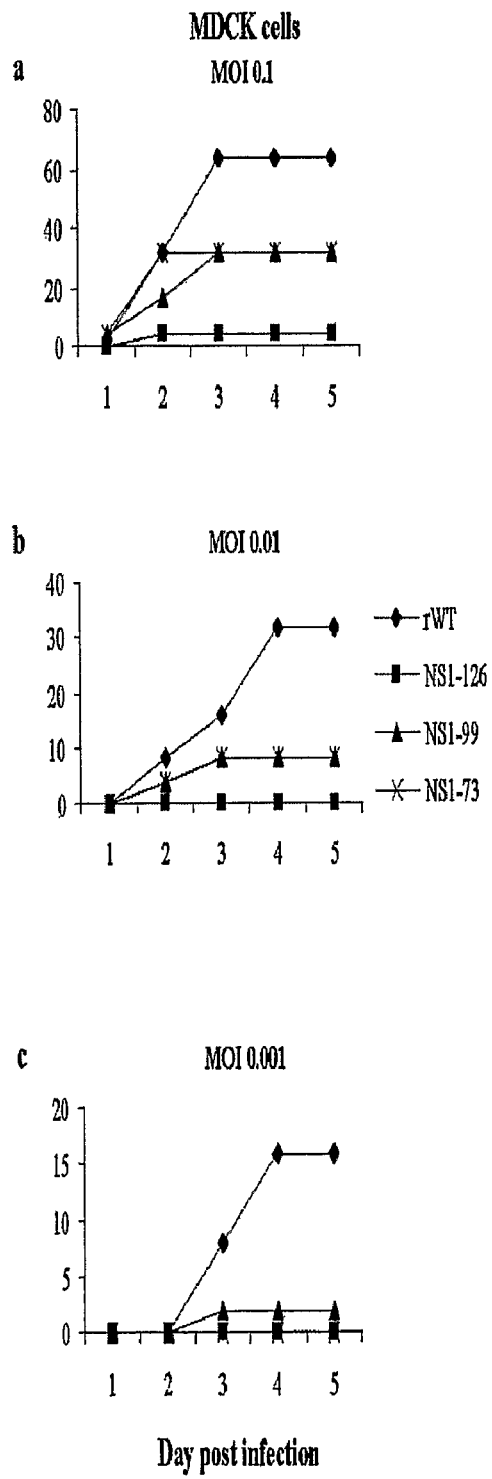

FIG. 4. Characterization of viral growth kinetics in MDCK cells. A comparison of viral growth kinetics for the recombinant wild-type and the three NS1 mutant viruses in MDCK cells. MDCK cells infected with each of the viruses at a MOI of 0.1 (a), a MOI of 0.01 (b) and a MOI of 0.001 (c). The viral growth in the supernatant of infected cells was examined daily for 5 days by hemagglutination assay.

Figure 5:
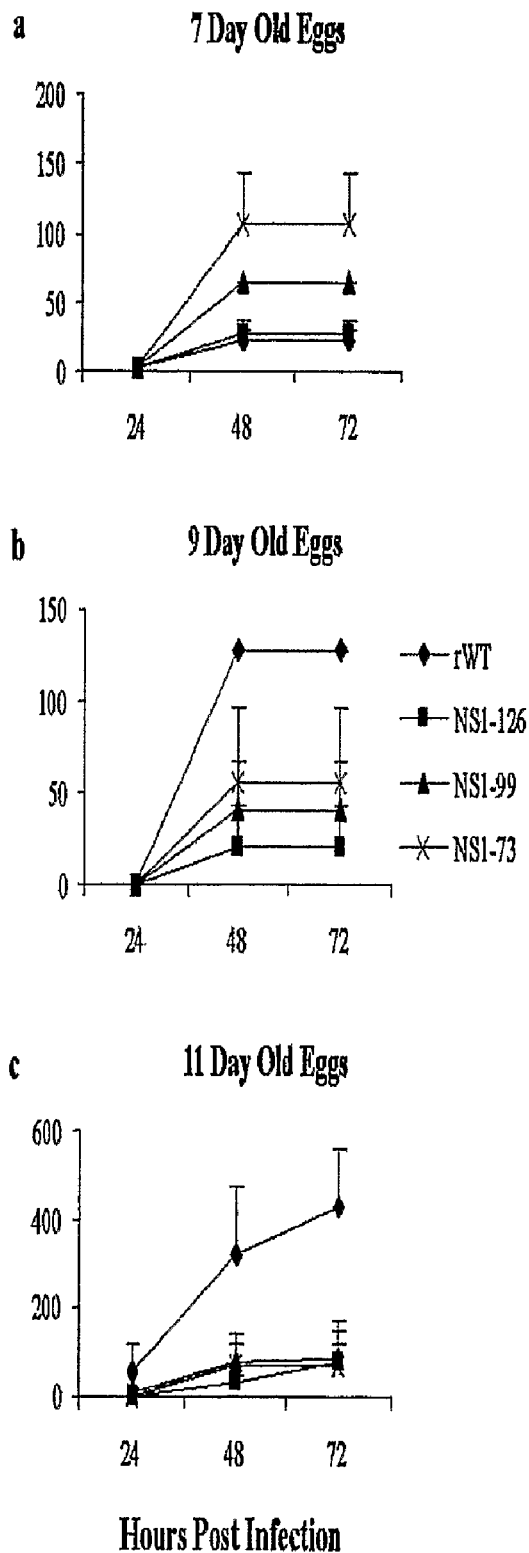

FIG. 5. Characterization of viral growth kinetics in embryonated hen eggs. The allantoic cavities of 7 (a), 9 (b) and 11 day old embryonated eggs (c) were infected with each of the recombinant equine viruses. The mean viral titer (±SEM) was determined by hemagglutination assay of allantoic fluid at 24, 48 and 72 hours post-infection.

Figure 6:
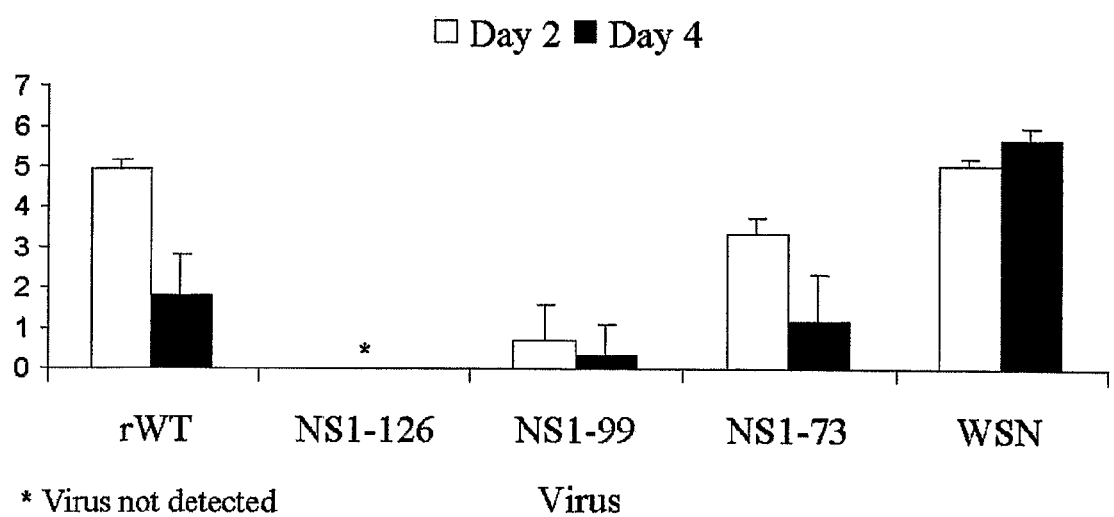

FIG. 6. Viral replication in mouse lungs. Six-week-old female C57/BL6 mice were infected intranasally with $1\times10^5$ PFU of each recombinant equine influenza virus and A/WSN/33 virus. Mice were sacrificed on days 2 and 4 post-infection and viral lung titers were determined by immunofluorescence in MDCK cells. The graph represents the mean viral titer (±SEM) for each group.

5. DETAILED DESCRIPTION OF THE INVENTION

The present invention provides attenuated equine influenza viruses having an impaired ability to antagonize the cellular interferon (IFN) response, methods for producing such attenuated equine influenza viruses, and the use of such viruses in vaccine and pharmaceutical formulations. Such viruses are capable of generating an immune response and creating immunity but not causing illness or causing fewer and/or less severe symptoms, i.e., the viruses have decreased virulence. Therefore, they are ideal candidates for live virus vaccines. Moreover, the attenuated viruses can induce a robust IFN response which has other biological consequences in vivo, affording protection against subsequent infectious diseases and/or inducing antitumor responses. Therefore, the attenuated viruses can be used pharmaceutically for the prevention or treatment of other infectious diseases and/or IFN-treatable diseases.

The invention is based, in part, on the Applicants' discovery that equine influenza viruses engineered to contain or containing a deletion(s) in the NS1 gene have impaired replication relative to wild-type equine influenza viruses. Surprisingly, and contrary to results seen with human influenza virus in mouse models, the length of the NS1 protein does not correlate with the level of attenuation of the equine influenza virus. Applicants have discovered that with equine influenza, a mutant virus with the shortest NS1 protein is the least attenuated. In other words, equine influenza viruses containing shorter deletions in the NS1 gene exhibit a greater attenuation in vivo than equine influenza viruses containing longer deletions in their NS1 gene, or wild-type equine influenza viruses. Applicants have further discovered that the recombinant equine influenza viruses are impaired in their ability to inhibit IFN production in vitro, and they do do not replicate as efficiently as the parental recombinant strain in embryonated hen eggs, in MDCK cells or in an in vivo mouse model. While not intending to be bound to any theory or explanation for the mechanism of action of the equine influenza virus NS1 deletion mutants in vivo, the attenuated features of such viruses are presumably due to their levels of NS1 protein expression, their ability to induce a robust cellular IFN response, and their impaired ability to antagonize such a response. However, the beneficial features of such viruses may not be solely attributable to their effect on the cellular interferon response. Indeed, alterations in other activities associated with NS1, such as, alteration of pre-mRNA splicing, inhibition of cellular mRNA polyadenylation, poly(A)-containing mRNA nucleocytoplasmic transport, and stimulation of viral protein synthesis, may contribute to the desired attenuated phenotype achieved by the introduction of mutations in the NS1 gene of equine influenza virus.

An attenuated equine influenza virus of the present invention comprises a mutation in an equine influenza NS1 gene that diminishes the ability of the NS1 gene product to antagonize the cellular interferon response. In one embodiment, an attenuated equine influenza virus of the invention comprises a genome comprising a mutation in an equine influenza virus NS1 gene that diminishes the ability of the NS1 gene product to antagonize a cellular interferon response, and permits the attenuated virus, at a multiplicity of infection (MOI) of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type equine influenza virus in cells (e.g., cells of human, mouse, chicken, rat, birds, horse (e.g., equine fetal kidney or equine dermal cells, etc.), as determined approximately 2 to 10 days, 3 to 7 days, 3 to 5 days, or 2, 3, 4, 5, 6, 7, 8, 9, 10 days post-infection when propagated under the same conditions. The titers of attenuated and wild-type equine influenza viruses can be determined utilizing any technique well-known in the art or described herein, (e.g., hemagglutination assays, plaque assays, egg infectious doses (EID50), tissue culture infectious doses (TCID50), etc.) and the viruses can be propagated under conditions described herein or well-known in the art (e.g., in horse cells, MDCK cells (e.g., in MBM, 10% v/v fetal calf serum (FCS), 1% penicillin/streptomycin at 37° C. in a 5% $CO_2$ humidified incubator) or embryonated chicken eggs (e.g., in a stationary incubator at 37° C. with 55% relative humidity). Alternatively, the viruses can be propagated in cells (e.g., in horse cells, MDCK cells, etc.) that are grown in serum-free or serum reduced (e.g., TPCK trypsin) medium.

In a specific embodiment, an attenuated equine influenza virus of the invention comprises a genome comprising a mutation in an equine influenza virus NS1 gene that diminishes the ability of the NS1 gene product to antagonize a cellular interferon response, and permits the attenuated virus, at a multiplicity of infection (MOI) of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type equine influenza virus in horse cells (e.g., equine dermal cells or equine fetal kidney cells (e.g., FEK or EFK-2 cells)), as determined approximately 2 to 10 days, 3 to 7 days, 3 to 5 days, or 2, 3, 4, 5, 6, 7, 8, 9, 10 days post-infection when propagated under the same conditions. The titers of attenuated and wild-type equine influenza viruses can be determined utilizing any technique well-known in the art or described herein, (e.g., hemagglutination assays, plaque assays, egg infectious doses (EID50), tissue culture infectious doses (TCID50), etc.) and the viruses can be propagated under conditions described herein or well-known in the art (e.g., in horse cells, MDCK cells (e.g., in MEM, 10% v/v fetal calf serum (FCS), 1% penicillin/streptomycin at 37° C. in a 5% $CO_2$ humidified incubator) or embryonated chicken eggs (e.g., in a stationary incubator at 37° C. with 55% relative humidity). Alternatively, the viruses can be propagated in cells (e.g., in horse cells, MDCK cells, etc.) that are grown in serum-free or serum reduced (e.g., TPCK trypsin) medium.

An attenuated equine influenza virus having the desired phenotype can itself be used as the active ingredient in vaccine, pharmaceutical or immunogenic formulations. Alternatively, the attenuated equine influenza virus can be used as the vector or "backbone" of recombinantly produced vaccines or immunogenic formulations. To this end, the "reverse genetics" technique can be used to engineer mutations or introduce foreign epitopes into the attenuated equine influenza virus, which would serve as the "parental" strain. In this way, vaccines can be designed for immunization against strain variants, or in the alternative, against completely different infectious agents or disease antigens (e.g., tumor antigens). For example, the attenuated virus can be engineered to express neutralizing epitopes of other preselected strains. Alternatively, epitopes of other viruses can be built into the attenuated equine influenza virus. Alternatively, epitopes of non viral infectious pathogens (e.g., parasites, bacteria, fungi) can be engineered into the attenuated equine influenza virus.

The present invention provides methods for vaccinating a subject comprising administering the vaccine formulations of the invention. In one embodiment, the present invention provides a method comprising administering to a subject an effective amount of a vaccine formulation of the invention. In certain embodiments, the dose of the vaccine formulation administered to the subject is between about $10^2$ to about $10^8$, about $10^3$ to about $10^7$, or about $10^4$ to about $5\times10^6$ pfu. In other embodiments, the dose of the vaccine formulation administered is $10^2$, $5\times10^2$, $10^3$, $5\times10^3$, $10^4$, $5\times10^4$, $10^5$, $5\times10^5$, $10^6$, $5\times10^6$, $10^7$, $5\times10^7$ or $10^8$ pfu. In other embodiments, the dose of an immunogenic formulation of the invention administered to a subject is $10^2$ to about $10^8$, about $10^3$ to about $10^7$, or about $10^4$ to about $5\times10^6$ pfu. In yet other embodiments, the dose of an immunogenic formulation of the invention administered to a subject is $10^2$, $5\times10^2$, $10^3$, $5\times10^3$, $10^4$, $5\times10^4$, $10^5$, $5\times10^5$, $10^6$, $5\times10^6$, $10^7$, $5\times10^7$ or $10^8$ pfu. In specific embodiments, the subject is a donkey, zebra, camel, dog, avian (e.g., a duck). In a preferred embodiment, the subject is a horse.

The present invention provides immunogenic formulations comprising an attenuated equine influenza virus of the invention and methods for inducing an immune response for the treatment, management or prevention of an equine influenza virus infection or a condition or symptom associated therewith, an infection other than an equine influenza virus infection or a condition or symptom associated therewith, or a condition in which the attenuated equine influenza viruses can be used as a vector to induce an immune response to a particular antigen associated with the condition, comprising administering to a subject an immunogenic formulation of the invention. In one embodiment, the present invention provides a method for inducing an immune response for the treatment, management or prevention of an equine influenza virus infection or a condition or symptom associated therewith, an infection other than an equine influenza virus infection or a condition or symptom associated therewith, or a condition in which the attenuated equine influenza viruses can be used as a vector to induce an immune response to a particular antigen associated with the condition, comprising administering to a subject an effective amount of an immunogenic formulation of the invention. In certain embodiments, the dose of the immunogenic formulation administered to the subject is between about $10^2$ to about $10^8$, about $10^3$ to about $10^7$, about $10^4$ to about $5\times10^6$ pfu or about $10^4$ to about $10^7$ pfu. In other embodiments, the dose of an immunogenic formulation of the invention administered to a subject is $10^2$, $5 \times 10^2$, $10^3$, $10^4$, $5 \times 10^4$, $10^5$, $5 \times 10^5$, $10^6$, $5 \times 10^6$, $10^7$, $5 \times 10^7$ or $10^8$ pfu. In specific embodiments, the subject is a donkey, zebra, camel, dog, avian (e.g., a duck). In a preferred embodiment, the subject is a horse.

The attenuated equine influenza viruses, which induce robust IFN responses in subjects, may also be used in pharmaceutical formulations for the prophylaxis or treatment of other infections, or IFN-treatable diseases such as cancer. In this regard, the tropism of the attenuated equine influenza virus can be altered to target the virus to a desired target organ, tissue or cells in vivo or ex vivo. Using this approach, the IFN response can be induced locally, at the target site, thus avoiding or minimizing the side effects of systemic IFN treatments. To this end, the attenuated equine influenza virus can be engineered to express a ligand specific for a receptor of the target organ, tissue or cells.

The present invention provides methods for preventing, managing or treating an infection or IFN-treatable disease in a subject, other than an equine influenza viral infection or IFN-treatable disease caused by equine influenza virus, comprising administering a pharmaceutical formulation of the invention. In one embodiment, the present invention provides a method for preventing, managing or treating an infection or IFN-treatable disease in a subject, other than an equine influenza viral infection or IFN-treatable disease caused by equine influenza virus, comprising administering an effective amount of a pharmaceutical formulation of the invention. In certain embodiments, the dose of the pharmaceutical formulation administered to the subject is between about $10^2$ to about $10^8$, about $10^3$ to about $10^7$, about $10^4$ to about $5 \times 10^6$ pfu or about $10^4$ to about $10^{12}$ pfu. In other embodiments, the dose of the pharmaceutical formulation administered to the subject is $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $5 \times 10^8$, $1 \times 10^9$, $5 \times 10^9$, $1 \times 10^{10}$, $5 \times 10^{10}$, $1 \times 10^{11}$, $5 \times 10^{11}$ or $10^{12}$ pfu. In specific embodiments, the subject is a donkey, zebra, camel, dog, avian (e.g., a duck). In a preferred embodiment, the subject is a horse.

The present invention provides methods for preventing, managing or treating cancer in a subject comprising administering a pharmaceutical formulation of the invention. In one embodiment, the present invention provides a method for preventing, managing or treating cancer in a subject comprising administering an effective amount of a pharmaceutical formulation of the invention. In certain embodiments, the dose of the pharmaceutical formulation administered to the subject is between about $10^2$ to about $10^8$, about $10^3$ to about $10^7$, about $10^4$ to about $5 \times 10^6$ pfu. In other embodiments, the dose of the pharmaceutical formulation administered to the subject is $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $5 \times 10^8$, $1 \times 10^9$, $5 \times 10^9$, $1 \times 10^{10}$, $5 \times 10^{10}$, $1 \times 10^{11}$, $5 \times 10^{11}$ or $10^{12}$ pfu. In specific embodiments, the subject is a donkey, zebra, camel, dog, avian (e.g., a duck). In a preferred embodiment, the subject is a horse.

Applicants demonstrated that attenuated equine influenza viruses with impaired interferon antagonist activity were shown to replicate in vivo generating titers that are lower than than detected with wild-type equine influenza viruses, but that are sufficient to induce immunological and cytokine responses. Thus, mutations which diminish but do not abolish the IFN antagonist activity of the equine influenza virus are preferred for vaccine formulations. Such viruses can be selected for growth in both conventional and non conventional substrates, and for intermediate virulence.

The present invention provides cells containing (alternatively, comprising) equine influenza viruses of the present invention. In a specific embodiment, a cell contains/comprises an equine influenza virus that is genetically engineered. In certain embodiments, the attenuated equine influenza virus contained in the cell is engineered to encode an epitope derived from another virus or a tumor antigen. In accordance with this embodiment, the genome of the attenuated equine influenza virus may comprise at least one segment derived from a different virus. Any cell can be infected with, contain or comprise an attenuated equine influenza virus of the invention including, but not limited to, MDCK cells, Vero cells, primary human umbilical vein endothelial cells (HUVEC), H292 human epithelial cell line, HeLa cells, equine dermal cells and equine fetal kidney cells (e.g., FEK or EFK-2 cells). In a preferred embodiment, the cell is a horse cell or a horse cell line. In certain embodiments, the cell (e.g., a horse cell or horse cell line) is interferon-deficient.

The invention encompasses the use of substrates such as cells, cell lines and embryonated eggs, to propagate the attenuated equine influenza viruses of the invention. In one embodiment, the invention provides methods for vaccine production, immunogenic formulation production and pharmaceutical production comprising propagating in a substrate an attenuated equine influenza virus of the present invention and collecting progeny virus, wherein the substrate is a cell, cell line or embryonated egg. In certain embodiments, the substrate is an IFN deficient system. Exemplary IFN-deficient systems include, but are not limited to, young embryonated eggs (e.g., 6 to 10 days old, 6 to 9 days old, 6 to 8 days old or 6 to 7 days old embryonated eggs), IFN deficient cell lines (such as VERO cells or genetically engineered cell lines such as STAT1 knockouts). Embryonated eggs or cell lines pretreated with compounds that inhibit the IFN system (including drugs, antibodies, antisense, ribozymes, etc.) can also be used as an IFN-deficient system. Further, eggs deficient in the IFN system, e.g., eggs produced by STAT1 negative birds, especially fowl, including but not limited to transgenic chickens, ducks or turkeys, may be used as an IFN-deficient system.

5.1 Generation of Mutants with Altered IFN Antagonist Activity

Any mutant equine influenza virus or strain which has a decreased IFN antagonist activity can be selected and used in accordance with the invention. In one embodiment, naturally occurring mutants or variants, or spontaneous equine influenza mutants can be selected that have an impaired ability to antagonize the cellular IFN response. In another embodiment, mutant equine influenza viruses can be generated by exposing the virus to mutagens, such as ultraviolet irradiation or chemical mutagens, or by multiple passages and/or passage in non permissive hosts. Screening in a differential growth system can be used to select for those mutants having impaired IFN antagonist function. Since equine influenza virus A has a segmented genome, the attenuated phenotype can be transferred to another strain having a desired antigen by reassortment, (i.e., by coinfection of the attenuated virus and the desired strain, and selection for reassortants displaying both phenotypes). In a specific embodiment, the equine influenza viruses of the invention are not naturally occurring viruses. In another specific embodiment, the equine influenza viruses of the invention are genetically engineered viruses. In yet another specific embodiment, an equine influenza virus with naturally occurring mutations in the NS1 gene are not encompassed by the invention. In yet another specific embodiment, known equine influenza viruses with mutations in the NS1 gene are not encompassed by the invention. In specific embodiments, the equine influenza viruses of the invention contain all or a portion of the NS1 gene derived from human or swine influenza viruses.

Mutations can be engineered into equine influenza virus using "reverse genetics" approaches. In this way, natural or other mutations which confer the attenuated phenotype can be engineered into vaccine strains. For example, deletions, insertions or substitutions of the coding region of the equine influenza virus gene for IFN antagonist activity (i.e., the NS1 of equine influenza virus) can be engineered. Deletions, substitutions or insertions in the non coding region of the equine influenza virus gene responsible for IFN antagonist activity are also contemplated. To this end, mutations in the signals responsible for the transcription, replication, polyadenylation and/or packaging of the gene responsible or the IFN antagonist activity can be engineered. Such mutations, for example to the promoter, could down regulate the expression of the equine influenza virus gene responsible for IFN antagonist activity. Mutations in the promoter can be made, for example, by promoter shuffling (e.g., of the influenza B virus promoter), or in the noncoding regions of the NS1 gene. Mutations in equine influenza virus genes which may regulate the expression of the equine influenza virus gene responsible for IFN antagonist activity (i.e., the equine influenza virus NS1 gene) are also within the scope of viruses that can be used in accordance with the invention.

The present invention also provides equine influenza viruses comprising genomes comprising mutations to the NS1 gene segment that may not result in an altered IFN antagonist activity or an IFN-inducing phenotype but rather results in altered viral functions and an attenuated phenotype, e.g., altered inhibition of nuclear export of poly(A) containing mRNA, altered inhibition of pre mRNA splicing, altered inhibition of the activation of PKR by sequestering of dsRNA, altered effect on translation of viral RNA and altered inhibition of polyadenylation of host mRNA (e.g., see Krug in Textbook of Influenza, Nicholson et al. Ed. 1998, 82 92, and references cited therein).

The reverse genetics technique involves the preparation of synthetic recombinant viral RNAs that contain the non coding regions of the equine influenza virus RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO97/12032 published Apr. 3, 1997; WO96/34625 published Nov. 7, 1996; in European Patent Publication EP A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 475A1 published Jun. 25, 1997, each of which is incorporated by reference herein in its entirety.

The helper free plasmid technology can also be utilized to engineer an attenuated equine influenza virus. For a description of helper-free plasmid technology see, e.g., International Publication No. WO 01/04333; U.S. Pat. No. 6,649,372; Fodor et al., 1999, J. Virol. 73:9679-9682; Hoffmann et al., 2000, Proc. Natl. Acad. Sci. USA 97:6108-6113; and Neumann et al., 1999, Proc. Natl. Acad. Sci. USA 96:9345-9350, which are incorporated herein by reference in their entireties.

Attenuated viruses generated by the reverse genetics approach or helper-free plasmid technology can be used in the vaccine, immunogenic and pharmaceutical formulations described herein. Reverse genetics techniques or helper-free plasmid technology can also be used to engineer additional mutations to other viral genes important for vaccine, immunogenic and pharmaceutical formulation production—i.e., the epitopes of useful vaccine strain variants can be engineered into the attenuated equine influenza virus. Alternatively, completely foreign epitopes, including antigens derived from other viral or non viral pathogens can be engineered into the attenuated strain. For example, antigens of non related viruses, parasite antigens, bacterial or fungal antigens or tumor antigens can be engineered into the attenuated strain (e.g., epitopes of Equine Reovirus (Orbivirus), Arteritis Virus, Equine Herpes Virus (EHV1, EHV2, EHV3, EHV4 and EHV5), Equine Papova Virus, Retrovirus, Adenovirus, African Horse Sickness Virus, Shipping Fever Virus, West Nile Virus, Equine Encephalitis Virus, Vesicular Stomatitis Virus (VSV), Equine Rhinovirus, and Hendra Virus), and antigenic determinants of non viral equine pathogens such as bacteria, including, but not limited to, *Clostridia* sp., *Salmonella* sp., *E. coli*, *Streptococcus equi*, *Taylorella equigenitalis* (CEM), *Klebsiella pneumoniae* and *Pseudomonas aeruginosa*, *Dermatophilus congolensis*, or a tumor antigen such as carcinoembryonic antigen (CEA), breast cancer antigen such as EGFR (Epidermal growth factor receptor), HER2 antigen (p185$^{HER2}$), HER2 neu epitope, cancer antigen-50 (CA-50), cancer antigen 15-3 (CA15-3) associated with breast cancer, carcinoma associated antigen (CAA), melanoma antigen, and melanoma associated antigens 100, 25, and 150). Alternatively, epitopes which alter the tropism of the virus in vivo can be engineered into the chimeric attenuated viruses of the invention.

In a specific embodiment, a combination of reverse genetics techniques or helper-free plasmid technology and reassortant techniques can be used to engineer attenuated viruses having the desired epitopes in equine influenza viruses. For example, an attenuated equine influenza virus (generated by, e.g., reverse genetics techniques, helper-free plasmid technology or a combination thereof) and a strain carrying the desired vaccine epitope (generated by, e.g., natural selection, mutagenesis, by reverse genetics techniques, helper-free plasmid technology or a combination thereof) can be co infected in hosts that permit reassortment of the segmented genomes. Reassortants that display both the attenuated phenotype and the desired epitope can then be selected. In a particular embodiment, reassortment techniques can be used to transfer the attenuated phenotype from a parental equine influenzae virus strain (a natural mutant, a mutagenized virus, or a genetically engineered virus) to a different virus strain (a wild-type virus, a natural mutant, a mutagenized virus, or a genetically engineered virus).

In a specific embodiment, the present invention provides an attenuated equine influenza virus comprising a genome comprising a mutation in the equine influenza virus NS1 gene that diminishes the ability of the NS1 gene product to antagonize a cellular interferon response. In accordance with this embodiment, the attenuated equine influenza virus is preferably genetically engineered.

The attenuated equine influenza viruses of the invention may have one or more or a combination of any of the following characteristics: the ability to induce interferon activity at a level less than (e.g., 5%, 10%, 15%, 20%, 25%, 30%, 35%, 40%, 45%, 50%, 55%, 60%, 65%, 70%, 75%, 80%, 85%, 90%, 95% or 98% less than) that of wild-type equine influenza virus, e.g., A/Eq/KY/5/02, as measured by standard interferon assays; a viral titer 1 to 50, 2 to 25, 2 to 10 or 3 to 7 fold lower than wild-type equine influenza virus, e.g., A/Eq/KY/5/02, when grown under the same conditions (e.g., inoculated at a MOI of 0.0001, 0.0005, 0.001, 0.005, 0.01, 0.05, 0.1, 0.5, 1, 5 or 10 and grown in FEK cells or EFK-2 cells and assayed in MDCK cells); a viral titer 1 to 10 fold, 1 to 5 fold, 5-10 fold, 10 to 500, 20 to 250, 20 to 100 or 40 to 80 fold lower than wild-type equine influenza virus, e.g., A/Eq/KY/5/02, when isolated from BALF of infected horses as assayed in a plaque assay performed on MDCK cells; or a reduced ability to cause lung lesions in infected horses.

In a specific embodiment, an attenuated equine influenza virus of the invention comprises a genome comprising a mutation in an equine influenza virus NS1 gene that diminishes the ability of the NS1 gene product to antagonize a cellular interferon response, and permits the attenuated virus, at a MOI of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type equine influenza virus in horse cells (e.g., FEK cells or EFK-2 cells) as determined by a hemagglutination assay of BALF obtained from horses or supernatants of horse cells approximately 2 to 10 days, 3 to 7 days, 3 to 5 days, or 2, 3, 5, 6, 7, 8, 9, 10 days post-infection or when the viruses are plaqued on MDCK cells. In one embodiment, the growth of an attenuated equine influenza virus of the invention is compared to a particular standard or reference, e.g., wild-type equine influenza virus A/Eq/KY/5/02. In accordance with these embodiments, the attenuated virus may be genetically engineered to contain or express non-equine influenza virus nucleic acid sequences such, e.g., an epitope of a foreign pathogen or a tumor antigen. Preferably, the non-equine influenza virus sequences do not include a nucleic acid sequence that alters the attenuated phenotype of the virus. Accordingly, nucleic acid sequences encoding proteins, polypeptides or peptides with interferon antagonizing activity are preferably not engineered into equine influenza virus.

The invention provides attenuated equine influenza viruses comprising a genome comprising at least two, at least three, at least four or more mutations in two, three, four or more equine influenza virus genes, wherein at least one of the mutations is in the NS1 gene and contributes to or is responsible (directly or indirectly) for the attenuation of the virus and/or the diminished ability of the virus to antagonize a cellular interferon response. In a specific embodiment, an attenuated equine influenza virus of the invention comprises a genome comprising at least two, at least three, at least four or more mutations in two, three, four or more equine influenza virus genes, wherein at least one of the mutations is in the NS1 gene and is responsible for the diminished ability of the NS1 gene product to antagonize cellular interferon response, and permits the attenuated virus, at a MOI of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type equine influenza virus, e.g., A/Eq/KY/5/02, in horse cells, as determined by, e.g., hemagglutination assays, approximately 2 to 10 days, 3 to 7 days, or 2, 3, 5, 6, 7, 8, 9, 10 days post-infection when the viruses are propagated under the same conditions. In another embodiment, an attenuated equine influenza virus of the invention comprises a genome comprising at least two, three, four or more mutations in two, three, four or more equine influenza virus genes, wherein at least one of the mutations is in the NS1 gene and is responsible for the attenuation of the virus, and permits the attenuated virus, at a MOI of between 0.0005 and 0.001, 0.001 and 0.01, 0.01 and 0.1, or 0.1 and 1, or a MOI of 0.0005, 0.0007, 0.001, 0.005, 0.01, 0.05, 0.1, 0.5, 1.0, 1.5, 2.0, 2.5, 3.0, 3.5, 4.0, 4.5, 5.0, 5.5, or 6.0, to grow to titers between approximately 1 to approximately 100 fold, approximately 5 to approximately 80 fold, approximately 20 to approximately 80 fold, or approximately 40 to approximately 80 fold, approximately 1 to approximately 10 fold, approximately 1 to approximately 5 fold, approximately 1 to approximately 4 fold, approximately 1 to approximately 3 fold, approximately 1 to approximately 2 fold, or approximately 1, 2, 3, 4, 5, 6, 7, 8, 10, 15, 20, 25, 30, 35, 40, 45, 50, 55, 60, 65, 70, 75, 80, 85, 90, 95 or 100 fold lower than wild-type equine influenza virus, e.g., A/Eq/KY/5/02, in horse cells, as determined by, e.g., hemagglutination assays, approximately 2 to 10 days, 3 to 7 days, 3 to 5 days, or 2, 3, 5, 6, 7, 8, 9, 10 days post-infection when the viruses are propagated under the same conditions (e.g., in MDCK cells). In accordance with these embodiments, the attenuated virus have an impaired interferon antagonist phenotype and the viruses may be genetically engineered to contain or express non-equine influenza virus nucleic acid sequences, such as, e.g., an epitope of a foreign pathogen (e.g., epitopes of Equine Reovirus (Orbivirus), Arteritis Virus, Equine Herpes Virus (EHV1, EHV2, EHV3, EHV4 and EHV5), Equine Papova Virus, Retrovirus, Adenovirus, African Horse Sickness Virus, Shipping Fever Virus, West Nile Virus, Equine Encephalitis Virus, Vesicular Stomatitis Virus (VSV), Equine Rhinovirus, and Hendra Virus), and antigenic determinants of non viral pathogens such as bacteria and parasites, to name but a few) or a tumor antigen. Preferably, the non-equine influenza virus sequences (heterologous sequences) do not include a nucleic acid sequence that alters the attenuated phenotype of the virus. Accordingly, nucleic acid sequences encoding proteins, polypeptides or peptides with interferon antagonizing activity are preferably not engineered into the equine influenza virus.

Any mutation that results in the desired phenotype (preferably, an impaired ability to antagonize a cellular interferon response) can be introduced into the equine influenza virus NS1 gene. Examples of the types of mutations that can be included in or introduced into equine influenza virus NS1 gene include, but are not limited to, deletions, substitutions, insertions and combinations thereof. One or more mutations can be located anywhere throughout the NS1 gene (e.g., the amino-terminus, the carboxy-terminus or somewhere in between) and/or the regulatory element of the NS1 gene. In a specific embodiment, an attenuated equine influenza virus of the invention comprises a genome comprising an equine influenza virus NS1 gene with a mutation (e.g., a deletion or substitution) at the amino-terminus. In a preferred embodiment, an attenuated equine influenza virus of the invention comprises a genome comprising an equine influenza virus with a mutation (e.g., a deletion or substitution, preferably a deletion) at the carboxy-terminus. In another embodiment, an attenuated equine influenza virus of the invention comprises a genome comprising a mutation in an equine influenza virus NS1 gene resulting in a deletion consisting of 5, preferably 10, 15, 20, 25, 30, 35, 40, 45, 50, 55, 60, 65, 70, 73, 75, 80, 85, 90, 95, 99, 100, 105, 110, 115, 120, 125, 126, 130, 135, 140, 145, 150, 155, 160, 165, 170 or 175 amino acid residues from the carboxy terminus of NS1, or a deletion of between 5-170, 25-170, 50-170, 100-170, 100-160 or 105-160 amino acid residues from the carboxy-terminus. In another embodiment, an attenuated equine influenza virus of the invention comprises a genome comprising a mutation in an equine influenza virus NS1 gene resulting in a deletion of all amino acid residues except amino acid residues 1-126, amino acid residues 1-120, amino acid residues 1-115, amino acid residues 1-110, amino acid residues 1-100, amino acid residues 1-99, amino acid residues 1-95, amino acid residues 1-85, amino acid residues 1-80, amino acid residues 1-75, amino acid residues 1-73, amino acid residues 1-70, amino acid residues 1-65 or amino acid residues 1-60, wherein the amino terminal amino acid is number 1. In accordance with these embodiments, the attenuated equine influenza virus is preferably genetically engineered. In a preferred embodiment, an attenuated equine influenza virus of the invention is Eq-NS1-126, Eq-NS1-99 or Eq-NS1-73.

The attenuated equine influenza virus of the present invention may be a chimeric virus that expresses a heterologous sequence, e.g., antigens of other vaccine strains (e.g., using reverse genetics, reassortment or helper-free plasmid technology). Alternatively, the attenuated influenza viruses may be engineered, using reverse genetics, reassortment or helper-free plasmid technology with genetically engineered viruses, to express completely foreign epitopes, e.g., antigens of other infectious pathogens, tumor antigens, or targeting antigens. In certain embodiments, the attenuated equine influenza viruses express a heterologous sequence derived from other equine infectious agents, non-equine infectious agents, equine or other types of tumor antigens (e.g., equine sarcoid Mc1 ($P_{55}$ or $P_{124}$), horse prostate kallikrein (HPK), carcinoembryonic antigen (CEA), breast cancer antigen such as EGFR (epidermal growth factor receptor), HER2 antigen ($p_{185}^{HER2}$), HER2 neu epitope, cancer antigen-50 (CA-50), cancer antigen 15-3 (CA15-3) associated with breast cancer, carcinoma associated antigen (CAA), melanoma antigen, and melanoma associated antigens 100, 25, and 150). In other embodiments, the attenuated equine influenza virus of the present invention may contain a segment derived from another virus. Since the NS RNA segment is the shortest among the eight viral RNAs, it is possible that the NS RNA will tolerate longer insertions of heterologous sequences than other viral genes. Moreover, the NS RNA segment directs the synthesis of high levels of protein in infected cells, suggesting that it would be an ideal segment for insertions of foreign antigens. Exemplary sequences include epitopes of foreign pathogens, (e.g., epitopes of Equine Reovirus (Orbivirus), Arteritis Virus, Equine Herpes Virus (EHV1, EHV2, EHV3, EHV4 and EHV5), Equine Papova Virus, Retrovirus, Adenovirus, African Horse Fever Virus, Vesicular Stomatitis Virus (VSV), Equine Rhinovirus, and Hendra Virus), and antigenic determinants of non viral equine pathogens such as bacteria, including, but not limited to, *Clostridia* sp., *Salmonella* sp., *E. coli*, *Streptococcus equi*, *Taylorella equigenitalis* (CEM), *Klebsiella pneumoniae* and *Pseudomonas aeruginosa*, *Dermatophilus congolensis*).

Preferably, the heterologous sequence is not a nucleic acid sequence that alters the attenuated phenotype of the virus. Accordingly, preferably, nucleic acid sequences encoding proteins, polypeptides or peptides with interferon antagonizing activity are not engineered into the equine influenza virus. In certain embodiments, the chimeric virus expresses a tumor antigen. In other embodiments, the chimeric virus expresses an epitope of a foreign pathogen.

5.2 Selection of Attenuated Equine Influenza Viruses

The invention encompasses methods of selecting equine influenza viruses which have the desired phenotype, i.e., attenuated equine influenza viruses or equine influenza viruses which have low IFN activity (i.e., a reduction of 5-10%, 10-20%, 20-30%, 30-40%, 40-50%, 50-60%, 60-70%, 70-80%, 80-90% or more when compared to wild-type equine influenza viruses, e.g., A/Eq/KY/5/02, under the same conditions) or no IFN antagonist activity whether obtained from natural variants, spontaneous variants (i.e., variants which evolve during virus propagation), mutagenized natural variants, reassortants and/or genetically engineered viruses (see, e.g., U.S. Pat. No. 6,635,416). Such viruses can be best screened in differential growth assays that compare growth in IFN deficient versus IFN competent host systems. Viruses which demonstrate better growth in the IFN deficient systems versus IFN competent systems are selected; preferably, viruses which grow to titers at least one log, at least two logs, three logs, or 1 to 50, 1 to 25, 1 to 20, 1 to 10 or 1 to 5 logs greater in IFN deficient systems as compared to an IFN competent system are selected. Exemplary IFN-deficient systems include, but are not limited to, young embryonated eggs (e.g., 6 to 10 days old, 6 to 9 days old, 6 to 8 days old or 6 to 7 days old embryonated eggs), IFN deficient cell lines (such as VERO cells or genetically engineered cell lines such as STAT1 knockouts, PKR knockouts, etc.). Embryonated eggs or cell lines pretreated with compounds that inhibit the IFN system (including drugs, antibodies, antisense, ribozymes, etc.) can also be used as an IFN-deficient system. Further, eggs deficient in the IFN system, e.g., eggs produced by STAT1 negative birds, especially fowl, including but not limited to transgenic chickens, ducks or turkeys, may be used as an IFN-deficient system. Attenuated equine influenza viruses showing at least 1 to 50, 1 to 25, 1 to 20, 1 to 10 or 1 to 5 logs lower titers in 10 days old eggs versus 6-7, 6-8, or 6-9 days old eggs will be considered impaired in their ability to inhibit the IFN response.

For purposes of screening, transient IFN deficient systems can be used in lieu of genetically manipulated systems. For example, the host system can be treated with compounds that inhibit IFN production and/or components of the IFN response (e.g., drugs, antibodies against IFN, antibodies against IFN receptor, inhibitors of PKR, antisense molecules and ribozymes, etc.). Growth of attenuated equine influenza virus can be compared in IFN competent untreated controls versus IFN deficient treated systems.

Growth of equine influenza virus (as measured by titer) can, e.g., be compared in a variety of cells, cell lines, or animal model systems that express IFN and the components of the IFN response, versus cells, cell lines, or animal model systems deficient for IFN or components of the IFN response. Techniques which are well known in the art for the propagation of viruses in cell lines can be used (see, for example, the working examples infra). Growth of equine influenza virus in an IFN competent cell line versus an IFN deficient genetically engineered cell line can be compared.

The equine influenza viruses can be screened using IFN assay systems e.g., transcription based assay systems in which reporter gene expression is controlled by an IFN responsive promoter. Reporter gene expression in infected versus uninfected cells can be measured to identify viruses which efficiently induce an IFN response, but which are unable to antagonize the IFN response. For example, test cells can be engineered to transiently or constitutively express reporter genes such as luciferase reporter gene or chloramphenicol transferase (CAT) reporter gene under the control of an interferon stimulated response element, such as the IFN stimulated promoter of the ISG 54K gene (Bluyssen et al., 1994, Eur. J. Biochem. 220:395 402). Cells are infected with the test equine influenza virus and the level of expression of the reporter gene compared to that in uninfected cells or cells infected with wild type equine influenza virus. An increase in the level of expression of the reporter gene following infection with the test attenuated equine influenza virus would indicate that the test equine influenza virus is inducing an IFN response. Alternatively, the induction of IFN responses may be determined by measuring IFN dependent transcriptional activation following infection with the test attenuated equine influenza virus. The expression of genes known to be induced by IFN, e.g., Mx, PKR, 2 5 oligoadenylatesynthetase, major histocompatibility complex (MHC) class I, etc., can be analyzed by techniques known to those of skill in the art (e.g., northern blots, western blots, PCR, etc.). The induction of IFN responses may also be determined by measuring the phosphorylated state of components of the IFN pathway following infection with a test equine influenza virus, e.g., IRF 3, which is phosphorylated in response to double stranded RNA. In response to type I IFN, Jak1 kinase and TyK2 kinase, subunits of the IFN receptor, STAT1, and STAT2 are rapidly tyrosine phosphorylated. Thus, in order to determine whether the equine influenza virus induces IFN responses, cells, such as 293 cells, are infected with the test mutant virus and following infection, the cells are lysed. IFN pathway components, such as Jak1 kinase or TyK2 kinase, are immunoprecipitated from the infected cell lysates, using specific polyclonal sera or antibodies, and the tyrosine phosphorylated state of the kinase is determined by immunoblot assays with an anti-phosphotyrosine antibody (e.g., see Krishnan et al. 1997, Eur. J. Biochem. 247: 298 305). An enhanced phosphorylated state of any of the components of the IFN pathway following infection with the equine influenza virus would indicate induction of IFN responses by the equine influenza virus.

Further, the induction of IFN responses following infection with a test equine influenza virus may be determined by measuring the ability to bind specific DNA sequences or the translocation of transcription factors induced in response to viral infection, e.g., IRF3, STAT1, STAT2, etc. In particular, STAT1 and STAT2 are phosphorylated and translocated from the cytoplasm to the nucleus in response to type I IFN. The ability to bind specific DNA sequences or the translocation of transcription factors can be measured by techniques known to those of skill in the art, e.g., electromobility gel shift assays, cell staining, etc. Other assays that can be used are described in U.S. patent application Ser. No. 09/829,711, herein incorporated by reference in its entirety. In a preferred embodiment, however, differential growth assays are used to select viruses having the desired phenotype, since the host system used (IFN competent versus IFN deficient) applies the appropriate selection pressure.

The attenuated equine influenza viruses of the present invention are optimally screened in horse cells, including primary, secondary horse cells and horse cell lines. Any horse cell which is capable of growing equine influenza virus can be used. Representative horse cells include, but are not limited to, equine dermal cells or equine fetal kidney cells (e.g., FEK cells or EFK-2 cells).

The equine influenza viruses of the invention can be screened in horse cells by comparison to wild-type equine influenza viruses, e.g., A/Eq/KY/5/02, under the same growth conditions. Attenuated equine influenza viruses are selected based on characteristics such as slower growth rates, fewer lung lesions upon infection of horses, reduced viral titers in bronchoalveolar lavage fluid (BALF) and reduced detection of virus on nasal swabs when compared to wild-type equine influenza virus. Such attenuated equine influenza viruses have decreased virulence because they have a reduced ability to replicate in interferon competent systems compared to wild-type equine influenza viruses but can generate an immune response.

Horse cells can be infected with wild-type equine influenza viruses, e.g., A/Eq/KY/5/02, and NS1 mutants at a specific MOI and viral titers in the supernatant can be determined at specific times post-infection. Infection of horse cells at MOIs from between 0.0005 and 0.001, 0.001 and 0.01, 0.01 and 0.1, 0.1 and 1, or 1 and 10, or a MOI of 0.0005, 0.001, 0.005, 0.01, 0.05, 0.1, 0.5, 1, 5 or 10 can be used. In one embodiment, an MOI of 0.001 is used. Viral titers can be determined from approximately 2 to 10 days, 3 to 7 days, 3 to 5 days, or 2, 3, 4, 5, 6, 7, 8, 9 or 10 days post-infection. In a specific embodiment, viral titers are determined 5 days post-infection. After growing virus in horse cells, viral titers can be assessed in the supernatant. Any system for measuring titers of influenza virus can be used. Representative systems are described in Section 5.7. In a particular embodiment, viral titers in the supernatant are determined by plaquing various time points on MDCK cells.

The selection systems of the invention encompass measuring IFN induction by determining whether an extract from the cell or egg infected with the test attenuated equine influenza virus is capable of conferring protective activity against viral infection. More specifically, groups of 10 day old embryonated chicken eggs are infected with the test mutant equine influenza virus or the wild type equine influenza virus. Approximately 15 to 20 hours post infection, the allantoic fluid is harvested and tested for IFN activity by determining the highest dilution with protective activity against equine influenza virus infection in tissue culture cells.

The pathogenesis of mutant equine influenza viruses of the invention can also be assessed in horses in vivo. Useful assays include assessing lung lesions in lung lobes, nasal swabs and determination of viral titers in bronchoalveolar lavage fluid (BALF) by any method known in the art.

5.3 Propagation of Attenuated Equine Influenza Virus

The present invention provides methods for propagating attenuated equine influenza viruses in cells (e.g., horse cells), embryonated eggs, and animals. The attenuated equine influenza viruses of the present invention can be propagated in any substrate that allows the virus to grow to titers that permit a use of the attenuated equine influenza virus described herein. In a specific embodiment, the attenuated equine influenza viruses of the present invention are propagated in any substrate that allows the virus to grow to titers comparable to those determined for wild-type equine influenza virus strains in IFN-competent substrates. In another embodiment, the attenuated equine influenza viruses of the invention are propagated in IFN-deficient substrates. Substrates which are useful for selection of the attenuated equine influenza viruses of the invention do not have to be used for propagation and vice versa.

In accordance with the methods of the present invention, the attenuated equine influenza viruses which may be grown in cells (e.g., horse cells), embryonated eggs, and animals are selected from naturally occurring strains, variants or mutants, mutagenized virus, reassortants and/or genetically engineered viruses. The methods of the present invention encompass growing the attenuated equine influenza viruses, preferably using appropriate growth conditions (see e.g., growth conditions set forth in Section 6 below), and collecting the progeny virus.

In a specific embodiment, the attenuated equine influenza viruses of the invention are propagated in horse cells. In accordance with this embodiment, the horse cells may or may not be IFN-deficient or produce lower levels of IFN. Representative horse cells include, but are not limited to, FEK or EFK-2 cells.

In certain embodiments, the invention provides methods of propagating the attenuated equine influenza viruses of the invention in embryonated eggs, e.g., from 6 to 14 days old. In other embodiments, young or immature embryonated eggs can be used to propagate attenuated equine influenza viruses of the invention. In accordance with the present invention, immature embryonated eggs encompass eggs which are less than ten day old eggs, preferably six to nine day old eggs, six to eight day old, six to seven day old eggs or six days old eggs. Immature embryonated eggs of the present invention also encompass eggs which artificially mimic immature eggs up to, but less than ten day old, as a result of alterations to the growth conditions, e.g., changes in incubation temperatures; treating with drugs; or any other alteration which results in an egg with a retarded development, such that the IFN system is not fully developed as compared with ten to twelve day old eggs. The equine influenza viruses can be propagated in different locations of the embryonated egg, e.g., the allantoic cavity. In certain embodiments, the embryonated eggs are chick eggs.

The invention also encompasses methods and IFN deficient substrates for the growth and isolation of attenuated equine influenza viruses of the present invention. See, e.g., U.S. Pat. No. 6,573,079, which is expressly incorporated by reference in its entirety. IFN deficient substrates which can be used to support the growth of the attenuated equine influenza viruses include, but are not limited to, naturally occurring cells, cell lines, embryonated eggs, and IFN-deficient systems, e.g., Vero cells, young embryonated eggs; recombinant cells or cell lines that are engineered to be IFN deficient, e.g., IFN deficient cell lines derived from STAT1 knockouts, IRF3 knockouts, IRF7 knockouts, PKR knockouts, etc.; embryonated eggs obtained from IFN deficient birds, especially fowl (e.g., chickens, ducks, turkeys) including flock that are bred to be IFN deficient or transgenic birds (e.g., STAT1 knockouts). In certain embodiments, the IFN-deficient substrate is not Vero cells and/or not a STAT1 deficient cell line.

The host system, cells, cell lines, eggs or animals can be genetically engineered to express transgenes encoding inhibitors of the IFN system, e.g., dominant negative mutants, such as STAT1 lacking the DNA binding domain, antisense RNA, ribozymes, inhibitors of IFN production, inhibitors of IFN signaling, and/or inhibitors of antiviral genes induced by IFN. It should be recognized that animals that are bred or genetically engineered to be IFN deficient will be somewhat immunocompromised, and should be maintained in controlled, disease free environment. Thus, appropriate measures (including the use of dietary antibiotics) should be taken to limit the risk of exposure to infectious agents of transgenic IFN deficient animals, such as mice, flocks of breeding hens, ducks, turkeys etc. Alternatively, the host system, e.g., cells, cell lines, eggs or animals can be treated with a compound which inhibits IFN production and/or the IFN pathway e.g., drugs, antibodies, antisense molecules, ribozyme molecules targeting the STAT1 gene, and/or antiviral genes induced by IFN.

The present invention encompasses methods of growing and isolating equine influenza viruses having altered IFN antagonist activity in cells and cell lines which naturally do not have an IFN pathway or have a deficient IFN pathway or have a deficiency in the IFN system e.g., low levels of IFN expression as compared to wild type cells. In a particular embodiment, the present invention encompasses methods of growing the attenuated equine influenza viruses of the invention in equine dermal cells or equine fetal kidney cells (e.g., FEK or EFK-2 cells), Vero cells, or IFN-compromised embryonated eggs (e.g., immature embryonated eggs such as 6-, 7- or 8-day old embryonated eggs). In another embodiment, the present invention encompasses methods of growing the attenuated equine influenza viruses of the invention in cells where the cells are not Vero cells.

The present invention provides methods of growing and isolating the equine influenza viruses of the invention from a genetically engineered IFN deficient substrate. The present invention encompasses transgenic horses and avians in which a gene essential to the IFN system is mutated, e.g., STAT1, which would lay eggs that are IFN deficient. The present invention further encompasses avian transgenics which express dominant negative transcription factors, e.g., STAT1 lacking the DNA binding domain, ribozymes, antisense RNA, inhibitors of IFN production, inhibitors of IFN signaling, and inhibitors of antiviral genes induced in response to IFN.

The invention provides recombinant cell lines or animals, in particular horses and avians, in which one or more genes essential for IFN synthesis, the IFN pathway, and/or an antiviral gene induced by IFN, e.g., interferon receptor, STAT1, PKR, IRF3, IRF7, etc. has been mutated (e.g., disrupted, i.e., is a "knockout"). The recombinant animal can be any animal (such as a mouse, a horse or an avian, e.g., chicken, turkey, hen, duck, etc. (see, e.g., Sang, 1994, Trends Biotechnol. 12:415; Perry, et al., 1993, Transgenic Res. 2:125; Stern, C. D., 1996, Curr Top Microbiol Immunol 212:195 206; and Shuman, 1991, Experientia 47:897 for reviews regarding the production of avian transgenics each of which is incorporated by reference herein in its entirety)). In a specific embodiment, the recombinant animal is a horse. Such a cell line or animal can be generated by any method known in the art for disrupting a gene on the chromosome of the cell or animal. Such techniques include, but are not limited to pronuclear microinjection (Hoppe & Wagner, 1989, U.S. Pat. No. 4,873,191); retrovirus mediated gene transfer into germ lines (Van der Putten et al., 1985, Proc. Natl. Acad. Sci., USA 82:6148 6152); gene targeting in embryonic stem cells (Thompson et al., 1989, Cell 56:313); electroporation of embryos (Lo, 1983, Mol Cell. Biol. 3:1803); and sperm mediated gene transfer (Lavitrano et al., 1989, Cell 57:717); etc. For a review of such techniques, see Gordon, 1989, Transgenic Animals, Intl. Rev. Cytol. 115:171, which is incorporated by reference herein in its entirety.

In particular, a STAT1 knockout animal can be produced by promoting homologous recombination between a STAT1 gene in its chromosome and an exogenous STAT1 gene that has been rendered biologically inactive (preferably by insertion of a heterologous sequence, e.g., an antibiotic resistance gene). Homologous recombination methods for disrupting genes in the mouse genome are described, for example, in Capecchi (1989, Science 244:1288) and Mansour et al. (1988, Nature 336:348 352).

Briefly, all or a portion of a STAT1 genomic clone is isolated from genomic DNA from the same species as the knock out cell or animal. The STAT1 genomic clone can be isolated by any method known in the art for isolation of genomic clones (e.g., by probing a genomic library with a probe derived from a STAT1 sequence such as horse STAT1 (Genbank Accession Nos. AB116564 and NM_213769) and those sequences provided in see Meraz et al. 1996, Cell 84: 431 442; Durbin et al. 1996, Cell 84: 443 450, and references cited therein). Once the genomic clone is isolated, all or a portion of the clone is introduced into a recombinant vector. Preferably, the portion of the clone introduced into the vector contains at least a portion of an exon of the STAT1 gene, i.e., contains a STAT1 protein coding sequence. A sequence not homologous to the STAT1 sequence, preferably a positive selectable marker, such as a gene encoding an antibiotic resistance gene, is then introduced into the STAT1 gene exon. The selectable marker is preferably operably linked to a promoter, more preferably a constitutive promoter. The non homologous sequence is introduced anywhere in the STAT1 coding sequence that will disrupt STAT1 activity, e.g., at a position where point mutations or other mutations have been demonstrated to inactivate STAT1 protein function. For example, but not by way of limitation, the non homologous sequence can be inserted into the coding sequence for the portion of the STAT1 protein containing all or a portion of the kinase domain (e.g., the nucleotide sequence coding for at least 50, 100, 150, 200 or 250 amino acids of the kinase domain).

The positive selectable marker is preferably a neomycin resistance gene (neo gene) or a hygromycin resistance gene (hygro gene). The promoter may be any promoter known in the art; by way of example the promoter may be the phosphoglycerate kinase (PGK) promoter (Adra et al., 1987, Gene 60:65 74), the PolII promoter (Soriano et al, 1991, Cell 64:693 701), or the MC1 promoter, which is a synthetic promoter designed for expression in embryo derived stem cells (Thomas & Capecchi, 1987, Cell 51:503 512). Use of a selectable marker, such as an antibiotic resistance gene, allows for the selection of cells that have incorporated the targeting vector (for example, the expression of the neo gene product confers resistance to G418, and expression of the hygro gene product confers resistance to hygromycin).

In a preferred embodiment, a negative selectable marker for a counterselection step for homologous, as opposed to non homologous, recombination of the vector is inserted outside of the STAT1 genomic clone insert. For example, such a negative selectable marker is the HSV thymidine kinase gene (HSV-tk), the expression of which makes cells sensitive to ganciclovir. The negative selectable marker is preferably under the control of a promoter such as, but not limited to the PGK promoter, the PolII promoter or the MC1 promoter.

When homologous recombination occurs, the portions of the vector that are homologous to the STAT1 gene, as well as the non homologous insert within the STAT1 gene sequences, are incorporated into the STAT1 gene in the chromosome, and the remainder of the vector is lost. Thus, since the negative selectable marker is outside the region of homology with the STAT1 gene, cells in which homologous recombination has occurred (or their progeny), will not contain the negative selectable marker. For example, if the negative selectable marker is the HSV tk gene, the cells in which homologous recombination has occurred will not express thymidine kinase and will survive exposure to ganciclovir. This procedure permits the selection of cells in which homologous recombination has occurred, as compared to non homologous recombination in which it is likely that the negative selectable marker is also incorporated into the genome along with the STAT1 sequences and the positive selectable marker. Thus, cells in which non homologous recombination has occurred would most likely express thymidine kinase and be sensitive to ganciclovir.

Once the targeting vector is prepared, it is linearized with a restriction enzyme for which there is a unique site in the targeting vector, and the linearized vector is introduced into embryo derived stem (ES) cells (Gossler et al., 1986, Proc. Natl. Acad. Sci. USA 83:9065 9069) by any method known in the art, for example by electroporation. If the targeting vector includes a positive selectable marker and a negative, counterselectable marker, the ES cells in which homologous recombination has occurred can be selected by incubation in selective media. For example, if the selectable markers are the neo resistance gene and the HSV tk gene, the cells are exposed to G418 (e.g., approximately 300 µg/ml) and ganciclovir (e.g., approximately 2 µM).

Any technique known in the art for genotyping, for example but not limited to Southern blot analysis or the polymerase chain reaction, can be used to confirm that the disrupted STAT1 sequences have homologously recombined into the STAT1 gene in the genome of the ES cells. Because the restriction map of the STAT1 genomic clone is known and the sequence of the STAT1 coding sequence is known (see Meraz et al. 1996, Cell 84:431, Durbin et al. 1996, Cell 84:443 450, all references cited therein), the size of a particular restriction fragment or a PCR amplification product generated from DNA from both the disrupted and non disrupted alleles can be determined. Thus, by assaying for a restriction fragment or PCR product, the size of which differs between the disrupted and non disrupted STAT1 gene, one can determine whether homologous recombination has occurred to disrupt the STAT1 gene.

The ES cells with the disrupted STAT1 locus can then be introduced into blastocysts by microinjection and then the blastocysts can be implanted into the uteri of pseudopregnant mice using routine techniques. The animal that develop from the implanted blastocysts are chimeric for the disrupted allele. The chimeric males can be crossed to females, and this cross can be designed such that germline transmission of the allele is linked to transmission of a certain coat color. The germline transmission of the allele can be confirmed by Southern blotting or PCR analysis, as described above, of genomic DNA isolated from tissue samples.

Any gene whose product is important for interferon regulation can be used. Other mutations in the interferon pathway which may be used in accordance with the present invention include kinase deficient versions of Jak1, TyK2 or transcription factors lacking DNA binding domains STAT1, and STAT2 (see, e.g., Krishnan et al., 1997, Eur. J. Biochem. 247: 298 305).

For virus isolation, the attenuated equine influenza virus is removed from cell culture and separated from cellular components, typically by well known clarification procedures, e.g., such as gradient centrifugation and column chromatography, and may be further purified as desired using procedures well known to those skilled in the art, e.g., plaque assays.

5.4 Uses of Attenuated Viruses

The attenuated equine influenza viruses of the invention can be used as viral vectors for production of heterologous proteins as described in U.S. Pat. No. 5,820,871, which is herein incorporated by reference in its entirety.

The attenuated equine influenza viruses of the invention can be used in screening assays to identify viral proteins with interferon antagonizing function, for identifying viral proteins that have the ability to complement replication of an attenuated virus with impaired ability to antagonize cellular interferon responses and screening assays to identify antiviral agents which inhibit interferon antagonist activity and inhibit viral replication as described in U.S. Pat. No. 6,635,416, which is herein incorporated by reference in its entirety.

The attenuated equine influenza viruses of the invention can be used to produce antibodies which can be used in diagnostic immunoassays, passive immunotherapy, and generation of antiidiotypic antibodies. For example, an attenuated equine influenza virus comprising a genome comprising a mutation in the NS1 gene and a heterologous sequence (e.g., a tumor antigen) can be administered to a subject (e.g., a horse) to generate antibodies which can then be isolated and used in diagnostic assays, passive immunotherapy and generation of antiidiotypic antibodies. The generated antibodies may be isolated by standard techniques known in the art (e.g., immunoaffinity chromatography, centrifugation, precipitation, etc.) and used in diagnostic immunoassays, passive immunotherapy and generation of antiidiotypic antibodies. The isolated antibodies before being used in passive immunotherapy may be modified, e.g., the antibodies may be chimerized or humanized. See, e.g., U.S. Pat. Nos. 4,444,887 and 4,716,111; and International Publication Nos. WO 98/46645, WO 98/50433, WO 98/24893, WO98/16654, WO 96/34096, WO 96/33735, and WO 91/10741; each of which is incorporated herein by reference in its entirety, for reviews on the generation of chimeric and humanized antibodies.

The antibodies isolated from subjects administered an attenuated equine influenza virus of the invention may also be used to monitor treatment and/or disease progression. Any immunoassay system known in the art may be used for this purpose including but not limited to competitive and noncompetitive assay systems using techniques such as radioimmunoassays, ELISA (enzyme linked immunosorbent assays), "sandwich" immunoassays, precipitin reactions, gel diffusion precipitin reactions, immunodiffusion assays, agglutination assays, complement fixation assays, immunoradiometric assays, fluorescent immunoassays, proteinA immunoassays and immunoelectrophoresis assays, to name but a few.

The antibodies generated by the attenuated equine influenza viruses of the invention can also be used in the production of antiidiotypic antibody. The antiidiotypic antibody can then in turn be used for immunization, in order to produce a subpopulation of antibodies that bind the initial antigen of the pathogenic microorganism (Jerne, 1974, Ann. Immunol. (Paris) 125c:373; Jerne et al., 1982, EMBO J. 1:234).

In immunization procedures, the amount of immunogen to be used and the immunization schedule will be determined by a physician skilled in the art and will be administered by reference to the immune response and antibody titers of the subject.

5.5 Vaccine Formulations/Immunogenic Formulations

The invention encompasses vaccine formulations and immunogenic formulations comprising an attenuated equine influenza virus having an impaired ability to antagonize the cellular IFN response (i.e., equine influenza viruses with mutations in the NS1 gene that impair the ability of the virus to induce a cellular IFN response), and a suitable excipient. The attenuated equine influenza virus used in the vaccine formulation or immunogenic formulation may be selected from naturally occurring mutants or variants, mutagenized viruses or genetically engineered viruses. In a preferred embodiment, the attenuated equine influenza virus is genetically engineered. In another preferred embodiment, the attenuated equine influenza virus is isolated or purified. Attenuated strains of equine influenza viruses can also be generated via reassortment techniques, helper-free plasmid technology or by using a combination of the reverse genetics approach or helper-free plasmid technology and reassortment techniques. Naturally occurring variants include viruses isolated from nature as well as spontaneous occurring variants generated during virus propagation, having an impaired ability to antagonize the cellular IFN response. The attenuated equine influenza virus can itself be used as the active ingredient in the vaccine formulation or immunogenic formulation. Alternatively, the attenuated equine influenza virus can be used as the vector or "backbone" of recombinantly produced vaccines or immunogenic formulations. To this end, recombinant techniques such as reverse genetics (or, for segmented viruses, combinations of the reverse genetics and reassortment techniques) may be used to engineer mutations or introduce foreign antigens into the attenuated equine influenza virus used in the vaccine formulation or immunogenic formulation. In this way, vaccines can be designed for immunization against strain variants, or in the alternative, against completely different infectious agents or disease antigens.

Virtually any heterologous gene sequence may be constructed into the attenuated equine influenza viruses of the invention for use in vaccines or immunogenic formulations. Preferably, epitopes that induce a protective immune response to any of a variety of pathogens, or antigens that bind neutralizing antibodies may be expressed by or as part of the viruses. For example, heterologous gene sequences that can be constructed into the viruses of the invention for use in vaccines and immunogenic formulations include but are not limited to antigenic determinants of non viral pathogens such as bacteria and parasites. In another embodiment, all or portions of immunoglobulin genes may be expressed. For example, variable regions of anti-idiotypic immunoglobulins that mimic such epitopes may be constructed into the viruses of the invention. In yet another embodiment, tumor associated antigens may be expressed. Examples of tumor antigens include, but are not limited to, KS ¼ pan-carcinoma antigen, ovarian carcinoma antigen (CA125), prostatic acid phosphate, prostate specific antigen, melanoma-associated antigen p97, melanoma antigen gp75, high molecular weight melanoma antigen (HMW-MAA), prostate specific membrane antigen, carcinoembryonic antigen (CEA), polymorphic epithelial mucin antigen, milk fat globule antigen, colorectal tumor-associated antigens (such as: CEA, TAG-72, CO17-1A; GICA 19-9, CTA-1 and LEA), Burkitt's lymphoma antigen-38.13, CD19, B-lymphoma antigen-CD20, CD33, melanoma specific antigens (such as ganglioside GD2, ganglioside GD3, ganglioside GM2, ganglioside GM3), tumor-specific transplantation type of cell-surface antigen (TSTA) (such as virally-induced tumor antigens including T-antigen DNA tumor viruses and Envelope antigens of RNA tumor viruses), oncofetal antigen-alpha-fetoprotein such as CEA of colon, bladder tumor oncofetal antigen, differentiation antigen (such as human lung carcinoma antigen L6 and L20), antigens of fibrosarcoma, leukemia T cell antigen-Gp37, neoglycoprotein, sphingolipids, breast cancer antigens (such as EGFR (Epidermal growth factor receptor), HER2 antigen (p185$^{HER2}$) and HER2 neu epitope), polymorphic epithelial mucin (PEM), malignant human lymphocyte antigen-APO-1, differentiation antigen (such as I antigen found in fetal erythrocytes, primary endoderm, I antigen found in adult erythrocytes, preimplantation embryos, I(Ma) found in gastric adenocarcinomas, M18, M39 found in breast epithelium, SSEA-1 found in myeloid cells, VEP8, VEP9, Myl, VIM-D5, $D_1$56-22 found in colorectal cancer, TRA-1-85 (blood group H), C14 found in colonic adenocarcinoma, F3 found in lung adenocarcinoma, AH6 found in gastric cancer, Y hapten, $Le^y$ found in embryonal carcinoma cells, TL5 (blood group A), EGF receptor found in A431 cells, $E_1$ series (blood group B) found in pancreatic cancer, FC10.2 found in embryonal carcinoma cells, gastric adenocarcinoma antigen, CO-514 (blood group $Le^a$) found in Adenocarcinoma, NS-10 found in adenocarcinomas, CO-43 (blood group $Le^b$), G49 found in EGF receptor of A431 cells, MH2 (blood group $ALe^b/Le^y$) found in colonic adenocarcinoma, 19.9 found in colon cancer, gastric cancer mucins, $T_5A_7$ found in myeloid cells, $R_{24}$ found in melanoma, 4.2, $G_{D3}$, D1.1, OFA-1, $G_{M2}$, OFA-2, $G_{D2}$, and M1:22:25:8 found in embryonal carcinoma cells, and SSEA-3 and SSEA-4 found in 4 to 8-cell stage embryos), T cell receptor derived peptide from a Cutaneous T cell Lymphoma, C-reactive protein (CRP), cancer antigen-50 (CA-50), cancer antigen 15-3 (CA15-3) associated with breast cancer, cancer antigen-19 (CA-19) and cancer antigen-242 associated with gastrointestinal cancers, carcinoma associated antigen (CAA), chromogranin A, epithelial mucin antigen (MC5), human epithelium specific antigen (BEA), Lewis(a)antigen, melanoma antigen, melanoma associated antigens 100, 25, and 150, mucin-like carcinoma-associated antigen, multidrug resistance related protein (MRPm6), multidrug resistance related protein (MRP41), Neu oncogene protein (C-erbB-2), neuron specific enolase (NSE), P-glycoprotein (mdr1 gene product), multidrug-resistance-related antigen, p170, multidrug-resistance-related antigen, prostate specific antigen (PSA), CD56, and NCAM.

Either a live recombinant equine influenza virus vaccine or immunogenic formulation or an inactivated recombinant equine influenza virus vaccine or immunogenic formulation can be formulated. An equine influenza virus can be inactivated by methods well known to those of skill in the art. Common methods use formalin and heat for inactivation. See, e.g., U.S. Pat. No. 6,635,246, which are incorporated by reference in its entirety. Other methods include those described in U.S. Pat. Nos. 5,891,705; 5,106,619 and 4,693,981, herein incorporated by reference in their entireties.

A live vaccine or immunogenic formulation may be preferred because multiplication in the host leads to a prolonged stimulus of similar kind and magnitude to that occurring in natural infections, and therefore, confers substantial, long lasting immunity. Production of such live recombinant equine influenza virus vaccine formulations and immunogenic formulations may be accomplished using conventional methods involving propagation of the equine influenza virus in cell culture or in the allantois of the chick embryo followed by purification. Moreover, the attenuated equine influenza viruses can induce a robust IFN response which has other biological consequences in vivo, affording protection against subsequent infectious diseases and/or inducing antitumor responses.

Vaccine formulations and immunogenic formulations may include genetically engineered equine influenza influenza viruses that have mutations in the NS1 gene including but not limited to the truncated NS1 influenza mutants described in the working examples, infra. They may also be formulated using natural variants. When formulated as a live virus vaccine, a range of about $10^2$ to $10^8$ can be used, preferably from about $10^3$ to $10^7$, more preferably $10^4$ pfu to about $5\times10^6$, and most preferably from $10^4$ to $10^7$ pfu per dose should be used.

In certain embodiments, equine influenza virus contain mutations to the NS1 gene segment that may not result in an altered IFN antagonist activity or an IFN-inducing phenotype but rather result in altered viral functions and an attenuated phenotype e.g., altered inhibition of nuclear export of poly (A)-containing mRNA, altered inhibition of pre mRNA splicing, altered inhibition of the activation of PKR by sequestering of dsRNA, altered effect on translation of viral RNA and altered inhibition of polyadenylation of host mRNA (e.g., see Krug in Textbook of Influenza, Nicholson et al. Ed. 1998, 82-92, and references cited therein).

Many methods may be used to introduce the vaccine formulations and immunogenic formulations described above, these include but are not limited to intranasal, intratracheal, oral, intradermal, intramuscular, intraperitoneal, intravenous, and subcutaneous routes. It may be preferable to introduce the equine influenza virus vaccine formulation or immunogenic formulation via the natural route of infection of the pathogen for which the vaccine is designed, or via the natural route of infection of the wild-type virus. Where a live attenuated equine influenza virus vaccine preparation or immunogenic formulation is used, it may be preferable to introduce the formulation via the natural route of infection for influenza virus. The ability of influenza virus to induce a vigorous secretory and cellular immune response can be used advantageously. For example, infection of the respiratory tract by attenuated equine influenza viruses may induce a strong secretory immune response, for example in the urogenital system, with concomitant protection against a particular disease causing agent.

In a specific embodiment, it may be desirable to administer the compositions of the invention locally to the area in need of treatment; this may be achieved by, for example, and not by way of limitation, local infusion during surgery, by injection, by means of a catheter, or by means of an implant, said implant being of a porous, non-porous, or gelatinous material, including membranes, such as sialastic membranes, or fibers. In one embodiment, administration can be by direct injection at the site (or former site) or infection.

A vaccine or immunogenic formulation of the present invention, comprising $10^2$ to $10^8$ can be used, preferably from about $10^3$ to $10^7$, more preferably $10^4$ pfu to about $5\times10^6$ pfu of attenuated equine influenza virus with altered IFN antagonist activity, could be administered once to a subject. Alternatively, a vaccine or immunogenic formulation of the present invention, comprising $10^2$ to $10^8$ pfu can be used, preferably from about $10^3$ to $10^7$, more preferably $10^4$ pfu to about $5\times10^6$ pfu of mutant viruses with altered IFN antagonist activity, could be administered twice, three times, four times, five times, six times, seven times, eight times, nine times, or ten times to a subject with an interval of 2 to 6 months, 2 to 8 months, 2 to 10 months, or 2 to 12 months between doses. Alternatively, a vaccine or immunogenic formulation of the present invention, comprising $10^2$ to $10^8$ can be used, preferably from about $10^3$ to $10^7$, more preferably $10^4$ to about $5\times10^6$ pfu of mutant viruses with altered IFN antagonist activity, could be administered as often as needed to a subject. In a specific embodiment, the subject is a horse.

In certain embodiments, a vaccine formulation or an immunogenic formulation of the invention does not result in complete protection from an infection (e.g., a viral infection), but results in a lower titer or reduced number of the pathogen (e.g., a virus) compared to an untreated subject. Benefits include, but are not limited to, less severity of symptoms of the infection and a reduction in the length of the disease or condition associated with a the infection In certain embodiments, the vaccine formulation or immunogenic formulation of the invention is used to protect against infections by equine influenza virus. In other embodiments, a vaccine formulation of the invention is used to protect against infection by another equine virus, including, but not limited to, Equine Reovirus (Orbivirus), Arteritis virus, Equine Herpes Virus (EHV1), Equine Herpes Virus (EHV3), Equine Papova Virus, Retrovirus or Adenovirus. In yet other embodiments, the vaccine formulation or immunogenic formulation of the invention is used to protect against infections by pathogens other than an equine virus, including, but not limited to, *Clostridia* sp., *Salmonella* sp., *E. coli, Streptococcus equi, Taylorella equigenitalis* (CEM), *Klebsiella pneumoniae* and *Pseudomonas aeruginosa*, and *Dermatophilus congolensis.*

In certain embodiments, an immunogenic formulation of the invention is used for preventing, treating, managing or ameliorating conditions in which the induction of an immune response to a particular antigen is beneficial.

5.6 Pharmaceutical Formulations

The present invention encompasses pharmaceutical formulations comprising equine influenza viruses with altered IFN antagonist activity to be used as anti-viral agents or anti-tumor agents or as agents against IFN-treatable diseases. In one embodiment, the pharmaceutical formulations have utility as an anti-viral prophylactic and may be administered to a horse at risk of getting infected or is expected to be exposed to a virus, e.g., equine influenza virus. In another embodiment, the pharmaceutical formulations have utility as a therapeutic or prophylactic for an IFN-treatable disease and thus, can be used for treating, preventing, managing or ameliorating an IFN-treatable disorders. In a preferred embodiment, the pharmaceutical formulations have utility as a therapeutic or prophylactic for an equine IFN-treatable disease and thus, can be used for treating, preventing, managing or ameliorating an equine IFN-treatable disorders. In specific embodiments, the pharmaceutical formulations of the invention have utility as a therapeutic or prophylactic for an IFN-treatable disease and thus, can be used for treating, preventing, managing or ameliorating an IFN-treatable disorders in donkeys, zebras, camels, dogs, avians (e.g., ducks). In a preferred embodiment, the pharmaceutical formulations of the invention have utility as a therapeutic or prophylactic for an IFN-treatable disease and thus, can be used for treating, preventing, managing or ameliorating an IFN-treatable disorders in horses.

In certain embodiments, a pharmaceutical formulation of the invention comprises a chimeric attenuated equine influenza virus comprising a heterologous sequence. The heterologous sequence can encode an epitope from a foreign or tumor antigen. A foreign antigen can be selected from another virus, a bacteria or a parasite. In one embodiment, the pharmaceutical formulations may be used to treat tumors or prevent tumor formation, e.g., in horses who have cancer or in those who are at high risk for developing neoplasms or cancer. For example, a subject (e.g., a horse, donkey, or other animal that can be infected with equine influenza virus or in which equine influenza virus can replicate) with cancer can be treated to prevent further tumorigenesis. Alternatively, horses who are or are expected to be exposed to carcinogens can be treated. Alternatively, horses who are to be exposed to radiation can be treated prior to exposure and thereafter. Specific cancers that can be treated with the methods and compostions of the present invention include, but are not limited to, cancers of the uterus, mammary gland, pancreas, skin, lymph gland, vulva and testicle.

The antitumor properties of the invention can be at least partially related to their ability to induce IFN and IFN responses. Alternatively, the antitumor properties of the attenuated equine influenza viruses of the invention can be related to their ability to specifically grow in and kill tumor cells, many of which are known to have deficiencies in the IFN system. Regardless of the molecular mechanism(s) responsible for the antitumor properties, the attenuated equine influenza viruses of the invention may be used to treat tumors or to prevent tumor formation.

The present invention further encompasses the equine influenza viruses with an altered IFN antagonist phenotype which are targeted to specific organs, tissues and/or cells in the body in order to induce therapeutic or prophylactic effects locally. One advantage of such an approach is that the IFN-inducing equine influenza viruses of the invention are targeted to specific sites, e.g., the location of a tumor, to induce IFN in a site specific manner for a therapeutic effect rather than inducing IFN systemically which may have toxic effects.

The IFN-inducing equine influenza viruses of the invention may be engineered using the methods described herein to express proteins or peptides which would target the viruses to a particular site. In a specific embodiment, the IFN-inducing equine influenza viruses would be targeted to sites of tumors. In such an embodiment, the equine influenza viruses can be engineered to express the antigen combining site of an antibody which recognizes a tumor specific antigen, thus targeting the IFN-inducing equine influenza virus to the tumor. In another embodiment, where the tumor to be targeted expresses a hormone receptor, such as breast or ovarian tumors which express estrogen receptors, the IFN-inducing equine influenza virus may be engineered to express the appropriate hormone. In yet another embodiment, where the tumor to be targeted expresses a receptor to a growth factor, e.g., VEGF, EGF, or PDGF, the IFN-inducing virus may be engineered to express the appropriate growth factor or fragment thereof. Thus, in accordance with the invention, the IFN-inducing equine influenza viruses may be engineered to express any target gene product, including peptides, proteins, such as enzymes, hormones, growth factors, antigens or antibodies, which will function to target the equine influenza virus to a site in need of treatment (e.g., anti-viral, antibacterial, anti-microbial or anti-cancer therapy).

Methods of introduction include but are not limited to intradermal, intramuscular, intraperitoneal, intravenous, subcutaneous, intranasal, epidural, and oral routes. The pharmaceutical formulations of the present invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in a preferred embodiment it may be desirable to introduce the pharmaceutical formulations of the invention into the lungs by any suitable route. Pulmonary administration can also be employed, e.g., by use of an inhaler or nebulizer, and formulation with an aerosolizing agent.

In a specific embodiment, it may be desirable to administer the pharmaceutical formulations of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non porous, or gelatinous material, including membranes, such as sialastic membranes or fibers. In one embodiment, administration can be by direct injection at the site (or former site) of a malignant tumor or neoplastic or pre neoplastic tissue.

In another embodiment, the pharmaceutical formulation can be delivered in a biological matrix. An example of a biological matrix is described in U.S. Pat. No. 5,962,427, and U.S. Patent Application Publication U.S. 2002/0193338, herein incorporated by reference in their entireties.

In yet another embodiment, the pharmaceutical formulation can be delivered in a controlled release system. In one embodiment, a pump may be used (see Langer, supra; Sefton, 1987, CRC Crit. Ref. Biomed. Eng. 14:201; Buchwald et al, 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger & Peppas, 1983, J. Macromol. Sci. Rev. Macromol. Chem. 23:61; see also Levy et al., 1985, Science 228:190; During et al., 1989, Ann. Neurol. 25:351 (1989); Howard et al., 1989, J. Neurosurg. 71:105). In yet another embodiment, a controlled release system can be placed in proximity of the composition's target, i.e., the lung, thus requiring only a fraction of the systemic dose (see, e.g., Goodson, 1984, in Medical Applications of Controlled Release, supra, vol. 2, pp. 115-138). Other controlled release systems are discussed in the review by Langer (1990, Science 249: 1527-1533).

In a preferred embodiment, the pharmaceutical formulations of the present invention comprise an effective amount of an attenuated equine influenza virus of the invention, and a pharmaceutically acceptable carrier. The term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical formulation is administered. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained release formulations and the like. The composition can be formulated as a suppository. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain an effective amount of the therapy, preferably in purified form, together with a suitable amount of carrier so as to provide the form for proper administration to the patient. The formulation should suit the mode of administration. The particular formulation may also depend on whether equine influenza virus is live or inactivated.

The amount of the pharmaceutical formulation of the invention which will be effective in the treatment, prevention, management, or amelioration of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for administration are generally about $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu, and most preferably about $10^4$ to about $10^{12}$, and can be administered to a subject once, twice, three or more times with intervals as often as needed. Pharmaceutical formulations of the present invention comprising $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu, and most preferably about $10^4$ to about $10^{12}$, of an attenuated equine influenza virus with altered IFN antagonist activity, can be administered to a subject intranasally, intratracheally, intramuscularly or subcutaneously Effective doses may be extrapolated from dose response curves derived from in vitro or animal model test systems.

In certain embodiments, the pharmaceutical formulation of the invention is used to prevent, manage, treat or ameliorate infections by viruses, bacteria or parasites. In other embodiments, the pharmaceutical formulation of the invention is used to prevent, manage, treat or ameliorate cancer in a horse. In other embodiments, the pharmaceutical formulation of the invention is used to prevent, manage, treat or ameliorate other IFN-treatable diseases.

5.7 Therapies Useful in Combination with Equine Influenza Virus

The present invention also provides methods for preventing, managing, treating, and/or ameliorating diseases and disorders including, but not limited to, equine influenza virus infections, conditions associated with equine influenza virus infection, infections other than equine influenza virus infections, conditions associated with infections other than equine influenza virus infections, IFN-treatable disorders (e.g., cancer) and conditions in which an attenuated equine influenza virus of the invention is used as a vector to induce an immune response to an antigen associated with the condition comprising administering to a subject in need thereof an effective amount of one or more attenuated equine influenza viruses of the present invention and an effective amount of one or more therapies (e.g., prophylactic or therapeutic agents) other than attenuated equine influenza viruses. Therapies include, but are not limited to, small molecules, synthetic drugs, peptides, polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides) antibodies, synthetic or natural inorganic molecules, mimetic agents, and synthetic or natural organic molecules.

Any therapy (e.g., prophylactic or therapeutic agents) which is known to be useful, or which has been used or is currently being used for the prevention, management, treatment, or amelioration of an equine influenza virus infection, infections other than equine influenza virus infections, conditions associated with infections other than equine influenza virus infections, IFN-treatable disorders, conditions in which an attenuated equine influenza virus of the invention is used as a vector to induce an immune response to an antigen associated with the condition, or any other horse disease can be used in combination with an attenuated equine influenza virus in accordance with the invention described herein. See, e.g., Belschner, *Horse Diseases: Causes, Symptoms and Treatments*, Wilshire Book Co., 1975; and Siegel, ed., *UC Davis Book of Horses: A Complete Medical Reference Guide For Horses and Foals,* 1st ed., Harper Collins Publishers, 1996, for information regarding therapies, in particular prophylactic or therapeutic agents, which have been or are currently being used for preventing, treating, managing, and/or ameliorating horse diseases. Examples of prophylactic and therapeutic agents include, but are not limited to, anti-cancer agents; anti-viral agents, anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone)) and antibiotics (e.g., dactinomycin (formerly actinomycin), bleomycin, erythomycin, penicillin, mithramycin, and anthramycin (AMC)).

5.7.1 Anti-Cancer Therapies

Any therapy (e.g., therapeutic or prophylactic agent) which is known to be useful, has been used, or is currently being used for the prevention, treatment, management, or amelioration of cancer or one or more symptoms thereof can be used in compositions and method of the invention. Therapies (e.g., therapeutic or prophylactic agents) include, but are not limited to, peptides, polypeptides, fusion proteins, nucleic acid molecules, small molecules, mimetic agents, synthetic drugs, inorganic molecules, and organic molecules. Non-limiting examples of cancer therapies include chemotherapies, radiation therapies, hormonal therapies, and/or biological therapies/immunotherapies.

In particular embodiments, the anti-cancer agent may be, but is not limited to: a chemotherapeutic agent (e.g., acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, azacitidine, azetepa, batimastat, bleomycin, benzodepa, bicalutamide, bisantrene hydrochloride, bisnafide dimesylate, bizelesin, bleomycin sulfate, brequinar sodium, bropirimine, busulfan, cactinomycin, calusterone, campathecin, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, cyclosporin A, combretastatin A4, combretastatin analogue, cytolytic factor, cytostatin, dacliximab, docetaxel, dacarbazine, dactinomycin, daunorubicin hydrochloride, docetaxel, doxorubicin, droloxifene, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, etanidazole, etoposide, fazarabine, fenretinide, floxuridine, fluorouracil, flurocitabine, fosquidone, gemcitabine, hydroxyurea, idarubicin, idarubicin hydrochloride, ifosfamide, ilmofosine, iproplatin, ifosfamide, irinotecan hydrochloride, lanreotide acetate, letrozole, leuprolide acetate, liarozole hydrochloride, lometrexol sodium, lomustine, losoxantrone hydrochloride, masoprocol, mercaptopurine, methotrexate, metoprine, meturedepa, mitindomide, mitocarcin, mitocromin, mitomycin, mitoxantrone, mycophenolic acid, nitrosoureas, nocodazole, nogalamycin, ormaplatin, oxisuran, paclitaxel, plicamycin, platinum complex, platinum compounds, platinum-triamine complex, procarbizine, puromycin, taxol, thioguanine, talisomycin, tecogalan sodium, tegafur, teloxantrone hydrochloride, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, and zinostatin), matrix metalloproteinase inhibitors, tyrosine kinase inhibitors, tyrphostins, urokinase receptor antagonists, multiple drug resistance gene inhibitor, multiple tumor suppressor 1-based therapy, plasminogen activator inhibitor, bisphosphonates (e.g., pamidronate (Aredria), sodium clondronate (Bonefos), zoledronic acid (Zometa), alendronate (Fosamax), etidronate, ibandronate, cimadronate, risedromate, and tiludromate), a cytokine (e.g., IL-2, IFN-α, IFN-β, IFN-γ, leukemia inhibiting factor, leukocyte alpha interferon, human chorionic gonadotrophin, and thrombopoietin), a hormone (e.g., thyroid stimulating hormone), an antibody (e.g., an anti-CD2 antibody, an anti-CD20 antibody, and an antibody immunospecific for one or more galanin receptors), vitamin D (e.g., 20-epi-1,25 dihydroxyvitamin D3), an angiogenesis inhibitor, an antisense oligonucleotide, an apoptosis gene modulator, an apoptosis regulator, a BCR/ABL antagonist, a cartilage derived inhibitor, an estrogen agonist, an estrogen antagonist, a gelatinase inhibitor, a glutathione inhibitor, an HMG CoA reductase inhibitor (e.g., atorvastatin, cerivastatin, fluvastatin, lescol, lupitor, lovastatin, rosuvastatin, and simvastatin), an immunostimulant peptide, an insulin-like growth factor-1 receptor inhibitor, an interferon agonist, leuprolide+estrogen+progesterone, leuprorelin, a mismatched double stranded RNA, a proteasome inhibitor, a protein A-based immune modulator, a protein kinase C inhibitor, a protein tyrosine phosphatase inhibitor, a raf antagonist, a ras farnesyl protein transferase inhibitor, a ribozyme, RNAi, a signal transduction modulator, a stem cell inhibitor, a stem-cell division inhibitor, a telomerase inhibitor, a thymopoietin receptor agonist, and a translation inhibitor.

In specific embodiments, radiation therapy comprising the use of x-rays, gamma rays and other sources of radiation to destroy the cancer cells is used in combination with the attenuated equine influenza viruses of the invention. In preferred embodiments, the radiation treatment is administered as external beam radiation or teletherapy, wherein the radiation is directed from a remote source. In other preferred embodiments, the radiation treatment is administered as internal therapy or brachytherapy wherein a radioactive source is placed inside the body close to cancer cells or a tumor mass.

Cancer therapies and their dosages, routes of administration and recommended usage are known in the art and have been described in such literature as the *Physicians' Desk Reference* (58th ed., 2004) and Merck Veterinary Manual (8th ed., 1998).

5.7.2 Anti-Angiogenesis Therapies

Any anti-angiogenic agent well-known to one of skill in the art can be used in the compositions and methods of the invention. Non-limiting examples of anti-angiogenic agents include proteins, polypeptides, peptides, fusion proteins, antibodies (e.g., chimeric, monoclonal, polyclonal, Fvs, ScFvs, Fab fragments, $F(ab)_2$ fragments, and antigen-binding fragments thereof) such as antibodies that immunospecifically bind to TNFα, nucleic acid molecules (e.g., antisense molecules or triple helices), organic molecules, inorganic molecules, and small molecules that reduce or inhibit or neutralizes the angiogenesis. In particular, examples of anti-angiogenic agents, include, but are not limited to, endostatin, angiostatin, apomigren, anti-angiogenic antithrombin III, the 29 kDa N-terminal and a 40 kDa C-terminal proteolytic fragments of fibronectin, a uPA receptor antagonist, the 16 kDa proteolytic fragment of prolactin, the 7.8 kDa proteolytic fragment of platelet factor-4, the anti-angiogenic 24 amino acid fragment of platelet factor-4, the anti-angiogenic factor designated 13.40, the anti-angiogenic 22 amino acid peptide fragment of thrombospondin I, the anti-angiogenic 20 amino acid peptide fragment of SPARC, RGD and NGR containing peptides, the small anti-angiogenic peptides of laminin, fibronectin, procollagen and EGF, integrin $\alpha V\beta_3$ antagonists (e.g., anti-integrin αVβ3 antibodies), acid fibroblast growth factor (aFGF) antagonists, basic fibroblast growth factor (bFGF) antagonists, vascular endothelial growth factor (VEGF) antagonists (e.g., anti-VEGF antibodies), and VEGF receptor (VEGFR) antagonists (e.g., anti-VEGFR antibodies).

5.7.3 Anti-Viral Therapies

Any anti-viral agent well-known to one of skill in the art can be used in the compositions and the methods of the invention. Non-limiting examples of anti-viral agents include proteins, polypeptides, peptides, fusion proteins antibodies, nucleic acid molecules, organic molecules, inorganic molecules, and small molecules that inhibit and/or reduce the attachment of a virus to its receptor, the internalization of a virus into a cell, the replication of a virus, or release of virus from a cell. In particular, anti-viral agents include, but are not limited to, nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, alpha-interferons and other interferons, and AZT.

In specific embodiments, the anti-viral agent is an immunomodulatory agent that is immunospecific for a viral antigen. As used herein, the term "viral antigen" includes, but is not limited to, any viral peptide, polypeptide and protein of an equine virus (e.g., epitopes of Equine Reovirus (Orbivirus), Arteritis Virus, Equine Herpes Virus (EHV1, EHV2, EHV3, EHV4 and EHV5), Equine Papova Virus, Retrovirus, Adenovirus, African Horse Sickness Virus, Shipping Fever Virus, West Nile Virus, Equine Encephalitis Virus, Vesicular Stomatitis Virus (VSV), Equine Rhinovirus, and Hendra Virus) that is capable of eliciting an immune response. Antibodies useful in this invention for treatment of a viral infectious disease include, but are not limited to, antibodies against antigens of pathogenic viruses, including as examples and not by limitation: adenovirdiae (e.g., mastadenovirus and aviadenovirus), herpes viridae (e.g., herpes simplex virus 1, herpes simplex virus 2, herpes simplex virus 5, and herpes simplex virus 6), leviviridae (e.g., levivirus, enterobacteria phase MS2, allolevirus), poxviridae (e.g., chordopoxvirinae, parapoxvirus, avipoxvirus, capripoxvirus, leporiipoxvirus, suipoxvirus, molluscipoxvirus, and entomopoxvirinae), papovaviridae (e.g., polyomavirus and papillomavirus), paramyxoviridae (e.g., paramyxovirus, parainfluenza virus 1, mobillivirus (e.g., measles virus), rubulavirus (e.g., mumps virus), pneumonovirinae (e.g., pneumovirus, human respiratory synctial virus), and metapneumovirus (e.g., avian pneumovirus and human metapneumovirus)), picornaviridae (e.g., enterovirus, rhinovirus, hepatovirus (e.g., human hepatits A virus), cardiovirus, and apthovirus), reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses, lentivirus (e.g., human immunodeficiency virus 1 and human immunodeficiency virus 2), spumavirus), flaviviridae (e.g., hepatitis C virus), hepadnaviridae (e.g., hepatitis B virus), togaviridae (e.g., alphavirus (e.g., sindbis virus) and rubivirus (e.g., rubella virus)), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus).

Specific examples of antibodies available useful for the treatment of a viral infectious disease include, but are not limited to, PRO542 (Progenics) which is a CD4 fusion antibody useful for the treatment of HIV infection; Ostavir (Protein Design Labs, Inc., CA) which is a human antibody useful for the treatment of hepatitis B virus; and Protovir (Protein Design Labs, Inc., CA) which is a humanized IgG1 antibody useful for the treatment of cytomegalovirus (CMV).

Anti-viral therapies and their dosages, routes of administration and recommended usage are known in the art and have been described in such literature as the *Physicians' Desk Reference* (58th ed., 2004) and Merck Veterinary Manual (8th ed., 1998). Additional information on viral infections is available in Cecil Textbook of Medicine (18th ed., 1988).

5.7.4 Antibiotic Therapies

Any antibiotic agent well-known to one of skill in the art can be used in the compositions and the methods of the invention. Antibacterial agents or antibiotics that can be used in combination with the complexes of the invention include but are not limited to: aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), macrolides (e.g., azithromycin, carbomycin, clarithomycin, dirithromycin, erythromycin, and erythromycin acistrate), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, ciprofloxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

Additional examples of antibacterial agents include but are not limited to Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambemiycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefanmandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmnenoxime Hydrochloride, Cefinetazole, Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monesin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifuirthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafingin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin.

Antibiotic therapies and their dosages, routes of administration and recommended usage are known in the art and have been described in such literature as the *Physicians' Desk Reference* (58th ed., 2004) and Merck Veterinary Manual (8th ed., 1998).

5.7.5 Immunomodulatory Therapies

Any immunomodulatory agent well-known to one of skill in the art may be used in the methods and compositions of the invention. Immunomodulatory agents can affect one or more or all aspects of the immune response in a subject. Aspects of the immune response include, but are not limited to, the inflammatory response, the complement cascade, leukocyte and lymphocyte differentiation, proliferation, and/or effector function, monocyte and/or basophil counts, and the cellular communication among cells of the immune system. In certain embodiments of the invention, an immunomodulatory agent modulates one aspect of the immune response. In other embodiments, an immunomodulatory agent modulates more than one aspect of the immune response. In a preferred embodiment of the invention, the administration of an immunomodulatory agent to a subject inhibits or reduces one or more aspects of the subject's immune response capabilities. In certain embodiments, an immunomodulatory agent is not an anti-inflammatory agent. In certain embodiments, an immunomodulatory agent is not an anti-angiogneic agent. In certain embodiments, an immunomodulatory agent is a chemotherapeutic agent. In certain embodiments, an immunomodulatory agent is not a chemotherapeutic agent.

Examples of immunomodulatory agents include, but are not limited to, proteinaceous agents such as cytokines, peptide mimetics, and antibodies (e.g., human, humanized, chimeric, monoclonal, polyclonal, Fvs, ScFvs, Fab or F(ab)$_2$ fragments or epitope binding fragments), nucleic acid molecules (e.g., antisense nucleic acid molecules and triple helices), small molecules, organic compounds, and inorganic compounds. In particular, immunomodulatory agents include, but are not limited to, methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, and cytokine receptor modulators.

Examples of T cell receptor modulators include, but are not limited to, anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD2 antibodies, anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD11a antibodies (e.g., Xanelim (Genentech)), and anti-B7 antibodies (e.g., IDEC-114) (IDEC))), CTLA4-immunoglobulin, and LFA-3TIP (Biogen, International Publication No. WO 93/08656 and U.S. Pat. No. 6,162,432).

Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin IL-2, IL-3, IL-4, IL-5, IL-6, IL-7, IL-8, IL-9, IL-10, IL-11, IL-12, IL-13, IL-15, IL-23, TNF-α, TNF-β, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-3 receptor antibodies, anti-IL-4 receptor antibodies, anti-IL-6 receptor antibodies, anti-IL-9 receptor antibodies anti-IL-10 receptor antibodies, anti-IL-12 receptor antibodies, anti-IL-13 receptor antibodies, anti-IL-15 receptor antibodies, and anti-IL-23 receptor antibodies), anti-cytokine antibodies (e.g., anti-IFN antibodies, anti-TNF-α antibodies, anti-IL-1β antibodies, anti-IL-3 antibodies, anti-IL-6 antibodies, anti-IL-8 antibodies (e.g., ABX-IL-8 (Abgenix)), anti-IL-9 antibodies anti-IL-12 antibodies, anti-IL-13 antibodies, anti-IL-15 antibodies, and anti-IL-23 antibodies).

In a specific embodiment, a cytokine receptor modulator is IL-3, IL-4, IL-10, or a fragment thereof. In another embodiment, a cytokine receptor modulator is an anti-IL-1β antibody, anti-IL-6 antibody, anti-IL-12 receptor antibody, or anti-TNF-α antibody. In another embodiment, a cytokine receptor modulator is the extracellular domain of a TNF-α receptor or a fragment thereof.

In certain embodiments, an immunomodulatory agent is a B cell receptor modulator. Examples of B cell receptor modulators include, but are not limited to, CD19. Targeting B cell receptors provides one means for modulating B cells.

In a preferred embodiment, proteins, polypeptides or peptides (including antibodies) that are utilized as immunomodulatory agents are derived from the same species as the recipient of the proteins, polypeptides or peptides so as to reduce the likelihood of an immune response to those proteins, polypeptides or peptides. In another preferred embodiment, when the subject is a horse, the proteins, polypeptides, or peptides that are utilized as immunomodulatory agents are derived from horse.

In accordance with the invention, one or more immunomodulatory agents are administered to a subject prior to, subsequent to, or concomitantly with an attenuated equine influenza virus. Any technique well-known to one skilled in the art can be used to measure one or more aspects of the immune response in a particular subject, and thereby determine when it is necessary to administer an immunomodulatory agent to said subject. In a preferred embodiment, a mean absolute lymphocyte count of approximately 500 cells/mm$^3$, preferably 600 cells/mm$^3$, 650 cells/mm$^3$, 700 cells/mm$^3$, 750 cells/mm$^3$, 800 cells/mm$^3$, 900 cells/mm$^3$, 1000 cells/mm$^3$, 1100 cells/mm$^3$, or 1200 cells/mm$^3$ is maintained in a subject.

Preferably, agents that are commercially available and known to function as immunomodulatory agents are used in accordance with the methods of the invention. The immunomodulatory activity of an agent can be determined in vitro and/or in vivo by any technique well-known to one skilled in the art, including, e.g., by CTL assays, proliferation assays, and immunoassays (e.g., ELISAs) for the expression of particular proteins such as co-stimulatory molecules and cytokines.

5.8 Dosage & Frequency of Administration

The amount of a prophylactic or therapeutic agent or a composition of the invention which will be effective in the prevention, treatment, management, and/or amelioration of an equine influenza virus infection or a condition associated therewith, an infection other than an equine influenza virus infection or a condition associated therewith, an IFN-treatable disease or a condition in which an attenuated equine influenza virus of the invention is used as a vector to induce an immune response to an antigen associated with the condition, or the prevention of the recurrence, onset, or development of one or more symptoms of an equine influenza virus infection or a condition associated therewith, an infection other than an equine influenza virus infection or a condition associated therewith, an IFN-treatable disease, or a condition in which an attenuated equine influenza virus of the invention is used as a vector to induce an immune response to an antigen associated with the condition, can be determined by standard clinical methods. The frequency and dosage will vary also according to factors specific for each patient depending on the specific therapies (e.g., the specific therapeutic or prophylactic agent or agents) administered, the severity of the disorder, disease, or condition, the route of administration, as well as age, body, weight, response, and the past medical history of the patient. For example, the dosage of a prophylactic or therapeutic agent or a composition of the invention which will be effective in the treatment, prevention, management, and/or amelioration of an equine influenza virus infection or a condition associated therewith, a viral infection other than an equine influenza virus infection or a condition associated therewith, or an IFN-treatable disease, or the prevention of the recurrence, onset, or development of one or more symptoms of an equine influenza virus infection or a condition associated therewith, a viral infection other than an equine influenza virus infection or a condition associated therewith, or an IFN-treatable disease, can be determined by animal models such as those known to those skilled in the art. In addition, in vitro assays may optionally be employed to help identify optimal dosage ranges. Suitable regimens can be selected by one skilled in the art by considering such factors and by following, for example, dosages are reported in literature and recommended in the *Physicians' Desk Reference* (58th ed., 2004) or Merck Veterinary Manual (8th ed., 2003).

Exemplary doses of a vaccine or immunogenic formulation include $10^2$ to about $10^8$, about $10^3$ to about $10^7$, about $10^4$ to about $5 \times 10^6$ pfu or $10^4$ to about $10^7$ pfu. In other embodiments, the dose of a vaccine or immunogenic formulation of the invention administered to a subject is $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$ or $10^8$ pfu. Exemplary doses of a pharmaceutical formulation include $10^2$, $5 \times 10^2$, $10^3$, $5 \times 10^3$, $10^4$, $5 \times 10^4$, $10^5$, $5 \times 10^5$, $10^6$, $5 \times 10^6$, $10^7$, $5 \times 10^7$, $10^8$, $5 \times 10^8$, $1 \times 10^9$, $5 \times 10^9$, $1 \times 10^{10}$, $5 \times 10^{10}$, $1 \times 10^{11}$, $5 \times 10^{11}$ or $10^{12}$ pfu. In certain embodiments, the dose of the pharmaceutical formulation administered to the subject is between about $10^2$ to about $10^{12}$, about $10^2$ to about $10^{10}$, about $10^2$ to about $10^8$, about $10^3$ to about $10^9$, about $10^3$ to about $10^7$, about $10^4$ to about $10^8$, about $10^4$ to about $5 \times 10^6$ pfu or about $10^4$ to about $10^{12}$ pfu.

Exemplary doses of a small molecule include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

For antibodies, proteins, polypeptides, peptides and fusion proteins encompassed by the invention, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Generally, horse antibodies have a longer half-life within the horse than antibodies from other species due to the immune response to the foreign polypeptides. Thus, lower dosages of horse antibodies and less frequent administration to horses is often possible. Further, the dosage and frequency of administration of antibodies or fragments thereof may be reduced by enhancing uptake and tissue penetration of the antibodies by modifications such as, for example, lipidation.

Preferably, the dosages of prophylactic or therapeutic agents used in combination therapies of the invention are lower than those which have been or are currently being used to prevent, treat, manage, and/or ameliorate an equine influenza virus infection or a condition or symptoms associated therewith, an infection other than an equine influenza virus infection or a condition or symptom associated therewith, an IFN treatable disease, or a condition in which an attenuated equine influenza virus of the invention is used as a vector to induce an immune response to an antigen associated with the condition. The recommended dosages of agents currently used for the prevention, treatment, management, or amelioration of an equine influenza virus infection or a condition or symptoms associated therewith, an infection other than an equine influenza virus infection or a condition or symptom associated therewith, an IFN treatable disease, or a condition in which an attenuated equine influenza virus of the invention is used as a vector to induce an immune response to an antigen associated with the condition, can be obtained from any reference in the art including, but not limited to, Hardman et al., eds., 2001, Goodman & Gilman's The Pharmacological Basis Of Basis Of Therapeutics, 10th ed., Mc-Graw-Hill, New York; *Physicians' Desk Reference* (PDR) 58th ed., 2004, Medical Economics Co., Inc., Montvale, N.J.; Merck Veterinary Manual (8th ed., 2003); and Robbinson, Current Therapy in Equine Medicine, 5th ed., 2003, Saunders, Philadelphia, each of which is incorporated by reference herein in its entirety.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies are administered within the same patent visit.

In certain embodiments, one or more compositions of the invention and one or more other therapies (e.g., prophylactic or therapeutic agents) are cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In a certain other embodiments, a vaccine or immunogenic composition of the invention is administered to a subject at a single dose followed by a second dose 3 to 6 weeks later. In accordance with these embodiments, booster vaccinations are administered to the subject at 6 to 12 month intervals following the second vaccination. In a preferred embodiment, the subject is a mammal. In a more preferred embodiment, the subject is a horse with an equine influenza A infection.

In certain embodiments, the administration of the same compositions of the invention may be repeated and the administrations may be separated by at least 1 day, 2 days, 3 days, 5 days, 10 days, 15 days, 30 days, 45 days, 2 months, 75 days, 3 months, or at least 6 months. In other embodiments, the administration of the same therapy (e.g., prophylactic or therapeutic agent) other than a composition of the invention may be repeated and the administration may be separated by at least at least 1 day, 2 days, 3 days, 5 days, 10 days, 15 days, 30 days, 45 days, 2 months, 75 days, 3 months, or at least 6 months.

5.9 Biological Assays 5.9.1 In Vitro Assays

Growth of the attenuated equine influenza viruses of the present invention can be assessed in horse cells, e.g., equine fetal kidney cells, (e.g., FEK cells), other horse cells as described herein, and other IFN-competent and IFN-deficient cells. In a specific embodiment, FEK cells are infected at a MOI of 0.0005 and 0.001, 0.001 and 0.01, 0.01 and 0.1, 0.1 and 1, or 1 and 10, or a MOI of 0.0005, 0.001, 0.005, 0.01, 0.05, 0.1, 0.5, 1, 5 or 10 and incubated with serum free media supplemented with 5% allantoic fluid (F. Cook, University of Kentucky, Lexington, Ky.). Viral titers are determined in the supernatant by HA plaqued in MDCK cells as described below. Other cells in which viral titers can be assessed include, but are not limited to, EFK-2 cells, Vero cells, primary human umbilical vein endothelial cells (HUVEC), H292 human epithelial cell line and HeLa cells.

Viral assays include those that measure altered viral replication (as determined, e.g., by plaque formation) or the production of viral proteins (as determined, e.g., by western blot analysis) or viral RNAs (as determined, e.g., by RT-PCR or northern blot analysis) in cultured cells in vitro using methods which are well known in the art.

Induction of IFN responses may be determined by measuring the phosphorylated state of components of the IFN pathway following infection with the test mutant virus, e.g., IRF 3, which is phosphorylated in response to double stranded RNA. In response to type I IFN, Jak1 kinase and TyK2 kinase, subunits of the IFN receptor, STAT1, and STAT2 are rapidly tyrosine phosphorylated. Thus, in order to determine whether the attenuated equine influenza virus induces IFN responses, cells, such as 293 cells, are infected with the test mutant virus and following infection, the cells are lysed. IFN pathway components, such as Jak1 kinase or TyK2 kinase, are immunoprecipitated from the infected cell lysates, using specific polyclonal sera or antibodies, and the tyrosine phosphorylated state of the kinase is determined by immunoblot assays with an anti-phosphotyrosine antibody (e.g., see Krishnan et al. 1997, Eur. J. Biochem. 247: 298 305). An enhanced phosphorylated state of any of the components of the IFN pathway following infection with the attenuated equine influenza virus would indicate induction of IFN responses by the attenuated equine influenza virus.

Induction of IFN responses may be determined by measuring IFN dependent transcriptional activation following infection with the test attenuated equine influenza virus. In this embodiment, the expression of genes known to be induced by IFN, e.g., Mx, PKR, 2 5 oligoadenylatesynthetase, major histocompatibility complex (MLC) class I, etc., can be analyzed by techniques known to those of skill in the art (e.g., northern blots, western blots, PCR, etc.). Alternatively, test cells such as embryonic kidney cells or osteogenic sarcoma cells, are engineered to transiently or constitutively express reporter genes such as luciferase reporter gene or chloramphenicol transferase (CAT) reporter gene under the control of an interferon stimulated response element, such as the IFN stimulated promoter of the ISG 54K gene (Bluyssen et al., 1994, Eur. J. Biochem. 220:395 402). Cells are infected with the test attenuated equine influenza virus and the level of expression of the reporter gene compared to that in uninfected cells or cells infected with wild type virus. An increase in the level of expression of the reporter gene following infection with the test virus would indicate that the test attenuated equine influenza virus is inducing an IFN response.

Measuring IFN induction can also be assessed by determining whether an extract from the cell or egg infected with the test attenuated equine influenza virus is capable of conferring protective activity against viral infection. More specifically, groups of 10-12 day old embryonated chicken eggs or 10 day old embryonated chicken eggs are infected with the test attenuated equine influenza virus or the wild type virus. Approximately 15 to 20 hours post infection, the allantoic fluid is harvested and tested for IFN activity by determining the highest dilution with protective activity against equine influenza virus infection in tissue culture cells, such as MDCK cells.

5.9.2 In Vivo Assays

The decreased virulence of the attenuated equine influenza viruses of the present invention can be assessed in a subject, in particular, horses. In one example, the ability to induce lung lesions and cause infection in equine is compared to wild-type equine influenza virus and mock virus. Lung lesions can be assessed as a percentage of lung lobes that are healthy by visual inspection. Animals are euthanized 5 days p.i. by intravenous administration of pentobarbital, and their lungs are removed in toto. The percentage of the surface of each pulmonary lobe that is affected by macroscopic lesions is estimated visually. The percentages are averaged to obtain a mean value for the 7 pulmonary lobes of each animal.

In other assays, nasal swabs and BALF can be tested to determine virus burden or titer. Nasal swabs can be taken during necropsy to determine viral burden post-infection. Samples can also be taken with care from standing horses to determine viral burden post-infection. BALF can be obtained after the lungs are removed from the thoracic cavity by rinsing the lungs (via trachea) with about 30 ml of McCoy's medium without serum.

For quantitation of virus in tissue samples, tissue samples are homogenized in phosphate-buffered saline (PBS), and dilutions of clarified homogenates adsorbed for 1 h at 37° C. onto monolayers of MDCK cells. Infected monolayers are then overlaid with a solution of minimal essential medium containing 0.1% bovine serum albumin (BSA), 0.01% DEAE-dextran, 0.1% $NaHCO_3$, and 1% agar. Plates are incubated 2 to 3 days until plaques could be visualized. Tissue culture infectious dose (TCID) assays to titrate virus from PR8-infected samples are carried out as follows. Confluent monolayers of MDCK cells in 96-well plates are incubated with log dilutions of clarified tissue homogenates in media. Two to three days after inoculation, 0.05-ml aliquots from each well are assessed for viral growth by hemagglutination assay (HA assay).

In yet other assays, histopathologic evaluations are performed after infection. The nasal turbinates and trachea are examined for epithelial changes and subepithelial inflammation. The lungs are examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliate apical borders and basal pseudostratified nuclei; minimal inflammation); 1+ (epithelial layer columnar and even in outline with only slightly increased proliferation; cilia still visible on many cells); 2+ (prominent changes in the epithelial layer ranging from attenuation to marked proliferation; cells disorganized and layer outline irregular at the luminal border); 3+ (epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+ (focal squamous metaplasia of the epithelial layer); 2+ (diffuse squamous metaplasia of much of the epithelial layer, cilia may be evident focally); 2.5+ (diffuse squamous metaplasia with very few cilia evident).

Equine influenza virus immunohistochemistry is performed using a NP-specific monoclonal antibody. Staining is graded 0 to 3+ as follows: 0 (no infected cells); 0.5+ (few infected cells); 1+ (few infected cells, as widely separated individual cells); 1.5+ (few infected cells, as widely separated singles and in small clusters); 2+ (moderate numbers of infected cells, usually affecting clusters of adjacent cells in portions of the epithelial layer lining bronchioles, or in small sublobular foci in alveoli); 3+ (numerous infected cells, affecting most of the epithelial layer in bronchioles, or widespread in large sublobular foci in alveoli).

5.9.3 Determining Viral Titer

Viral titer is determined by inoculating serial dilutions of equine influenza virus into cell cultures (e.g., horse cultures), chick embryos, or live animals (e.g., horses). After incubation of the virus for a specified time, the virus is isolated using standard methods.

The HA assay is carried out in V-bottom 96-well plates. Serial twofold dilutions of each sample in PBS were incubated for 1 h on ice with an equal volume of a 0.5% suspension of chicken erythrocytes in PBS. Positive wells contained an adherent, homogeneous layer of erythrocytes; negative wells contain a nonadherent pellet.

Physical quantitation of the virus titer can be performed using PCR applied to viral supernatants (Quinn & Trevor, 1997; Morgan et al., 1990), hemagglutination assays, tissue culture infectious doses (TCID50) or egg infectious doses (EID50).

5.9.4 Toxicity Studies

The toxicity and/or efficacy of the compositions of the present invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred. While therapies that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the therapies for use in subjects (e.g., horses). The dosage of such agents lies preferably within a range of circulating concentrations that include the ED50 with little or no toxicity. The dosage may vary within this range depending upon the dosage form employed and the route of administration utilized. For any therapy used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in subjects (e.g., horses). Levels in plasma may be measured, for example, by high performance liquid chromatography.

Further, any assays known to those skilled in the art can be used to evaluate the prophylactic and/or therapeutic utility of a composition, a combination therapy disclosed herein for equine influenza virus infection or a condition or symptoms associated therewith, an infection other than an equine influenza virus infection or a condition or symptom associated therewith, an IFN treatable disease, or a condition in which an attenuated equine influenza virus of the invention is used as a vector to induce an immune response to an antigen associated with the condition.

The following examples are provided to further illustrate the current invention but are not provided to in any way limit the scope of the current invention.

6. EXAMPLE

Attenuation of Equine Influenza Viruses Through Mutations in the NS1 Protein This example demonstrates the attenuation of equine influenza viruses by the introduction of mutations in the NS1 gene of the viruses.

6.1 Materials and Methods

6.1.1 Cells and Viruses

Equine fetal kidney (FEK) cells (S. Cook, University of Kentucky) and Madin-Darby canine kidney (MDCK) cells (ATCC, Manassas, Va.) were grown in Minimum Essential Medium (MEM) supplemented with 10% fetal calf serum (FCS) and 1% penicillin/streptomycin. Human embryonic kidney 293T cells (ATCC) were grown in Dulbecco's Modified Eagle Medium (DMEM) also supplemented with 10% FCS and 1% penicillin/streptomycin. The equine influenza virus, A/eq/KY/5/02, was isolated from a nasopharyngeal swab from a diseased horse in Lexington, Ky. in 2002. A stock of virus was propagated following a total of 3 passages in embryonated hen eggs and had an HA titer of 128. Recombinant vesicular stomatitis virus tagged with green fluorescent protein (VSV-GFP) (Stojdl et al., 2003, Cancer Cell 4:263-275) was kindly provided by John Hiscott (McGill University, Montreal).

6.1.2 Gene End Sequence Determination

Viral RNA was extracted from 300 µl of allantoic fluid using the Qiagen RNeasy Mini kit (Qiagen, Valencia, Calif.) according to the protocol provided. To determine 3' vRNA end sequences, an adenosine tail was added to vRNA using a Poly(A) Polymerase enzyme (Ambion, Austin, Tex.) and then reverse transcribed using the primer 5'-TTTTTTTTTTTTTTTTTTTTTTTTTAGC-3' (SEQ ID NO:1). Reverse transcription reactions were carried out with Superscript II RT enzyme (Invitrogen, Carlsbad, Calif.). PCR reactions were carried out using the same primer and a conserved gene-specific primer for each viral segment: PB2: 5'-CATTCCTATTCCACC-3' (SEQ ID NO:2); PB 1: 5'-AAAGCCATTGCTTCC-3' (SEQ ID NO:3); PA: 5'-CTACTGTCCATGCC-3' (SEQ ID NO:4); HA: 5'-CATATGGGTAGCAATTG-3' (SEQ ID NO:5); NP: 5'-GATTCCTCCCACCATC-3' (SEQ ID NO:6); NA: 5'-GGACCAGTACTGTTAC-3' (SEQ ID NO:7); M: 5'-TACGCTGCAGTCC-3' (SEQ ID NO:8); NS: 5'-CTTCTGGTCTCGGCG-3' (SEQ ID NO:9). For sequence determination of the 5' vRNA ends, PCR reactions were carried out using a primer recognizing the 5' viral RNA non-coding (NC) region common to all eight influenza virus segments 5'-CATCGCTCTTCTATTAGTAGAAACAAGG-3' (SEQ ID NO:10) and a conserved gene-specific primer for each viral segment: PB2: 5'-AGCATACTTACTGACAG-3' (SEQ ID NO:11); PB1: 5'-AGGCCATGGTGTC-3' (SEQ ID NO:12); PA: 5'-CAACCTGGAACCTGG-3' (SEQ ID NO:13); HA: 5'-CAGGCTACAAAGATTGG-3' (SEQ ID NO:14); NP: 5'-GGCAATAAGGAC-3' (SEQ ID NO:15); NA: 5'-TCACATTGCCGGTTG-3' (SEQ ID NO:16); M: 5'-CGGATGGGAGTGC-3' (SEQ ID NO:17); NS: 5'-GTGCGACATAGATTG-3' (SEQ ID NO:18). PCR products were sequenced (Mount Sinai DNA sequencing facility, NY) and based on the sequences obtained, cloning primers for each segment were designed that included a SapI recognition sequence and the first 15-25 nucleotides of the vRNA ends.

6.1.3 Construction of Plasmids

Full-length cDNAs were generated for each viral segment by reverse transcribing vRNA using a Forward SapI primer: 5'-CATCGCTCTTCTATTAGTAGAAACAAGG-3' (SEQ ID NO:10) for the non-coding region of each segment followed by PCR with the designed cloning primers. The ambisense cloning vector pDZ was derived from the protein expression plasmid pCAGGS provided by J. Miyazaki (Osaka University, Japan; Niwa et al., 1991, Gene 108:193-199). The pCAGGS vector was modified to additionally produce vRNA from the cDNA template by insertion of a human RNA poll promoter sequence and a mouse terminator sequence with adjacent SapI recognition sequences. Purified vector pDZ and the individual SapI-digested cDNA inserts (molar ratio of 1:3, except for PB2 1:7) were ligated using the Roche Rapid DNA ligation kit (Roche Applied Bioscience, Indianapolis, Ind.) according to the manufacturer's recommendations. A genetic tag was inserted into the NS-encoding plasmid by silent mutagenesis. Nucleotides 447 to 452 (cDNA 5'-CTGGAA-3') (SEQ ID NO:19) were replaced with 5'-CTCGAG-3' (SEQ ID NO:20), resulting in two silent mutations and the creation of a novel Xho1 restriction enzyme site. DH5α E. coli cells (Invitrogen) were transformed and screened for correct constructs using the QIAGEN miniprep system. All constructs were sequenced at the Mount Sinai DNA Core Sequencing facility. Stocks of DNA were prepared by transforming bacterial cells with approximately 20 ng of the miniprep DNA and purifying with the Qiagen plasmid maxiprep system. Plasmid pPOLI has a truncated human polymerase I promoter and a hepatitis delta virus ribozyme separated by two SapI sites (Pleschka et al., 1996, J. Virol. 70:4188-4192). This plasmid was used for construction of the three NS1 mutants; pPOLI-Eq-NS1-126, pPOLI-Eq-NS1-99 and pPOLI-Eq-NS1-73. The coding region of A/eq/KY/5/02 NS segment is 657 nucleotides long (219 amino acids). The name of the mutated NS1 construct corresponds to the length of the protein that is expressed from the plasmid. Desired deletions were introduced by PCR of the pDZ-EQ-NS construct and the primers used (5'-GATAAGTAGATCTTGATTAATTAA-GAAGGA-3' for NS1-126 (SEQ ID NO:21); 5'-ATGTCAT-GATTAATTAAGAAGGA-3' for NS1-99 (SEQ ID NO:22); and 5'-GAATCATAAGCTTTAATTAAGAAGGA-3' for NS1-73 (SEQ ID NO:23)) were designed to introduce stop codons in each reading frame and unique restriction sites into each segment (see FIG. 1(a)). The Eq-NS1-126 construct has a deletion of nucleotides 405 to 482, an introduction of four stop codons, a BglII site and a PacI site. The Eq-NS1-99 construct has a deletion of nucleotides 324 to 482, an introduction of three stop codons, an AseI site and a PacI site. The Eq-NS1-73 construct has a deletion of nucleotides 246 to 482, an introduction of three stop codons, a HindIII site and a PacI site. The three constructs were sequenced across the entire NS gene to confirm the novel changes.

6.1.4 Rescue of Infectious Virus from cDNA 0.5 µg of each of the eight ambisense plasmids (pDZ-Eq-PB2, pDZ-Eq-PB1, pDZ-Eq-PA, pDZ-Eq-HA, pDZ-Eq-NP, pDZ-Eq-NA, pDZ-Eq-M, pDZ-Eq-NS) and 1.0 µg of each of five protein expression plasmids (pCAGGS-WSN-PB1, pCAGGS-WSN-PB2, pCAGGS-WSN-PA, pCAGGS-WSN-NP, pCAGGS-Eq-NS1) were diluted to a total volume of 50 µl in OptiMEM (GIBCO, Invitrogen). Expression plasmids for the H1N1 virus A/WSN/33 were included to improve rescue efficiency. The DNA solution was added to a mix of 10 µl of cationic liposomal reagent, Lipofectamine 2000 (Invitrogen), in 240 µl of OptiMEM. The transfection mixture was incubated at room temperature for 30 minutes. One milliliter of OptiMEM was added to the transfection mixture and then mixed with 250 µl of freshly trypsinized 293T cells resuspended in OptiMEM, enough for ~50% confluence in 35 mm dishes. After 6 hours incubation at 37° C., 5% $CO_2$, the transfection supernatant was removed and 1 ml of freshly trypsinized MDCK cells resuspended in OptiMEM with 0.3% bovine albumin (Sigma-Aldrich, St. Louis, Mo.) and 1% penicillin/streptomycin (GIBCO) were added. Twelve hours later, 1 ml of OptiMEM containing 1 µg/ml of TPCK-trypsin was added to the dish. Another 1 µg of TPCK-trypsin was added 24 hours later. Seventy-two hours post infection, 100 µl of the supernatant was used to inoculate 7 to 10 day-old embryonated chicken eggs at 37° C., 5% $CO_2$, for 48 hours. NS1 mutant viruses were propagated in 7 day-old eggs which do not have a competent interferon system; full length recombinant A/eq/KY/5/02 virus was propagated in 8-11 day-old eggs. Harvested allantoic fluid was serially diluted in phosphate buffered saline (PBS, GIBCO) and assayed for hemagglutination of 0.5% Cox hen red blood cells (CBT Farms, Chestertown, Md.) in v-bottom, 96-well plates.

6.1.5 Western Blot Analysis

Cell extracts were made in a lysis buffer: 0.5% NP-40, 150 mM NaCl, 20 mM Hepes pH 7.4, 1 mM EDTA, 1 mM EGTA, 10% glycerol and Complete protease inhibitor cocktail (Roche). Ten or twenty microliters of protein lysate were loaded onto a 12% SDS-polyacrylamide gel. Separated proteins were probed for analysis of the NS1 protein with a rabbit polyclonal antibody generated against the first 73 amino acids of the protein (unpublished data). A mouse monoclonal antibody against the viral M1 protein (ATCC hybridoma M2-1C6-4R3) was also included as a positive control.

6.1.6 Bioassay for IFN Production

To determine the amount of IFN produced in cells infected with the different recombinant viruses, we modified a bioassay previously described (Park et al., 2003, J. Virol. 70:9522-9532). Six-well dishes of confluent FEK cells were infected at a MOI of 1.5 with each of the four equine recombinant viruses, Eq-rWT, Eq-NS1-126, Eq-NS1-99 and Eq-NS1-73 for 11 hours. The infected cells were maintained in MEM supplemented with 0.3% bovine albumin, 1% penicillin/streptomycin and 6% allantoic fluid. At two hour intervals post infection 100 µl of supernatant was collected and any virus present was UV inactivated in plates 6 inches from an 8-Watt UV lamp (UVP, Upland, Calif.) for 20 minutes. Flat-bottomed, 96-well plates of confluent FEK cells were treated with the inactivated supernatants for 24 hours and then infected with VSV-GFP at an MOI of 0.1. For controls, the cells were also mock treated or treated with 1 Unit/ml of Universal type I interferon (PBL Biomedical Laboratories, NJ). At 20 hours post-infection, the cells were examined for GFP under a fluorescence microscope (Olympus IX70).

6.1.7 Viral Growth Kinetics

A comparison of viral growth kinetics for the recombinant wild-type and the three NS1 mutant viruses was undertaken in MDCK cells and embryonated hen eggs. Near confluent 12-well plates of MDCK cells were infected with each of the viruses at MOIs of 0.1, 0.01 and 0.001. Infected cells were maintained in MEM supplemented with 0.3% bovine albumin, 1% penicillin/streptomycin and 1 µg/ml TPCK-trypsin. The viral titer in the supernatant of infected cells was examined daily for 5 days by hemagglutination assay as previously described. The allantoic cavities of 7, 9 and 11 day-old embryonated eggs were also infected with 1000 PFU of each of the recombinant equine viruses. Six eggs were infected with 100 µl of each virus per egg age group. Allantoic fluid was withdrawn from each of the eggs at 24, 48 and 72 hours post-infection and examined for hemagglutination.

6.1.8 Viral Replication in Mouse Lungs

Six-week-old female C57/BL6 mice (Jackson Laboratories) were sedated with ether and infected intranasally with 50 µl of $1 \times 10^5$ PFU of equine influenza recombinant virus. Influenza A/WSN/33 virus and sterile PBS were included as controls. Mice were sacrificed on days 2 and 4 post infection: five mice per equine virus, four for WSN and 1 for PBS on each day. Lungs were removed, homogenized and resuspended in sterile PBS. Viral lung titers were determined by immunofluorescence. Briefly, a 96-well plate of confluent MDCK cells was infected with 20 µl of limiting dilutions of virus. Seven hours post-infection the cells were fixed with 5% paraformaldehyde in PBS. A rabbit polyclonal antibody against PR8 virus was used for detection of infected cells, which were counted at the most limiting dilutions to determine the virus titer. All procedures were conducted in accordance with National Institutes of Health guidelines for the care and use of laboratory animals.

6.2 Results 6.2.1 Construction of NS1 Mutants

Plasmid pPOLI was used for construction of the three equine influenza virus NS1 mutants; pPOLI-Eq-NS1-126, pPOLI-Eq-NS1-99 and pPOLI-Eq-NS1-73. The coding region of the A/eq/KY/5/02 NS segment is 657 nucleotides long (219 amino acids). Sequential C-terminal truncations were made to this segment resulting in three constructs encoding for the first 126, 99 or 73 amino acids of the NS1 protein. The nuclear export protein (NEP) open reading frame was not altered in these constructs (FIG. 1(a)). Desired deletions were introduced by PCR using the pDZ-Eq-NS construct as template. The primers used were designed to introduce stop codons in each reading frame and unique restriction sites into each segment.

6.2.2 Rescue of Recombinant Equine Influenza Viruses

To generate an equine influenza virus using reverse genetics, the eight viral RNAs from A/eq/KY/5/02 were cloned into the ambisense plasmid pDZ. Upon transfection of these plasmids along with five protein expression plasmids encoding for WSN-PB1, WSN-PB2, WSN-PA, WSN-NP, and Eq-NS1 in 293T/MDCK co-cultured cells and subsequent passage into embryonated eggs, infectious virus was recovered. The three viruses with truncated NS1 proteins were rescued in the same manner as the full length recombinant equine virus. NS1 mutant viruses were propagated in 7 day-old eggs which do not have a competent interferon system, whereas, full length recombinant A/eq/KY/5/02 was propagated in 8-11 day-old eggs. RT-PCR was carried out on RNA extracted from allantoic fluid of HA-positive rescued virus preparations. Sizes of the generated cDNAs confirmed the rescue of the specific viruses (FIG. 1(b)). The genetic tag in the recombinant wild-type virus was used to confirm equine influenza virus rescue from cloned cDNA and to rule out the possibility of contamination with wild type-virus (data not shown). As previously described, each of the mutant viruses has a unique restriction site. NS DNA from the mutant viruses was also digested with these specific enzymes for additional proof that each virus contained the correct NS segment (data not shown).

6.2.3 Expression of NS1 Proteins

Thirty five millimeter dishes of confluent MDCK cells were infected at an MOI of 1.5 with each of the four equine recombinant viruses, Eq-rWT, Eq-NS1-126, Eq-NS1-99 and Eq-NS1-73 for 2, 4, 6 and 8 hours. A polyclonal antibody against the amino terminus of the NS gene, common to the parental wild-type virus and the three derived NS1 mutants, was used to probe for the protein. Expression of the viral M1 protein was also examined as a control (FIG. 2(a)). Expression of the rWT NS1 protein can be seen as early as four hours post-infection with levels increasing up to 8 hours. The NS1-73 virus protein expression was detectable at 6 hours post-infection. Cells infected with the NS1-99 virus had visible NS1 protein expression at 8 hours PI. Expression of the NS1-126 protein was undetectable 8 hours post-infection at this MOI. Expression of the M1 protein at 6 and 8 hours post-infection was comparable for all recombinant mutant viruses, however, cells infected with the NS1-126 virus were expressing M1 protein at earlier time points compared to NS1-99 and NS1-73. In addition, cells were infected with each of the recombinant viruses at an MOI of 5 for 8 hours in order to see expression of the NS1-126 protein (FIG. 2(b)). There was a clear reduction in levels of NS1 protein expression in cells infected with the mutant viruses compared to cells infected with the recombinant wild-type virus. These data indicate that the mutated NS1 viruses still express their truncated NS1 proteins albeit at lower levels compared to the rWT virus.

6.2.4 Induction of IFN By Recombinant Equine Viruses

The ability of the mutated equine viruses to counteract the anti-viral cytokine response (IFN) in equine primary cells infected with equine influenza virus was compared. For this purpose a bioassay which measured the production of IFN in infected cells was employed (FIG. 3(a)). FEK cells were induced to produce interferon by infection with the recombinant viruses. Supernatants of the infected cells were collected at different time points post-infection and were UV-inactivated. Fresh cells were then treated with the supernatants for 24 hours to induce an anti-viral state. The anti-viral cytokine response induced by the different viruses by looking at VSV-GFP replication in the cells treated with supernatants was compared (FIG. 3(b)). The mutant viruses were expected to induce different levels of IFN in the infected FEK cells and subsequently promote an anti-viral state in treated fresh FEK cells. The level of inhibition of VSV-GFP replication in these cells is a reflection of the amount of IFN produced in cells infected with the equine viruses. VSV-GFP replication was inhibited when cells were treated with as low as 1 Unit/ml of universal IFN. When comparing the levels of IFN produced in the equine virus infected cells, rWT did not induce IFN until 9 hours post-infection as seen by the ability of VSV to replicate in the treated cells up until this point. In comparison to rWT, the NS1-73 virus was attenuated in its ability to block the anti-viral response as IFN was clearly being produced at 5 hours post-infection. The NS1-99 and NS1-126 viruses were also attenuated in this respect, the latter more severely so.

6.2.5 Viral Replication in MCDK Cells

Viral growth kinetics for the recombinant wild type and the three NS1 mutant viruses were examined in MDCK cells. Cells were infected with each of the viruses at MOIs of 0.1, 0.01 and 0.001 (FIG. 4). The viral growth in the supernatant of infected cells was examined daily for 5 days by hemagglutination assay. At a higher MOI (0.1), the rWT virus replicated to highest titers, with the NS1-99 and NS1-73 viruses reaching lower HA titers. The NS1-126 virus was severely attenuated in its replication. At an MOI of 0.01, the same trend was seen with the NS1-99 and NS1-73 viruses which replicated at significantly lower titers compared to wild-type. The NS1-126 virus did not replicate at all at this MOI. Finally, at the lowest MOI of 0.001, the NS1 mutant viruses were highly attenuated in comparison to the rWT virus. The parental strain only grew to an HA titer of 16, but the mutant viruses did not grow to significant titers or were below the detection limit.

6.2.6 Viral Replication in Embryonated Hen Eggs

To assess viral replication in embryonated eggs, the allantoic cavities of 7, 9 and 11 day-old eggs were infected with 1000 PFU of each of the recombinant equine viruses. Allantoic fluid was withdrawn from each of the eggs at 24, 48 and 72 hours post-infection and the average HA titer from six eggs for each group was calculated as seen in FIG. 5. Interestingly, in 7 day-old eggs, the mutant viruses NS1-73 and NS1-99 actually grew better (HA 107 and 64, respectively) than the rWT which grew to an HA titer similar to NS1-126. However in 9 and 11 day-old eggs, the mutant viruses were much more attenuated in their ability to replicate in comparison to the rWT virus. In these eggs the rWT grew to an HA titer of 128 and 472, respectively, which was significantly higher than the best growing mutant virus, NS1-73.

6.2.7 Viral Replication in Mice

The viral growth kinetics for the recombinant wild-type and the three NS1 mutant viruses was examined in vivo by infecting six-week-old female C57/BL6 mice with $1 \times 10^5$ pfu of each of the viruses. Influenza A/WSN/33 virus and sterile PBS were included as controls. Viral titers in the lungs of the mice on days 2 and 4 post-infection were measured by immunofluorescence and a mean titer per group is seen in FIG. 6. All of the recombinant equine viruses except for NS1-126 replicated in mouse lungs with a decrease in titer going from day 2 to day 4. As with the viral growth kinetics seen in vitro, NS1-73 virus was the least attenuated of the three mutant viruses with ~1.5 logs lower growth in comparison to the rWT. NS1-99 virus was more attenuated than NS1-73 virus being over 5 logs lower than the rWT on day 2 post-infection. NS1-126 virus was the most attenuated of the mutant viruses, as it was not detectable in mouse lungs on either day lung titers were measured.

6.3 Discussion

Applicants have established a plasmid-based reverse genetics system (or helper-free plasmid system) for equine influenza virus. Utilizing this method, Applicants have generated three recombinant equine influenza viruses encoding carboxy-terminally truncated NS1 proteins of 73, 99 or 126 amino acids in length. The data demonstrates that in comparison to the rWT parental virus, the mutant NS1 viruses induce IFN production at earlier time points in a primary equine cell culture system. Specifically, the NS1-126 virus induces IFN production earliest, followed by the NS1-99 and NS1-73 viruses.

Applicants have also found that the three mutated equine influenza viruses were attenuated in their replication in comparison to wild-type virus in cell culture and in embryonated eggs. Again, this attenuation of mutant NS1 viruses was seen as NS1-73 being least attenuated, followed by NS1-99 and NS1-126 being most attenuated. The same pattern of attenuation in replication seen with the three mutants (NS1-126>NS1-99>NS1-73) in eggs and tissue culture was also seen in vivo in the mouse model. In this system the NS1-126 virus was unable to replicate to detectable levels in the mouse lung.

As discussed supra, attenuation does not follow the same pattern in that the NS1-73 virus was the most virulent of the mutants, followed by NS1-99 and NS1-126. Applicants speculate that the basis for attenuation of the generated equine NS1 mutants is related to their levels of NS1 protein expression as seen from the Western Blot analysis (FIG. 2). Cells infected with NS1-73 and NS1-99 viruses had higher levels of NS1 protein expression than cells infected with the NS1-126 virus. The differing amounts of NS1 protein expressed by the mutant viruses may be due to decreased protein stability as a result of the C-terminal truncations that were made.

6.4 Equivalents

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

Various references are cited herein, the disclosure of which are incorporated by reference in their entirety.

What is claimed is:

1. A vaccine formulation comprising a genetically engineered attenuated equine influenza virus having an impaired interferon antagonist phenotype and a pharmaceutically acceptable carrier, wherein said virus comprises an equine influenza virus NS1 gene with a mutation resulting in a deletion of all of the amino acid residues of NS1 except amino acid residues 1-126.

2. The vaccine formulation of claim 1, wherein the genetically engineered attenuated equine influenza virus that expresses a heterologous sequence.

3. The vaccine formulation of claim 2, wherein the virus expresses a tumor antigen.

4. The vaccine formulation of claim 2, wherein the virus expresses an epitope of a foreign pathogen.

5. A method for inducing an immune response in a horse, comprising administering to said horse an effective amount of the vaccine formulation of claim 1.

6. A method for inducing an immune response in a horse, comprising administering to said horse an effective amount of the vaccine formulation of claim 2.

* * * * *

UNITED STATES PATENT AND TRADEMARK OFFICE
CERTIFICATE OF CORRECTION

| | |
|---|---|
| PATENT NO. | : 8,137,676 B2 |
| APPLICATION NO. | : 11/884401 |
| DATED | : March 20, 2012 |
| INVENTOR(S) | : Palese et al. |

It is certified that error appears in the above-identified patent and that said Letters Patent is hereby corrected as shown below:

On the title page, in the Attorney, Agent, or Firm, Item (74) replace "Jones Days" with --Jones Day--.

Col. 1, lines 5-6, replace "PCT/US2005/019383, filed June 5, 2005, which" with --PCT/US2005/019383, filed June 1, 2005, which--.

Col. 19, lines 4-5, replace "from strain A/WSN/33 A/Eq/KY/5/02)." with --from strain A/Eq/KY/5/02).--.

In claim 2, at col. 75, lines 19-21, replace "The vaccine formulation of claim 1, wherein the genetically engineered attenuated equine influenza virus that expresses a heterologous sequence." with --The vaccine formulation of claim 1, wherein the genetically engineered attenuated equine influenza virus expresses a heterologous sequence.--.

Signed and Sealed this
Twenty-second Day of May, 2012

David J. Kappos
*Director of the United States Patent and Trademark Office*